United States Patent [19]
Diamond et al.

[11] Patent Number: 6,166,288
[45] Date of Patent: Dec. 26, 2000

[54] METHOD OF PRODUCING TRANSGENIC ANIMALS FOR XENOTRANSPLANTATION EXPRESSING BOTH AN ENZYME MASKING OR REDUCING THE LEVEL OF THE GAL EPITOPE AND A COMPLEMENT INHIBITOR

[75] Inventors: Lisa E. Diamond, Princeton; John S. Logan, Robbinsville; Geurard W. Byrne, Allentown; Ajay Sharma, Lawrenceville, all of N.J.

[73] Assignee: Nextran Inc., Princeton, N.J.

[21] Appl. No.: 08/675,773

[22] Filed: Jul. 3, 1996

Related U.S. Application Data

[60] Provisional application No. 60/004,461, Sep. 27, 1995.

[51] Int. Cl.$^7$ ................................................. A01K 67/00
[52] U.S. Cl. ............................... 800/17; 800/21; 800/22; 800/25; 800/3
[58] Field of Search ...................... 435/172.3; 424/93.21, 424/93.1; 514/44, 2; 800/2, DIG. 1–4, 17, 21, 22, 25, 3

[56] References Cited

U.S. PATENT DOCUMENTS

| | | | |
|---|---|---|---|
| 4,873,191 | 10/1989 | Wagner et al. | 435/172.3 |
| 5,324,663 | 6/1994 | Lowe | 435/320.1 |

FOREIGN PATENT DOCUMENTS

| | | | |
|---|---|---|---|
| 9105855 | 5/1991 | WIPO . | |
| WO 91/05855 | 5/1991 | WIPO | 800/2 |
| 9302188 | 2/1993 | WIPO . | |
| 9402616 | 2/1994 | WIPO . | |
| 9406903 | 3/1994 | WIPO . | |
| 9417822 | 8/1994 | WIPO . | |
| 9524495 | 9/1995 | WIPO . | |
| 9528412 | 10/1995 | WIPO . | |
| 9534202 | 12/1995 | WIPO . | |
| 9606937 | 3/1996 | WIPO . | |
| 9612804 | 5/1996 | WIPO . | |

OTHER PUBLICATIONS

Logan et al., "Transgemic swine as a recombinant production system for human hemoglobin", Methods in Enzymology 231:435–445 (1994).

Medof et al., "Cloning and characterization of cDNAs encoding the complete sequence of decay–accelerating factor of human complement", Proceedings of the National Acadamy of Sciences 84(Apr.):2007–2011 (1987).

Mulins et al., "Fulminant hypertension in transgenc rats harbouring the mouse Ren–2 gene", Nature 344 (Apr. 5):541–544 (1990).

Palmiter et al., "Germ–line transformation of mice", Ann. Rev. Genetics 20:465–499 (1986).

Purcell et al., "Alternately spliced RNAs encode several isoforms of D46 (MCP), a regulator of complement activation", Immunogenetics 33:335–344 (1991).

Riley et al., Techniques for the Analysis of Complex Genomes: Chapter 4: Construction, characterization and screening of YAC libraries, (Book) 1992.

Schedl et al., "Transgenic mice generated by pronuclear injection of a yeast artificial chromosome", Nucleic Acids Research 20(12):3073–3077 (1992).

Schedl et al., "A yeast artificial chromosome covering the tyrosinase gene confers copy number–dependent expression in transgenic mice", Nature 362(Mar. 18):258–261 (1993).

Tone et al., "Gene structure of Human CD59 and demonstration that discrete mRNAs are generated by alternative polyadenylation", J. Mol. Biol. 227:971–976 (1992).

Van den Berg et al., "Complement–inhibiting activities of human CD59 and analogues from rat, sheep, and pig are not homologously restricted", Journal of Immunology 152:4095–4101 (1994).

Vaughan et al., "Biochemical analysis of pig xenoantigens detected by human antibodies", Transplantation Proceedings 25(5):2919–2920 (1993).

Ye et al., "Removal of dog antipig antibody by adsorption with pig red blood cell stroma columns", Transplantation Proceedings 24(2):563–565 (1992).

Agishi et al., "Comparative evaluation of immunoadsorption and double filtration plasmapheresis for removal of anti–A or –B in ABO–incompatible kidney transplantation", Transplantation Proceedings 24(2):557–558 (1992).

Aird et al., "Human von Willebrand factor gene sequences target expression to a subpopulation of endothelial cells in transgenic mice", Proc. Natl. Acad. Sci. 92(May):4567–4571 (1995).

(List continued on next page.)

*Primary Examiner*—Jasemine C. Chambers
*Assistant Examiner*—Deborah J. R. Clark
*Attorney, Agent, or Firm*—Iver P. Cooper; Janice Guthrie

[57] ABSTRACT

A method of xenotransplanting organs, tissues, cells or non-viable components which reduces or prevents antibody-mediated rejections, including hyperacute rejection, is provided wherein transgenic animals are produced that express at least one enzyme which masks or reduces the level of the antigenic Gal$\alpha$(1,3)Gal or gal epitope, and at least one complement inhibitor such as CD59, DAF and/or MCP. The transgenic animals which express both a gal epitope-reducing enzyme and a complement inhibitor will have masked or reduced levels of the gal epitope and will be much less likely to produce an antibody-mediated rejection following transplantation, and the expression of the complement inhibitor will also suppress complement activation and reduce even further a severe immune reaction following the transplantation of donor organs, tissue, cells or non-viable components from the transgenic animals so produced. In addition, transgenic animals are provided which express a plurality of complement inhibitors or other proteins from a locus of genes at a single integration site. The present invention is thus advantageous in that it can provide xenogeneic organs, tissues, cells and non-viable components which can be transplanted safely and effectively into humans with a reduction or elimination of antibody-mediated rejection to an extent not previously possible, and which will significantly reduce the need to obtain donor organs, tissues, cells or non-viable components from human or primate donors.

40 Claims, 19 Drawing Sheets

OTHER PUBLICATIONS

Blanken et al., "Biosynthesis of terminal Gal alpha $1-_{Gal}$ beta1–4GlcNAc–R Oligosaccharide sequences on glyco–conjugates", Journal of Biological Chemistry 260(24):12927–12934 (1985).

Cary et al., "Tissue expression of human decay accelerating factor, a regulator of complement activation expressed in mice: A potential approach to inhibition of xenograft rejection", Transplantation Proceedings 25(1):400–401 (1993).

Cooper et al., "Oligosaccharides and discordant xenotransplantation", Immunological Reviews 141:31–59 (1994).

Cozzi et al., "Comparative analysis of human DAF expression in the tissues of transgenic pigs and man", Transplantation Proceedings, 27(1):319–320 (1995).

Dalmasso et al., "Inhibition of complement–mediated endothelial cell cytotoxicity by decay–accelerating factor", Transplantation 52(3):530–533 (1991).

Dalmasso et al, "Mechanism of complement $_a$ctivation in the hyperacute rejection of porcine organs trans–planted into primate recipients", Am. J. Path. 140(5):1157–1166 (1992).

Dumont et al., "Dominant–negative and targeted null mutations in the endothelial receptor tyrosine kinase, tek, reveal a critical role in vasculogenesis of the embryo", Genes and Development 8:1897–1909 (1994).

Fearon et al., "Regulation by membrane sialic aid of bea1H–dependent decay–dissaciation of amplification C3 convertase of the alternative complement pathway", Proc. Natl. Acad. Sci. 75(4):1971–1975 (1978).

Fischel et al., "Plasma exchange, organ perfusion, and immunosuppresion reduce 'natural' antibody levels as measured by binding to xenogeneic endothelial cells and prolong discordant xenograft survival", Transplantation Proceedings 24(2):574–575 (1992).

Fodor et al., "Expression of a functional human complement inhibitor in a transgenic pig as a model for the prevention of xenogeneic hyperacute organ rejection", Proc. Natl. Acad. Sci. 91(Nov.):11153–11157 (1994).

Galili et al., "Man, apes and old world monkeys differ from other mammals in the expression of alpha–galactosyl epitopes on nucleated cells", J. Biol. Chem. 263(33):17755–17762 (1988).

Galili et al., "Evolutionary relationship between the natural anti–Gal antibody and the Gal alpha1–3Gal epitope in primates", Proc. Natl. Acad. Sci. 84(Mar):1369–1373 (1987).

Gewurz et al., "Effect of cobra venom–induced inhibition of complement activity on allograft an xenograft reations", Transplantation 5(5):1296–1303 (1967).

Good et al., "Identification of carbohydrate structures that bind human antiporcine antibodies: Implications for discordant xenografting in humans", Transplantation Proceedings 24(2):559–562 (1992).

Burgers et al., "Transformation of Yeast Spheroplasts without Cell Fusion", Analytical Biochemistry 163:391–397 (1987).

Burke et al., "Cloning of Large Segments of Exogenous DNA into Yeast by Means of Artificial Chromosome Vectors", Science 236:806–812 (1987).

Byrne et al., "Protection of Xenogeneic Cardiac Endothelium From Human Complement by Expression of CD59 or DAF in Transgenic Mice", Transplantation 60(10):1149–1156 (1995).

Caras et al., "Cloning of decay–accelerating factor suggests novel use of splicing to generate two proteins", Nature 325:545–549 (1987).

Denman et al., "Transgenic expression of a variant of human tissue–type plasminogen activator in goat milk: Purification and characterization of the recombinant enzyme."Bio/Technology 9:839–843 (1991).

Gaensler et al., "Germ–line transmission and development regulation of a 150–kb yeast artificial chromosome containing the human beta–globin locus in transgenic mice", Proc. Natl. Acad. Sci. 90:11381–11385 (1993).

Gnirke et al., "Microinjection of intact 200– to 500–kb fragments of YAC DNA into mammalian cells", Genomics 15:659–667 (1993).

Hammer et al., "Production of transgenic rabbits, sheep and pigs my microinjection", Nature 315(Jun. 20): 680–683 (1985).

Hanasaki et al., "Cytokine–indiced beta–galactoside alpha–2,6–sialytransferase in human endothelial cells mediates alpha–2,6–sialylation of adhesion molecules and CD33 ligands", Journal of Biological Chemistry 269 (14):10637–10643.

Jaenisch et al., "Germ line integration and Medelian transmission of the exogenous Moloney leukemia virus" Proceedings of the National Academy of Sciences 73(4):1260–1264 (1976).

Ketner et al., "Efficient manipulation of the human adenovirus genome as an infectious yeast artificial chromosome clone", Proceedings of the National Academy of Science 91(Jun.):6186–6190 (1994).

Kinoshita et al., "Biology of complement: The overture", Immunology Today 12(9):291–295 (1991).

Krimpenfort et al., "Generationof trangenic diary cattle using 'in vitro' embryo production", Bio/Technology 9:844–847 (1991).

Laherty et al., "Characterization of the promoter region of the human thrombospondin gene", J. Biol. Chem. 264(19):11222–11227 (1994).

Harats et al., "Targeting gene expression to the vascular wall in transgenic mice using the murine prepro–endothelin–1 promoter", J. Clin. Investigation 95(Mar.):1335–1344 (1995).

Kitagawa et al., "Differential expression of five sialytransferase genes in human tissue", J. Biol. Chem., 269(27):17872–17878 (1994).

Kornfield et al., "Assembly of asparagine–linked oligosaccharides", Ann. Rev. Biochem. 54:631–664 (1985).

Larsen et al., "Framshift and nonsense mutations in a human genomic sequence homologous to a murine UDP–Gal: beta–D–Gal(1,4)–D–GlcNA alpha(1,3)–galactosyltransferase cDNA", J. Biol. Chem. 265(12):7055–7061 (1990).

Larsen et al., "Molecular cloning, sequence, and expresion of a human GDP–L–fucos:beta–D–galactoside 2–alpha–L––fucosyltransferase cDNA that can form the H blood group antigen", Proc. Natl. Acad. Sci. 87(Sep.): 6674–6678 (1990).

Lexer et al., "Cardiac transplantation using discordant xenografts in a nonhuman primate model", Transplantation Proceedings 19(1):1153–1154 (1987).

Lowe et al., "Molecular cloning, expression, and uses of mammalian glycosyltransferases", Seminars in Cell Biology 2:289–307 (1991).

Miyagawa et al., "The mechanism of discordant xenograft rejection", Transplantation 46(6):825–830 (1988).

Moberg et al., "Prolongation of renal xenografts by the simultaneous sequestraton of preformed antibody, inhibition of complement, coagulation and antibody synthesis", Transplantation Proceedings 3(1):538–541 (1971).

Oldham et al., "Cell and tissue specific expression of a human CD59 minigene in transgenic mice", 2nd International Congress on Xenotransplantation:Abstract 60 (1993).

Paulson et al., "Glycosyltransferases", J. Biol. Chem. 264(30):17615–17618 (1989).

Platt et al., "Endothelial cell antigens recognized by zenoreactive human natural antibodies", Transplantation 50(5):817–822 (1990).

Platt et al., "Tranplantation of discordant xenografts:A review of progress", Immunology Today 11(12): 450–456 (1990).

Pruitt et al., "Effect of soluble complement receptor type 1 on natural antibody levels during xenograft rejection", Transplantation Proceedings 24(2):477–478 (1992).

Sandrin et al., "Anti–pig IgM antibodies in human serum react predominantly with Gal(alpha1,3)Gal epitopes", Proc. Natl. Acad. Sci. 90(Dec.):11391–11395 (1993).

Thorley et al., "Construction of Cd46 minogenes for the production of transgenic mice", Transplantation Proceedings 27(3):2177–2178 (1995).

Iwata et al., "Expression of a hybrid complement regulatory protein, membrne cofactor protein decay accelerating factor on chines hamster ovary", J. Immunology 152:3436–3444 (1994).

Oldham et al., "High–level tissue specific expression of human CD59, MCP, and DAF proteins from genomic clones in transgenic mice", Transplantation Proceedings 28(2):693 (1996).

McCurry et al., "Human complement regulatory proteins expressed in transgenic swine protect swine xenografts from humoral injury", Transplantation Proceedings 28(2):758 (1996).

Koike et al., "Introduction of alpha1–2fucosyltransferase and its effect in transgenic pig", Scientific Sessions & Business Meeting, 15th Annual Meeting p. 57 (1996).

Anonymous, "A dual strategy for developing animals as organ donors for humans", Research Disclosure, Sep. 1995 p. 37749.

Auchincloss, Hugh, "Xenogeneic Transplantation", Transplantation 46:1–20 (1988).

Oriol et al., "Carbohydrate antigens of pig tissues reacting with human natural antibodies as potential targets for hyperacute vascular rejection in pig–to–man organ xenotransplantation", Transplantation 56:1433–1442 (1993).

Cotterell et al., "The humoral immune response in humans following cross–perfusion of porcine organs", Transplantation 60:861–868 (1995).

Bach et al., "Barriers to xenotransplantation", Nature Medicine 1:869–873 (1995).

Larsen et al., "Molecular cloning, sequence, and expression of a human GDP–L–fucose:beta–D–galactosied 2–alpha–L–fucosylatransferase cDNA that can form the H blood group antigen", Proc. Natl. Acad. Sci. 87:6674–6678 (1990).

Sandrin et al., "Enzymatic remodelling of the carbohydrate surface of a xenogenic cell substantially reduces human antibody binding and complement–mediated cytolysis", Nature Medicine 1:1261–1267 (1995).

Kitagawa et al., "Cloning of Novel alpha2,3–Sialytransferase that Sialylates Glycoprotein and Glycolipid Carbohydrate Groups", J. Biol. Chem. 269(2):1394–1401 (1994).

Gillespie et al., "Cloning and expression of the Galβ1, 3GalNAc α2,3–Sialytransferase", J. Biol. Chem. 267(29) 21004–21010 (1992).

Kurosawa et al., "Cloning and expression of Galβ1,3GalNAc–specific GalNAc α2,6–Sialytransferase", J. Biol. Chem. 269(29):19048–19053 (1994).

Sharma et al., "Reduction in the level of Gal(α1,3)Gal in transgenic mice and pigs by the expression of an α(1, 2)fucosyltransferase", Proc. Natl. Acad. Sci. 93:7190–7195 (1996).

Gordon et al., "Transgenic Animals", Intl. Review of Cytology 115:171–229 (1989).

Connelly et al., "The role of transgenic animals in the analysis of various biological aspects of normal and pathologic states", Exper. Cell. Research 183:257–276 (1989).

Dorken et al., "B15 B–cell antigens: CDw75", Knapp et al., eds., Oxxford University Pres, pp. 109–110 (1989).

Platt et al., "Porcine platelet antigens recognized by human zenoreactive natural antibodies", Transplantation 57:327–335 (1994).

Platt et al., "Interstitial mononuclear cell populations in renal graft rejection", J. Exp. Med. 155:17–30 (1982).

Cohney et al., "Molecular cloning of the gene coding for pig alpha1–2fucosyltransferase", Immunogenetics, 44:76–79 (1996).

Bach et al., Strategies for Successful Xenotransplantation, Xenotransplantagion, Jun. 16–17, 1994.

Christiansen et al., "A functional analysis of recombinant soluble CD467 in vivo and a comparison with recombinant soluble forms of CD55 and CD35 in vitro", Eur. J. Immunol. 26:578–585 (1996).

Miyagawa, et al., 2nd Intl. Conf. of Xenotransplantation, Sep. 26–29, 1993.

Ikematsu, et al., "Transgenic mouse lines with ectopic expression of a–1,3–galactosyltransferase: production and characteristics", Glycobiology, 3(6):575–580 (1993).

Meri, et al., Distribution of Protectin (CD59), a Complement Membrane Attack Inhibitor, in Normal Human Tissues, Lab. Investigation, 65(5):532–537 (1991).

Lu, et al., Xenotransplantation, The FASEB Journal, vol. 8, pp. 1122–1130, Nov. 1994.

Sandrin, et al., Enzymatic remodelling of the carbohydrate surface of a xenogenic cell substantially reduces human antibody binding and complement–mediated cytolysis, Nature Medicine, vol. 1, No. 12, pp. 1261–1267, Dec. 1995.

Crystal, R.G. Transfer of genes to humans: early lessons and obstacles to success. Science, vol. 270, pp. 404–410, Oct. 20, 1995.

Schachter, H. Games People Play with Glycosyltransferase Genes. Abstract of Papers, American Chemical Society, vol. 207, CARB 23, Mar. 1994.

Somervelle et al. Functional expression of human CD59 in transgenic mice. Transplantation, vol. 58, No. 12, pp. 1430–1435, Dec. 27, 1994.

McCurry et al. Human complement regulatory proteins protect swine–to–primate cardiac xenografts from humoral injury. Nat. Med. vol. 1, No. 5, pp. 423–427, May 1995.

Diamond et al. Cell and tissue specific expression of a human CD59 minigene in transgenic mice. Transplantation proceedings, vol. 26, No. 3, p. 1239, Jun. 1994.

Houdebine, L M. Production of pharmaceutical proteins from transgenic animals. J. of Biotech. vol. 34, pp. 269–287, 1994.

Cozzi et al. The generation of transgenic pigs as potential organ donors for humans. Nat. Med. vol. 1, No. 9, pp. 964–966, Sep. 1995.

White D. Xenotranplantation and transgenic pigs: A solution to the problem of organ shortage in transplantation? Principals of drug development in transplantation and autoimmunity, ISBN 0–412–10061 pp. 703–705, 1996.

Wall R J. Transgenic Livestock: Progress and prospects for the future. Theriogeneology, vol. 45, pp. 57–68, 1996.

NEW YAC CLONING VECTOR FOR P1 ASSEMBLY

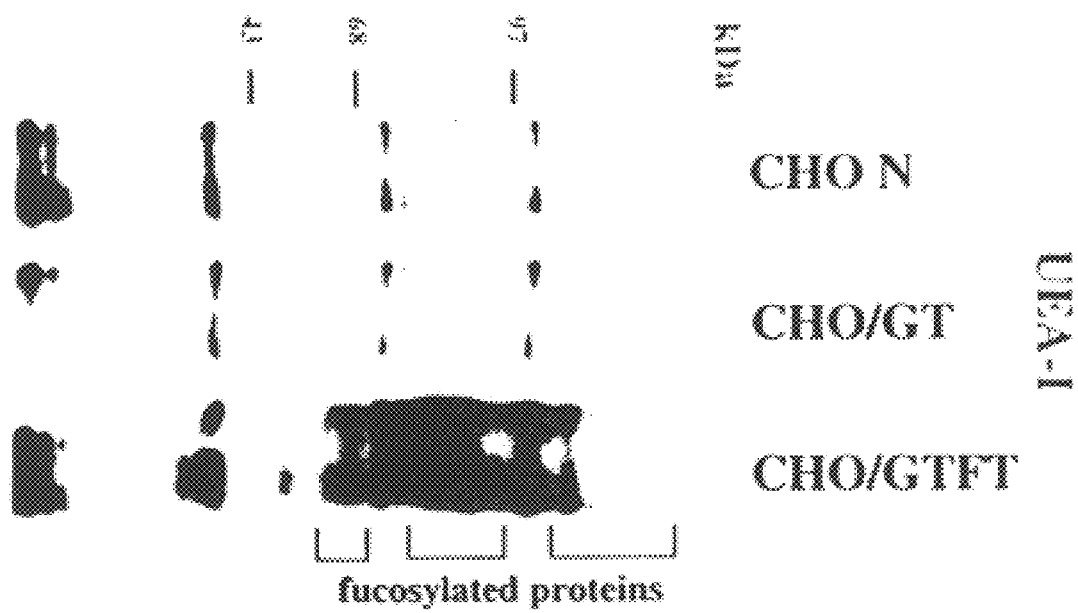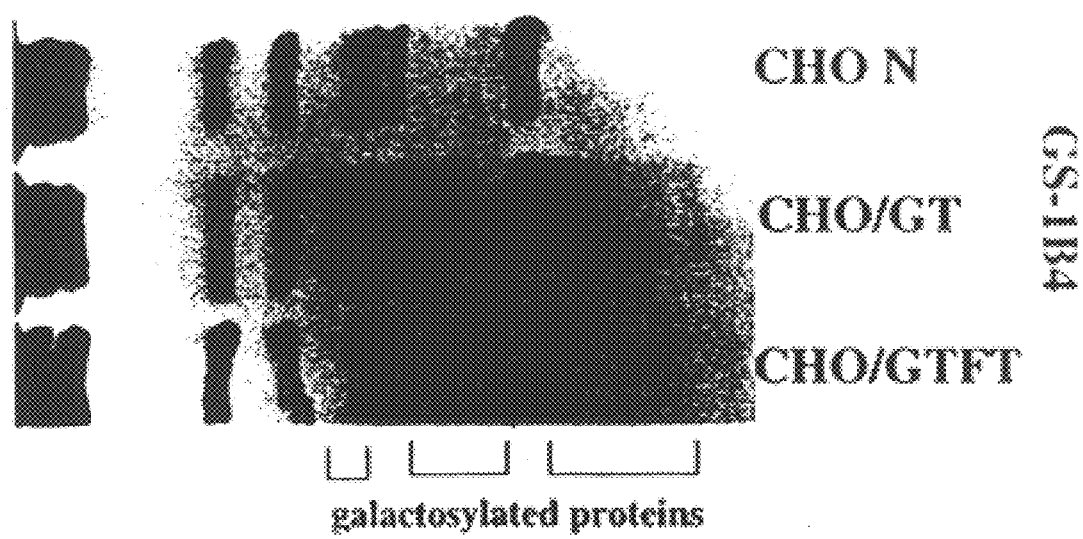
FIG. 10

METHOD OF PRODUCING TRANSGENIC ANIMALS FOR XENOTRANSPLANTATION EXPRESSING BOTH AN ENZYME MASKING OR REDUCING THE LEVEL OF THE GAL EPITOPE AND A COMPLEMENT INHIBITOR

This application claims priority from provisional U.S. patent application Ser. No. 60/004,461, filed Sep. 27, 1995.

FIELD OF THE INVENTION

The present invention is related in general to the preparation and use of transgenic animals and recombinant xenogeneic cells so as to reduce or prevent antibody-mediated and complement-mediated rejections, including hyperacute rejection, following xenotransplantation, and specifically to a method for reducing or preventing antibody-mediated and complement-mediated rejection following xenotransplantation which comprises the preparation of transgenic animals whose cells and tissues express a gene coding for an enzyme such as $\alpha(1,2)$fucosyltransferase, $\alpha(2,6)$sialyltransferase, $\beta(1,3)$N-acetylglucosaminyltransferase, or other suitable glycosyltransferase that will mask or reduce the level of the xenoreactive antigens, such as antigenic gal epitope, along with a gene that is capable of expressing a complement inhibiting protein, such as CD59, DAF, and/or MCP or other complement inhibitors, so as to produce organs, tissues, cells and non-viable components that reduce or eliminate antibody- or complement-mediated rejections following xenotransplantation. The invention also relates to the transgenic organs, tissues, cells and non-viable components produced by this method which express a plurality of complement inhibiting proteins and to a methods of xenotransplantation using organs, tissues, cells and non-viable components from the transgenic animals prepared in accordance with the invention.

BACKGROUND OF THE INVENTION

Despite the improvements over the past few years with regard to organ and tissue transplantation, advances in this field continue to be limited by severe shortages in usable human donor organs and tissues. In the past few years, many thousands of transplantation procedures have been performed using allograft tissues, i.e., tissues from a donor animal of the same species as the recipient. However, for any given year, the number of patients which could not obtain such an operation because of the lack of suitable donor tissue greatly exceeds the number of patients which receive the transplants. For example, in 1993, while 18,164 patients received donor organs, a total of 33,394 patients were still on the waiting list for donor organs by the end of that year. In many cases, such as for patients with heart disease, it is unfortunately the case that it is more likely the patient will die while waiting for a suitable donor organ to become available than as a result of complications associated with the transplantation procedure.

In addition, because of the unpredictable availability of organs, transplant surgeries often cannot be scheduled far in advance as would be a routine operation. All too frequently, surgical teams and hospital administrators have to react as soon as a suitable donor organ is located, thereby causing administrative and other difficulties. In the case of heart, liver and lung transplants, for example, if rejection is encountered it will not usually be possible to retransplant unless another suitable donor organ is located within a short period of time, and this is extremely unlikely to occur.

As a result of the shortage in suitable donor tissue, the scientific and medical community has for many years considered the feasibility of xenotransplantation, which is the transplantation of tissue from one species into an individual of a different species. Although there have been numerous attempts to successfully transplant organs or tissues into humans from certain closely related species such as chimpanzees and baboons, those operations have not been without problems, including varying levels of rejection and the requirement of extensive immunosuppressive treatments which can be both rigorous and costly, and which is often accompanied by unwanted side-effects. Moreover, the supply of potentially suitable donor primates is also restricted by other factors including the relatively small numbers of available primate populations, the fact that many potentially acceptable species are on the endangered species list, and other ethical considerations.

Accordingly, the search for suitable animal donors has focused on animals which are not endangered but are in relative ample supply, such as pigs. Unfortunately, xenotransplantation between humans and the most likely donor animal, the pig, has been severely limited due to the severe antibody-mediated rejection that occurs rapidly in humans following transplantation of the xenogeneic organs or tissues. This antibody-mediated rejection, which in its rapid initial stages is known as hyperacute rejection (or HAR), is thought to occur, at least with regard to transplants between pigs and primates, through antibody-mediated complement activation, such as described, e.g, in Dalmasso et al., *Amer. J. Pathol.* 140:1157–1166 (1992). It is also possible that the alternative pathway of complement is activated in this manner for other species combinations, although at least one paper has suggested that complement regulatory proteins may be species-specific. See Miyagawa et al., *Transplantation* 46:825–830 (1988).

With regard to hyperacute rejection in transplants of organs from pigs to humans or other primates, the initial stages of this antibody-mediated rejection are usually characterized by thrombosis, hemorrhage and edema, and almost invariably result in a decline in graft function and irreversible rejection within a period of a few minutes to a few hours following transplantation. It has been generally observed that this process is initiated by the binding of xenoreactive natural antibodies (or XNAs) to the carbohydrate structures present on the endothelial cells of the graft which in turn leads to the activation of the complement cascade. See, e.g., Platt et al., *Transplantation* 50:817–822 (1990).

The prevailing scientific view is that antibody-mediated rejections such as HAR ultimately result in additional rejections instituted by the host's complement defense system after initiation by the XNAs. Complement and its activation are now well known, see Roitt, *Essential Immunology* (Fifth Edition, 1994), Blackwell Scientific Publications, Oxford, and the activation ascribed to complement (C') depends on the operation of nine protein components (C1 to C9) acting in concert, of which the first consists of three major subfractions termed C1q, C1r and C1s. Complement can be activated by the classical or alternative pathway, both of which will now be briefly described.

In the classical pathway, C1 binds to antibody. The C1s subunit acquires esterase activity and brings about the activation and transfer to sites on the membrane or immune complex of first C4 and then C2. This complex has "C3-convertase" activity and splits C3 in solution to produce a small peptide fragment C3a and a residual molecule C3b, which have quite distinct functions. C3a has anaphylatoxin activity which contributes to complement-mediated damage, but otherwise plays no further part in the complement amplification cascade. C3b is membrane bound and can cause immune adherence of the antigen-antibody-C3b complex, so facilitating subsequent phagocytosis.

In the alternative pathway, the C3 convertase activity is performed by C3bB, whose activation can be triggered by extrinsic agents, acting independently of antibody. The convertase is formed by the action of Factor D on a complex of C3b and Factor B. This forms a positive feedback loop, in which the product of C3 breakdown (C3b) helps form more of the cleavage enzyme.

In both the classical and alternative pathways, the C3b level is maintained by the action of a C3b inactivator (Factor I). C3b readily combines with Factor H to form a complex which is broken down by Factor I and loses its hemolytic and immune adherence properties. The classical and alternative pathways are common after the C3 stage. C5 is split to give C5a and C5b fragments. C5a has anaphylatoxin activity and gives rise to chemotaxis of polymorphs. C5b binds as a complex with C6 and C7 to form a thermostable site on the membrane which recruits the final components C8 and C9 to generate the membrane attack complex (MAC). This is an annular structure inserted into the membrane and projecting from it, which forms a transmembrane channel fully permeable to electrolytes and water. Due to the high internal colloid osmotic pressure, there is a net influx of sodium ions and water, leading to cell lysis.

Complement inhibition or restriction factors have been identified which interfere with the action of the complement cascade in such a way as to reduce or prevent its lytic activity; they are often species-specific in that they are relatively ineffectual against complement derived from other species. These factors may be cell membrane bound, or free in serum. Most often they intervene in one of the steps common to both complement activation pathways, however, some factors may be specific to either the classical or the alternative pathway.

In a pig to primate transplant, the host's complement (C') is activated primarily through the classical complement pathway. Preformed xenoreactive natural antibodies (XNAs) circulating in the host's bloodstream recognize and bind to the donor organ, particularly on the luminal surface of the vascular endothelium. Binding of the XNAs serves to trigger the host's complement system. This attack leads to endothelial cell activation, adhesion of platelets and leukocytes, thrombosis and eventual necrosis of the xenograft organ within minutes to a few hours after transplantation. The capillary beds of the transplanted organ appear to be the most sensitive site for attack by the host's complement activity.

It has long been known that complement activation plays a critical role in antibody-mediated rejections such as HAR, as evidenced, e.g., in Gerwurz et al., *Transplantation* 5:1296 (1967). More recently, the involvement of complement in the antibody-mediated rejection process has been dramatically demonstrated by exogenous inhibition of host complement activity prior to xenotransplantation. For example, several groups have developed experimental methods to inhibit complement by depleting the level of xenogeneic natural antibodies in the host. The xenogeneic natural antibodies are removed either by perfusing the host's blood through a donor organ such as a pig kidney, or by passing the blood over an immunoaffinity column which removes immunoglobulin molecules. See, e.g., Moberg et al., *Trans. Proc.* 3:538–541 (1971); Fischel et al., *Trans. Proc.* 24:574–575 (1992); Ye et al., *Trans. Proc.* 24:563–565 (1992); Agashi et al., *Trans. Proc.* 24:557–558 (1992). Unfortunately, these methods are not readily transferable to routine use in a clinical transplantation setting.

Alternately, the administration of large amounts of cobra venom factor (see Gerwurz et al. 1967, cited above) or soluble complement receptor (see, e.g., Pruitt et al., *Trans. Proc.* 24:477–478, 1992) have been shown to be effective in reducing complement activity. Using these methods, at least two independent groups have shown that inhibition of host complement prior to transplantation leads to prolonged xenograft survival. See, e.g., Platt et al., *Immunol. Today* 11:450–456 (1990); Lexer et al., *Trans. Proc.* 19:1153–1154 (1987). Xenografts which would normally be rejected in a few hours have been maintained for days and weeks if the host complement is continuously suppressed. In addition, in Miyagawa et al., *Transplantation* 46:825–830 (1988), the mechanism of discordant xenograft rejection using a guinea pig-to-rat heart graft model was observed to occur by primary activation of complement via the alternative pathway, although the authors suggested that complement regulatory proteins may be species-specific. Complement regulatory proteins, or homologous complement restriction factors, have previously been described, for example, in PCT Application WO 91/05855 issued to Imutran Limited.

Other investigations in this area were conducted by Platt et al. (1990, cited above), who speculated that it might be possible to produce a transgenic pig which directly expressed human decay accelerating factor (DAF), and perhaps other complement regulatory proteins, in the membranes of the pig's endothelial cells. They thought that if such an animal was used as a donor animal, the human complement inhibitor would serve to protect the transplant from human complement. Platt et al. did not describe any specific genetic constructs for accomplishing this goal.

Dalmasso et al. (*Transplantation* 52:530–533, 1991) suggested engineering a transgenic donor animal, such as the pig, with human membrane-associated C-inhibitor genes to achieve a high level of expression of the corresponding proteins in the endothelial cells of the xenograft.

Consistent with this strategy, White et al., WO 91/05855, prepared transgenic mice bearing a transgene encoding human membrane cofactor protein (MCP) (also known as CD46) or human decay accelerating factor (DAF). The transgene was composed of a Friend spleen focus forming virus 5' long terminal repeat linked to a cDNA encoding the complement inhibitor. However, they did not determine whether these genes were expressed, and, if so, in which tissues, or whether a graft from the transgenic animal would elicit HAR in a discordant animal.

Similarly, Yannoutsos et al., *First Int'l Conqr. Xenotr.*, Abstracts, page 7 (1991), described the development of transgenic mice expressing human DAF and MCP. In this study a series of broad spectrum promoters were used so that it is possible that some of the total complement-inhibitor expression would take place in endothelial cells. Most of their animals appeared to have very low levels of complement-inhibitor expression. Furthermore, they did not confirm that expression in endothelial cells had been achieved, nor did they demonstrate biological function of the transgenically expressed CRP.

Transgenic mice and pigs which contain a human DAF gene have been produced using a partial genomic DNA fragment. (Cary et al., *Trans. Proc.* 25:400–401, 1993: Cozzi et al., *Trans. Proc.* 27:319–320, 1995). These animals allegedly exhibited widespread expression of DAF although there appeared to be little expression in hematopoietic tissues. The most consistent expression was observed in vascular smooth muscle, with variable expression in endothelium. It should be noted that the transgenic organs were not tested under transplantation conditions, rather PBMC cells were analyzed using both ELISA and RIA. Therefore no data is presented to suggest that these transgenic organs could prevent HAR in a transplant situation.

Oldham et al., in 1993, presented a talk at the 2nd International Congress on Xenotransplantation in which the production of a human CD59 minigene was announced as well as a modification of this minigene to allow for two cDNA sequences to be inserted into the minigene. Expression of the minigene, containing only the cDNA for CD59, in transgenic mice demonstrated a cell type distribution of CD59 protein expression similar to that seen in human tissues. However, there were problems with regard to this minigene that severely limited its usefulness.

Foder et al., *Proc. Nat. Acad. Sci. USA*, 91: 11153–57 (1994) sought to produce transgenic mice and swine producing the complement inhibitor CD59 by expressing CD59 under the control of the promoter of the mouse Major Histocompatibility Complex (MHC) Class I gene $H2K^b$. The latter gene encodes an antigen which is a predominant endothelial cell surface antigen. A CD59 cDNA was cloned into exon I of a 9.0 kb EcoRI genomic restriction fragment of the MHC gene. This fragment included a large 5' sequence, all 8 exons (and the intervening sequences), and a smaller 3' sequence. The authors demonstrated the presence of CD59 in the mouse heart, and in the tails of both mouse and pig; its expression elsewhere was not discussed. Expression was observed on both endothelial and non-endothelial cells.

Eighteen piglets were analyzed by DNA slot blot analysis and one animal was found to have 10–20 copies of the gene while two others contained only one copy of the gene and exhibited no expression or very low and inconsistent levels of expression in peripheral blood mononuclear cells (PBMCs). Low levels of CD59 were seen on a variety of tissues and cell types including fibroblasts, epithelial cells, vascular endothelial cells and smooth muscle cells. Expression of CD59 increased when stimulated with cytokines (which are known to induce the MHC class I promoter). Additionally, since the transgenic organs were not tested in a transplant situation, it is not known whether the organs would be susceptible to complement mediated rejection. Besides the promoters noted above, several other promoters have been used to achieve expression of a transgene in the endothelial cells of a transgenic animal. However, in these prior examples, the transgene was not a complement inhibitor.

Aird et al., *Proc. Nat. Acad. Sci. USA*, 92: 4567–71 (1995), has generated transgenic mice bearing a chimeric construct that included 487 bp of 5' flanking sequence and the first exon of the Human von Willebrand factor gene fused in-frame to the *E. coli* lacZ gene. Histochemical analysis of adult tissue demonstrated that LacZ expression was present in the endothelial cells of the blood vessels of the brain, yet activity was absent in the vascular beds of the spleen, lung, liver, kidney, testes, heart and aorta. Certain of the latter beds contain high levels of endogenous von Willebrand factor. This suggested that sequences other than those cloned are necessary for completely authentic expression of von Willebrand factor. One line did not exhibit LacZ activity in brain tissue, and one explanation for this finding is that genomic sequences at or near the site of transgene integration can influence the pattern of expression.

Aird's VWF promoter is of limited value for directing expression to endothelial cells due to its expression being limited to brain tissue. For comparison purposes, Aird et al. fused the *E. coli* lacZ gene to the promoter of an endogenous thrombomodulin gene by homologous recombination. The resulting transgenic mice exhibited LacZ activity in endothelial cells of all organs, including brain, spleen, lung, liver, heart, kidney and aorta.

Harats et al., *J. Clin. Invest.*, 95:1335 (1995), targeted gene expression to the vascular wall in transgenic mice using the murine preproendothelin-1 promoter. Their construct included 5.9 kb of the 5' flanking region, the first exon (with a luciferase reporter gene cloned into the BglII site in the noncoding region), and 0.9 kb of the first intron. In all mice, the highest level of expression was in the aorta, and high levels were also noted in other large arteries, in small muscular arteries, and to a lesser extent in capillaries. The level of expression in the veins was lower. Vascular expression was higher in the heart, kidney and lung than in the liver and spleen. Even in the same organ there was substantial variation in vascular expression. Some nonvascular expression was also observed.

Dumont et al., *Genes and Development*, 8:1897–1909 (1994), created transgenic mice that expressed the lacZ reporter gene under the control of the endothelial receptor tyrosine kinase promoter (tek). This promoter is regulated in a manner which has limited use, i.e., the promoter is turned on during embryonic development and subsequently turned off in the adult (Dumont et al., 1994).

The murine $H2K^b$ class 1 promoter allows for expression in endothelial cells unless stimulated by cytokines, which can result in a higher level of expression (Foder et al., 1994, cited above).

Besides the promoters noted above, there are many others which are associated with genes that encode proteins expressed on the surface of endothelial cells. There is no consensus in the art as to which promoters are most suitable to achieve endothelial expression of a gene of interest, especially in transgenic animals.

Yet another approach to the delivery of C-inhibitors to a transplantable organ was pioneered by Byrne et al., in PCT/US93/08889. Complement inhibitors were specifically expressed in the red blood cells of transgenic animals, which then transfer the proteins to the vascular endothelium of their organs and tissues. Once the organ of interest has been "painted" with complement inhibitor active in the intended recipient, the organ may be safely transplanted.

While this approach appears promising, it takes time to achieve full coverage of the vascular endothelium, so there is a delay before the organ can be used for transplantation. Additionally, once the donor tissue is harvested from the transgenic animal, replacement of the proteins on the surface of the donor tissue will not take place since the organ itself does not produce the protein. The organ would have to be routinely reperfused with the transgenic animal's blood in order to maintain high expression. Therefore, though this approach is promising it has certain limitations. For example, this approach could be beneficial in a situation where expression of the protein in the endothelial tissue is not possible or if it is used to supplement expression levels, which might prove to be beneficial in the first few weeks post-transplantation.

Thorley et al., *Transplant. Proc.*, 27:2177–78 (1995), reported the construction of a CD46 (membrane cofactor protein, MCP) mini-gene. The CD46 gene is more than 45 kb long, precluding the use of a full-length insert in a plasmid vector. The mini-gene was derived from genomic and cDNA sources. It was composed of 7.5 kb of genomic sequence, from 450 5' of exon 1 through to intron 3, and the cDNA sequence corresponding to exons 3–14. The minigene was used in the preparation of transgenic mice, however, the pattern of expression of the gene in those mice was not determined.

Accordingly, no satisfactory method has been developed wherein a transgenic animal is produced which expresses a gene for a complement inhibiting protein at a level suitable so that the organs and tissues of the transgenic animals can be useful in xenotransplantation with reduced or eliminated hyperacute rejection. Moreover, no one DNA construct has been manufactured which contains multiple complement inhibitor genes in the same locus that can be used to counteract the problems of hyperacute rejection that occurs following xenotransplantation from distantly related species such as from pig to man.

In addition, as indicated above, other recent studies have now indicated that antibody-mediated rejection, including hyperacute rejection, is initiated by the binding of xenoreactive natural antibodies (or XNAs) to the carbohydrate structures present on the endothelial cells of the graft which leads to the activation of the complement cascade. See Platt et al., *Transplantation* 50:817–822 (1990). It has thus been shown that the predominant carbohydrate epitope on the xenograft which is recognized by XNAs and thus primarily responsible for antibody-mediated rejection is galactose ($\alpha$1,3) galactose, also called the gal epitope or Gal$\alpha$(1,3)Gal. See, e.g., Sandrin et al., *P.N.A.S.* 5 90:11391–11395 (1993) and *Transplantation Reviews*, 8:134–149 (1994). This epitope is absent in primates, Old World monkeys and humans. See Good et al, *Transplant Proc.* 24:559–562 (1992) and Galili et al., *P.N.A.S.* 84:1369–1373 (1987). It is believed that the gal epitope is synthesized in the trans-Golgi by the enzyme Gal$\beta$1,4GlcNAc3-$\alpha$-D-galactosyltransferase (or "$\alpha$(1,3)GT"; EC 2.4.1.51) which catalyzes the addition of galactose to a N-acetyllactosamine (N-lac) core. See Blanken et al., *J. Biol. Chem.* 260:12927–12934 (1985). Humans, like apes and other Old World monkeys, do not have the gal epitope due to a lack of a functional $\alpha$(1,3)GT gene, as shown for example in Galili et al., *J. Biol. Chem.* 263:17755–17762 (1988) and Larsen et al., *J. Biol. Chem.* 265:7055–7061 (1990).

Given the specificity of XNAs and previous studies demonstrating that certain aspects of antibody-mediated rejection such as HAR could be delayed by depletion of these antibodies, researchers in this field have attempted to develop ways of achieving non-human donor tissue which lacks the gal epitope, or which has significantly reduced levels of this epitope, such that this tissue will not lead to HAR when transplanted into a human patient. However, the development of an adequate and effective method of achieving reduction of the gal epitope, to allow the production of tissue suitable for xenotransplantation, has proven to be a difficult task because of the complexities surrounding the enzymatic pathways leading to the production of the carbohydrate epitopes in xenogeneic tissues.

For example, the Gal$\beta$ 2-$\alpha$-L-fucosyltransferase (also known as $\alpha$(1,2)fucosyltransferase or "$\alpha$(1,2)FT"; EC 2.4.1.69) enzyme is involved in the formation of the Fuc$\alpha$1, 2Gal$\beta$- epitope (also known as the H antigen), the characteristic structure of the blood group "O" which is universally accepted in human patients and which is the precursor molecule in the human ABO blood group system. One of the substrate molecules for $\alpha$(1,2)FT is N-lac, which is also utilized by $\alpha$(1,3)GT as an acceptor of galactose, see Lowe, *Semin. Cell Biol.* 2:289–307 (1991) and Paulson et al., *J. Biol. Chem.* 264:17615–17618 (1989). In vitro substrate specificity studies have shown that fucosylated (or sialated) N-lac is a poor substrate for $\alpha$(1,3)GT. See Blanken et al., *J. Biol. Chem.* 260:12927–12934 (1985). However, although there are several fucosyltransferases that are known, the differences in the enzymatic pathways for each enzyme makes it somewhat unpredictable as to how any individual enzyme will perform when expressed in xenogeneic tissues.

Another glycosyltransferase which also uses N-lac as an acceptor is $\beta$-galactoside $\alpha$(2,6)sialyltransferase (also known as $\alpha$(2,6)sialyltransferase or "$\alpha$(2,6)ST"; EC 2.4.99.1) which transfers sialic acid residues to N-linked carbohydrate groups of glycoproteins, See, e.g., Lowe, *Semin. Cell Biol.* 2:289–307 (1991). The enzyme $\alpha$(2,6)ST is expressed in human endothelial cells, B cells, etc., and therefore should not be antigenic. See Dorken et al., in *Leukocyte Typing IV, White Cell Differentiation Antigens*, Knapp et al., eds., Oxford University Press, pp. 109–110 (1989) and Hanasaki et al., *J. Biol. Chem.* 269:10637–10643 (1994). In fact, due to its negative charge, sialic acid has sometimes been shown to inhibit activity of the alternative pathway of human complement. See Fearon, *P.N.A.S.* 75:1971–1975 (1978). However, once again, there is great variance among sialyltransferases, and the effectiveness of any particular sialyltransferase may vary from one to another.

Still another of the glycosyltransferases that may be involved in pathways that may compete with the $\alpha$(1,3)GT enzymatic pathways is $\beta$1,3 N-acetylglucosaminyltransferase (or "$\beta$(1,3)NAGT"), which is described in Kornfield et al., *Ann. Rev. Biochem.* 54:631–664 (1985). However, the complex enzymatic pathways associated with $\beta$(1,3)NAGT are far from clear, and it has not been disclosed or suggested that such an enzyme would be useful in a method of reducing the level of the gal epitope in xenogeneic donor tissue, organs, cells or non-viable components that would be useful in xenotransplantation.

Moreover, it has still not been previously shown that the expression of any other glycosyltransferase, such as human $\alpha$(1,2)FT or $\alpha$(2,6)ST, in transgenic animals such as pigs and mice can produce suitable antigens on endothelial cells of multiple organs so as to achieve a reduction in XNA binding (and subsequent complement activation) and allow large scale production of usable donor tissue and organs from transgenic animals which will have reduced or eliminated antibody-mediated rejection when transplanted into human patients. Additionally, previous researchers have deemed it unlikely that techniques involving use of sugar structures such as sialyltransferase or fucosyltransferase to produce transgenic animals with altered expression of the gal epitope which would be useful in xenotransplantation. See Cooper et al., *Immunological Reviews* 141:31–57 (1994). Again, due to the complexity of the sialyltransferases and fucosyltransferases and the substantial differences between individual members of these groups (see, e.g., Kitagawa et al., *J. Biol. Chem.*, 269:17872–17878, 1994), the potential usefulness of any particular members of these groups has remained uncertain and unpredictable, and indeed many of these enzymes may be undesirable for xenotransplantation.

In addition, it has not been shown that a transgenic animal can be prepared which expresses multiple types of genes which can effectively mask or reduce the level of the antigenic gal epitope while at the same time reduce the possibility or likelihood of activating the complement cascade following xenotransplantation. Similarly, it has also not been previously shown that a gene for a complement inhibitor can be used in combination with a gene that masks or reduces the level of the gal epitope so as to produce transgenic animals suitable for use in transplantation. Finally, it has not previously been accomplished to place multiple genes on a single DNA construct which can be transfected into a donor animal and expressed so as to provide an increased level of protection against antibody-mediated rejection when organs, tissues, cells or non-viable components from the donor animal are transplanted into a human patient.

SUMMARY OF THE INVENTION

It is thus an object of the present invention to develop transgenic animals such as pigs (or mice) which express both an enzyme capable of masking or reducing the level of the xenoreactive antigens, such as gal epitope, and a complement inhibitor, and which thus can achieve a decrease in both the level of the antigenic gal epitope and subsequent complement activation caused by transplantation of organs, tissues, cells or non-viable components from these transgenic animals.

It is also an object of the present invention to provide transgenic animals that are useful in xenotransplantation because of their ability to achieve substantial reductions in both XNA binding and subsequent complement activation following transplantation, and thus reduce or prevent antibody-mediated rejections, such as hyperacute rejection, and complement-mediated rejection when transplanted into human patients.

It is also an object of the present invention to provide methods for obtaining transgenic animals which express at least one enzyme, including but not limited to $\alpha(1,2)$ fucosyltransferase, $\alpha(2,6)$sialyltransferase, $\beta(1,3)$ N-acetylglucosaminyltransferase, or other suitable glycosyltransferase which is capable of masking or reducing the level of the gal epitope as well as at least one complement inhibitor, including but not limited to CD59, DAF and/or MCP, along with methods for effecting xenotransplantation which utilize donor organs, tissues, cells or non-viable components from transgenic animals produced by the present invention so as to reduce or eliminate antibody-mediated or complement-mediated rejection in human transplant recipients.

It is further an object of the present invention to provide methods for obtaining an ample supply of suitable donor organs, tissues, cells or non-viable components which have masked or reduced levels of the gal epitope, and which will be less likely to produce antibody-mediated rejection when transplanted into a human patient, by producing transgenic animals which can express glycotransferases or other suitable enzymes capable of masking or reducing the level of the gal epitope in endothelial cells.

It is still further an object of the present invention to provide xenogeneic organs, tissues, cells or non-viable components which express both at least one enzyme capable of masking or reducing the level of the gal epitope, including but not limited to enzymes such as $\alpha(1,2)$FT, $\alpha(2,6)$ST or $\beta(1,3)$NAGT, along with at least one gene coding for a complement inhibitor, including but not limited to CD59, DAF, and/or MCP, which thus have a masked or reduced level of the Gal$\alpha(1,3)$Gal epitope and a greatly reduced likelihood of causing antibody-mediated or complement-mediated rejection following transplantation into human patients.

It is still further an object of the present invention to produce transgenic pigs that express nucleic acid constructs coding for a multiple gene locus coding for two or more complement inhibitor proteins, and which preferably express high levels of all of these complement inhibitors.

It is still further an object of the present invention to provide in a single DNA construct nucleic acid coding for at least one enzyme capable of masking or reducing the level of the gal epitope, including but not limited to $\alpha(1,2)$ fucosyltransferase, $\alpha(2,6)$sialyltransferase, or $\beta(1,3)$ N-acetylglucosaminyltransferase, and at least one complement inhibitor, including but not limited to CD59, DAF and/or MCP, and methods for producing transgenic animals that can express this DNA construct that will be useful in providing donor organs, tissues, cells or non-viable components for transplantation into humans.

These and other objects of the present invention are achieved in the present invention by the production of transgenic animals that express both at least one enzyme which masks or reduces the level of the antigenic Gal$\alpha(1,3)$Gal or gal epitope, including but not limited to glycosyltransferases such as $\alpha(1,2)$fucosyltransferase ("$\alpha(1,2)$FT"), $\alpha(2,6)$sialyltransferase ("$\alpha(2,6)$ST"), and/or $\beta(1,3)$N-acetylglucosaminyltransferase ("$\beta(1,3)$NAGT"), along with at least one complement inhibiting protein, including but not limited to proteins such as CD59, DAF and/or MCP. The transgenic animals produced in accordance with the invention thus express at least one enzyme which competes with the enzyme $\alpha(1,3)$galactosyltransferase to thereby mask or reduce the production of the gal epitope which otherwise would be recognized by the xenoreactive natural antibodies (XNAS) in humans and thus lead to antibody-mediated rejection.

In addition, in accordance with the present invention, a transgenic animal is provided which expresses nucleic acid constructs coding for a plurality of complement inhibitors such as a three gene locus of complement inhibitor proteins, and which preferably express high levels of all three of these complement inhibitors. By the construction of transgenic animals in accordance with this aspect of the invention, donor organs, tissues, cells and non-viable components can be obtained from these transgenic animals which express complement regulatory proteins that act to suppress the activation of complement that would occur after recognition of the foreign tissue by XNAs, and the resulting immune rejection following their transplantation into humans will be greatly reduced or eliminated.

Accordingly, the method of the present invention will thus be useful in providing xenogeneic organs, tissues, cells and non-viable components which can be transplanted safely and effectively into humans and which will thus reduce or eliminate the need to obtain organs, tissues, cells and non-viable components from human or primate donors. In addition, the present invention provides in a single DNA construct a multiple locus of complement-inhibiting proteins which can also be prepared to include nucleic acid coding for both an enzyme capable of masking or reducing the level of the gal epitope, as will be described in or will be obvious from the detailed description of the invention provided below.

BRIEF DESCRIPTION OF THE DRAWINGS

The present invention will now be described in detail with respect to preferred embodiments thereof, which are to be taken together with the accompanying drawings, wherein:

FIG. 10 is an SDS-PAGE representation of UEA-I and GS-1-$B_4$ lectin binding to the membrane glycoproteins of CHO-N cells, CHO/GT cells and CHO/GTFT cells as resolved by SDS-PAGE (8% gel) and transferred to a membrane;

DETAILED DESCRIPTION OF THE PREFERRED EMBODIMENTS

Figure 1:
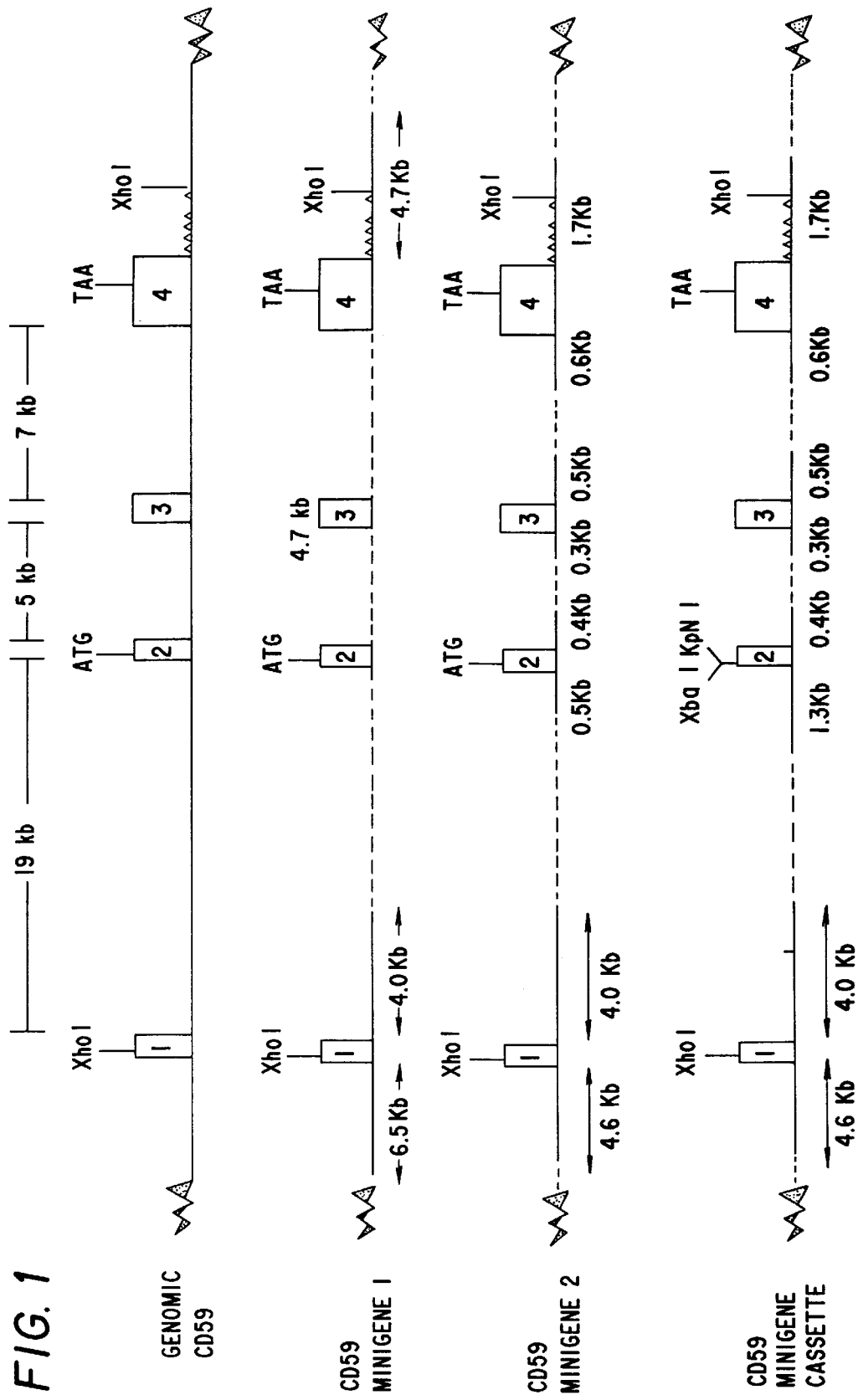
FIG. 1 relates to the Construction of CD59 Minigenes in accordance with the invention. The genomic structure of the human CD59 gene locus is shown as the top figure. Below are the two CD59 minigenes constructed (CD59 Minigene 1 and CD59 Minigene 2) and the CD59 Minigene Cassette, which is based upon CD59 Minigene 2. Dotted lines represent sequences in the human gene which are omitted from each minigene construct. Below each minigene construct is indicated how many kilobases of the respective portions of the CD59 gene are present in each portion of the minigene.

In accordance with the present invention, a method is provided for xenotransplanting organs, tissues, cells or non-viable components into human patients which reduces or prevents antibody-mediated rejections, such as hyperacute rejection, as well as complement-mediated rejection, and this method preferably comprises the production of transgenic animals that express at least one enzyme capable of reducing the level of xenoreactive antigens, such as the antigenic gal epitope, including but not limited to glycosyltransferases such as $\alpha$(1,2)fucosyltransferase ("$\alpha$(1,2)FT"), $\alpha$(2,6)sialyl-transferase ("$\alpha$(2,6)ST"), and/or $\beta$(1,3)N-acetylglucosaminyl-transferase ("$\alpha$(1,3)NAGT"), and at least one complement inhibiting protein, including but not limited to CD59, DAF and/or MCP. In addition, the present invention includes a method of utilizing the transgenic animals so produced in order to provide a plentiful supply of suitable donor organs, tissues, cells and non-viable components which can be useful in methods of xenotransplantation with reduced or eliminated immune system rejections in the host.

The present invention has been developed so as to overcome the previous problems associated with xenotransplantation caused by the binding of xenoreactive natural antibodies (XNAs) in the recipient of the donor tissue and subsequent complement activation and to provide a plentiful supply of suitable donor organs, tissues, cells and non-viable components that will be useful in xenotransplantation with reduced or eliminated antibody-mediated rejection. In particular, the present inventors have determined that specific enzymes which can compete with the $\alpha$(1,3)GT enzyme, including $\alpha$(1,2)FT, $\alpha$(2,6)ST, and/or $\beta$(1,3)NAGT, can be useful in masking or reducing the level of the gal epitope in organs, tissues, cells and non-viable components expressing these specific enzymes. In addition, despite the fact that it has previously been deemed desirable to employ complement inhibiting proteins in attempts to reduce or avoid the severe immune response that occurs following xenotransplantation, prior methods have previously been ineffective in providing a suitable mode that was capable of expressing sufficient levels of the complement inhibitors in endothelial cells in order to achieve significant reductions in complement activation and reduce the antibody- and complement-mediated rejection following tissue implantation. In particular, the previous attempts to use C-inhibitors on endothelial cells have been unable to maintain a consistent, high level of expression of the complement inhibitors in the endothelial cells of the donor organ.

In the present invention, Applicants have now for the first time prepared transgenic animals and DNA constructs that contain at the same integration site nucleic acid coding for at least one enzyme capable of reducing the level of the antigenic gal epitope in endothelial cells and at least one complement inhibitor protein or complement regulatory protein. In particular, this can be accomplished by means of a Yeast Artificial Chromosome (or YAC) which in the particularly preferred embodiment can constitute a large piece of DNA containing a plurality of genes coding for enzymes capable of reducing the level of the gal epitope along with genes coding for a plurality of complement inhibiting proteins. By use of the YACs of the present invention, a distinct advantage is obtained because the multiple genes coding for the desired enzyme or enzymes are combined with the multiple genes coding for the desired complement inhibiting proteins, and a single DNA construct can be obtained which codes for all of the desired enzymes and proteins.

The YACs are thus preferably engineered to comprise a plurality of inhibitor genes. By putting all of the genes on a single YAC, it is assured that all genes integrate at the same site in a manner not obtained previously, and these genes will not segregate away from each other upon breeding. YACs are used because of their high insert capacity relative to other conventional cloning vectors. The use of these large YACs in accordance with the invention will greatly improve the efficiency in obtaining suitable transgenic animals since it will only be necessary to transfect this single YAC construct into a desired animal in order to obtain expression of the two desired types of proteins, particularly the desired enzymes and complement inhibiting proteins discussed above, and produce transgenic animals far more suitable for xenotransplantation than any transgenic animals previously obtained.

In another preferred embodiment of the present invention, the desired genes are prepared in the form of minigenes which may include all of the desired genes on one construct, or wherein a plurality of minigenes are constructed, at least some of which contain nucleic acid coding for at least one specific desired enzyme capable of reducing or masking the level of the gal epitope, and some of which contain nucleic acid coding for at least one desired complement inhibitory protein. In this latter case, at least one minigene coding for at least one enzyme capable of reducing the level of the gal epitope is transfected along with at least one minigene coding for at least one complement inhibitor so that the resulting transgenic animal will express both the desired enzyme and the desired complement inhibitor in accordance with the present invention.

In still another process of the present invention, a construct in the form of bacteriophage P1 clones is also employed. In the preferred embodiment, CD59 P1 clones (and other complement regulatory protein P1 clones) can be produced which ideally contain the full genomic regulatory system for CD59, MCP and DAF and therefore may prove useful, either directly or as a source of genetic material. Because of the size of the construct, the expression of the CD59 gene in the P1 construct is less likely to be influenced by the site of integration, the distal portions of the insert acting as a buffer.

In the preferred processes described above which are suitable for use in producing transgenic animals in accordance with the present invention, high expression of one or more human complement regulatory proteins, including but not limited to CD59, DAF and/or MCP, is achieved at all times so that in the endothelium of the donor organ in combination with the expression of an enzyme reducing the level of the gal epitope that can reduce or prevent the onset of antibody- or complement-mediated rejections, including hyperacute rejection. It is preferred that these expression vectors contain at least one complement inhibiting protein, such as CD59, MCP or DAF, but in the particularly preferred construct, a plurality of complement inhibitors are employed in a single clone. These animals had high, constitutive levels of expression of the complement inhibitors in endothelial cells, and have accordingly achieved a reduction in the observed hyperacute rejection. As will be set forth below, in addition, nucleic acid constructs formed in accordance with the present invention which express one or more complement inhibiting proteins may be combined with nucleic acid constructs that express enzymes capable of reducing the level of the gal epitope in the endothelial cells of both transgenic mice and transgenic pigs.

The present invention thus relates to the expression of proteins, including but not limited to glycosyltransferase enzymes such as $\alpha(1,2)$FT, $\alpha(2,6)$ST and $\beta(1,3)$NAGT, which mask or reduce the level of the antigenic Gal$\alpha(1,3)$Gal or gal epitope, along with the expression of a complement inhibiting protein, including but not limited to CD59, DAF, MCP and/or additional complement inhibitors as described herein, on the surface of endothelial cells of transgenic animals which have been genetically engineered or bred to contain genes producing these proteins and enzymes.

As indicated above, one preferred aspect of the invention is the preparation and use of a minigene to express at least one complement-inhibiting protein, including but not limited to CD59, DAF and/or MCP, along with an enzyme which reduces the level of the antigenic gal epitope on the surface of endothelial cells. In the preparation of the transgenic animals of the invention, it is preferred that nucleic acid such as DNA coding which codes for an enzyme reducing or masking the level of the antigenic Gal$\alpha(1,3)$Gal or gal epitope, is incorporated into a single nucleic acid construct, such as in the form of a minigene, that also includes nucleic acid coding for at least one complement inhibitor protein such as CD59, and/or other complement inhibitors including DAF and MCP, as will be described below. Alternatively, separate minigenes coding on one hand for the enzyme capable of reducing the level of the gal epitope, and for one or more complement inhibiting proteins on the other, may also be prepared, and in this mode of the invention, the two types of minigenes can be co-injected into the transgenic animal so as to obtain offspring which will possess both of the desired types of genes in accordance with the invention. The construction of the minigenes of the present invention will now be described in more detail.

A. THE CD59 MINI-GENES

A coding sequence is a sequence which, under appropriate conditions, is transcribed into a messenger RNA and translated into a polypeptide. Because of the degeneracy of the genetic code, there are many different DNA sequences which encode the same polypeptide, all of which are considered coding sequences therefor. The term "coding sequence" is also used, mutatis mutandis, to apply to a DNA sequence which is transcribed into an "antisense RNA", which is merely a messenger RNA transcript which is expected to hybridize to a target messenger RNA and thereby inhibit the translation of the target message into a polypeptide. It is not necessary that the "antisense RNA" be translated into a polypeptide.

One may also define "regulatory sequences" which affect the transcription and translation of coding sequences. The promoter is a regulatory region which lies 5' (upstream of the coding sequence, and contains the site to which the DNA-directed RNA polymerase binds, thereby initiating transcription. The term "promoter" is often used to refer, not only to that binding site, but also to a complex of regulatory elements 5' of the coding sequence, often including elements which determine the circumstances under which the coding sequence is expressed. The regulatory DNA may also include sequences which lie 3' of the coding sequence, such as "terminators".

In the mammalian genome, the coding sequence of certain genes is interrupted by noncoding sequences, called "intervening sequences" or "introns". The coding sequence is then said to be divided into a plurality of "exons". The genomic DNA of such a gene is transcribed into a pre-messenger RNA, which is then processed to remove the introns to yield a mature RNA transcript. The latter is then translated into a polypeptide. In certain genes, the introns contain regulatory elements which can affect the transcription or translation of the gene. See, e.g., Laherty et al., *J. Biol. Chem.*, 264:11222–27 (1989), reporting that removal of the first intron of the human thrombospondin gene resulted in a four-fold loss in transcriptional activity.

If a complete gene is isolated directly from the genome, it will include the introns, if any. A coding sequence may, however, be obtained by isolating the mature messenger RNA from the cell and then synthesizing a complementary DNA (cDNA). The coding sequence of a cDNA will not be interrupted by introns.

A mini-gene is a gene which differs from the authentic genomic sequence in that at least part of one or more introns is deleted, but differs from a corresponding cDNA in that it possesses at least part of one or more introns. A mini-gene may be constructed by deleting genetic material from a genomic fragment, by inserting genetic material into a cDNA, or by direct synthesis.

The structure of the CD59 gene is described in Petranka et al., *Proc. Nat. Acad. Sci.* (*USA*) 89:7876–79 (1992) and 90:5878 (1993), as well as PCT Application WO 96/12804 issued to Imutran Limited. It comprises four exons spanning about 20 kb. The first exon is 45 bp in length and is entirely untranslated. It is separated from exon 2 by an intron, originally stated to be 5.4 kb, but later determined to be 19 kl. Exon 2 is 85 bp long and contains an 18 bp untranslated region followed by the sequence coding for most of the hydrophobic signal sequence of the protein. Exons 2 and 3 are separated by an intron of about 5 kb. Exon 3 is 102 bp in length and encodes the remainder of the leader sequence and the first 31 amino acids of the mature protein. Exon 4 begins after an intron of 7 kb. Exon 4 includes the remainder of the translated sequence as well as at least 1438 bp of UT sequence.

Construction of a CD59 minigene was undertaken to address deficiencies inherent to use of cDNAs driven by heterologous promoters in transgenic animals. The general observation with such constructs has been inconsistent expression of the transgene among transgenic animal lines derived as well as a tissue and cell type expression which does not match that seen with the endogenous gene. In addition, levels of transgene expression are not often optimal. It was deduced that use of a homologous promoter would overcome these problems. The regions of the CRPs which are necessary and sufficient to direct appropriate expression of the respective genes in terms of level and tissue/cell type specificity have not been publicly disclosed. Additionally, each of the genes thus far mapped are very large, at least 40 Kb. Therefore construction of a CD59 minigene was undertaken. CD59 was chosen as a prototype for several reasons. CD59 is the simplest of the C-inhibitor genes in that it has only 4 exons (as compared to 11 exons in DAF and 14 exons in MCP). CD59 uses alternative polyadenylation sites but does not seem to utilize differential splicing. Transcription of MCP and DAF genes gives rise to several RNA isoforms due to differential splicing, making it difficult to choose which exons to include in a final construct. In addition, CD59 is expressed at high levels in all of the relevant cell types in which we were interested whereas MCP, for instance, is not.

Several considerations contributed to the design of the CD59 Minigene 1. In order to exploit the possibilities of co-integration of two or more minigenes or minigene cassettes, it was important to limit the size of the CD59 Minigene. It was decided that the majority of intron sequences could be dispensed of, keeping intact a portion (4.5 kb) of intron 1 to allow for splicing. Usually at least one splice site is important for efficient transgene expression. Intron 1 was chosen because exon 1 is a noncoding exon and intron 1 is Intron 1 was considered the most likely intron to be important for regulation of gene expression, because of its conservation of such a large, noncoding region of a gene may be selected for because it is functional in some aspect, i.e., gene regulation.

The promoter sequences responsible for gene expression have not been defined and analysis of the region of the gene 5' of the transcriptional start site did not reveal any transcription factor binding sites except for two Spl sites immediately upstream of the transcriptional start site. region of 6.5 Kb was chosen to use as the promoter sequence based upon experience that, in general, a region of that size should be large enough to encompass gene regulatory regions, but not so large that it also contains regulatory regions for a gene which could exist 5' of CD59 and may be configured in a head-to-head orientation with CD59. If such were to occur, one could experience interference of regulation of gene expression.

Approximately 4.7 Kb of the 3' untranslated sequence was included in the CD59 Minigene 1 to ensure that four of the five polyadenylation sites were present. The fifth site, which is used at a relatively low frequency, is unmapped but is at least 3 Kb further downstream than the most frequently used site. It has been shown in some genes that the 3' untranslated region contains sequences which confer stability to the mRNA and if this was the case with CD59 it was felt that 4.7 Kb should encompass such a region.

The coding region of CD59 was inserted into the construct as a cDNA with a synthetic splice acceptor site added to the 5' of exon 2. This was the simplest approach since there was no way a priori to decide which, if any, of the remaining introns may exert an influence on regulation of gene expression.

In Mini-Gene 2, in order to address low levels of CD59 gene transcription, portions of endogenous introns were added to surround each exon. This would ensure that the branch point of the pre RNA, which is important for splicing, would be included at each splice acceptor site, as well as surrounding sequence which may be necessary to maintain secondary structure and binding sites for proteins required for splicing. In order to incorporate these regions, it was deduced that a minimum of 200 bp of intron both 5' and 3' of each exon should be included in a new minigene. However, the skilled worker may, in the light of the present specification, experiment with the inclusion of a lesser or a greater amount of the proximal portions of the introns. The amount retained at the 3' and 5' end of each intron may be the same or different, and may vary from intron to intron.

The 3' untranslated region of CD59 Minigene 2 was reduced from 4.7 Kb to 1.7 Kb. As mentioned previously, we were interested in keeping the size of the minigene to a minimum and 1.7 Kb encompassed the four most frequently used polyadenylation sites. In addition, while a larger 3' region was used in CD59 Minigene 1 to include possible stabilizing sequence, the possibility also existed that destabilizing sequences resided in the 3' end of the gene. However, guided by the instant specification, the skilled worker in the art may test the effect of including a greater or lesser amount of the 3' region, or of deleting selected, neutral or destabilizing sequences within the 3' region and then joining formerly noncontiguous sequences of that region.

The 5' of the CD59 Minigene 2 was reduced from 6.5 Kb to 4.6 Kb based upon several observations. A communication from a colleague revealed that DNase I hypersensitive sites existed in the CD59 5' region fairly close to the transcriptional start site, indicating that this was the region necessary for transcriptional regulation and that additional sequence was unnecessary. As mentioned above, trimming the minigene to a minimum size is in our best interests in order to co-inject multiple genes. Secondly, it was observed that cloning of the 6.5 Kb 5' region used in CD59 Minigene 1 often resulted in rearrangements and deletions of the 5'-most region. There existed the possibility that this region was unstable and therefore undesirable as a transgene. Lastly, preliminary and later unsubstantiated data derived from analysis of 2 different genomic P1 clones indicated that a smaller 5' region of CD59 resulted in substantially higher levels of gene expression. Of course, as guided by this specification, the reader may experiment with the inclusion of greater or lesser amounts of the 5' region, and with the selective deletion of neutral or destabilizing regions thereof.

In order to utilize the CD59 Minigene 2 as an expression cassette, a number of changes were implemented. Firstly, it was found that attempts to convert CD59 Minigene 1 into an expression cassette by insertion of a CDNA into the Xho I site in the untranslated exon 1 were unsuccessful in that expression of inserted cDNAs was rare and if present it was extremely low. Further investigation into the promoter region led us to believe that this was because the CD59 promoter, being a TATA-less promoter, most likely utilized an initiator element, typically referred to as Inr, for binding of transcription elements. Inr's are usually located in very close proximity to the transcription start site. The Xho I site used as an insertion site is also very close to the transcription start site and so disrupting this region may have compromised transcription initiation. Additionally, the way the CD59 Minigene 1 construct was used an expression cassette left the CD59 coding region intact. This could cause competition for expression of CD59 versus the inserted CDNA.

To address the above, the ATG which encodes the initiating methionine in exon 2 was mutated and in its place two unique restriction enzyme sites, Kpn I and Xho I, were inserted. These sites serve as cloning sites to introduce any gene of interest. A second modification to CD59 Minigene 2 was based on an additional communication received from a colleague. It was revealed that a second DNase I hypersensitive site had been localized approximately 0.9 Kb upstream of exon 2. DNase I hypersensitive sites are often correlate with regions important in gene regulation. In order to include this potentially important region of DNA into the CD59 Minigene 2 cassette, an additional 0.83 Kb of DNA was added to the existing 0.5 Kb of intron 1 which was directly 5' of exon 2, to give a total of 1.3 Kb of intron sequence.

Several alterations to the Minigene 2 Cassette are possible. Some are outlined below.

A Different Promoter

The order of construction of the various pieces of DNA calls for the promoter element to be added as a last step. This enables different promoters to be interchanged with that of CD59. The reason for this is as follows. In some cases, timing of expression, for instance during fetal development, is crucial for a particular gene and if inappropriate may induce lethality. Therefore it may be important to use a different promoter for some genes in order to control their expression during development of the transgenic animal. Along the same lines, CD59 is expressed at high levels in RBCs. It may be detrimental for an animal to have certain other genes expressed in RBCs and therefore one would be creating a lethal construct. And so it may be important to have a promoter in the cassette which has a slightly different repertoire of cell and tissue type specificity. Preferred substitute promoters include the DAF and MCP promoters.

An Inducible Element

It may also be of interest to add an inducible element 5' of the transcription start site in order to control timing of expression on a different level. For instance, the span of time immediately after reperfusion of a xenograft which is crucial to the survival of the graft, one may which to "superinduce" CRP expression. An example of such would include an element responsive to gamma interferon, for instance. In addition, one could add a suppressor element with a "responder" element which is controlled by the suppress or element such that transcription would be in the off state at all times until the suppressor is lifted. An example of this scenario would be use of the tet repressor elements whereby expression is repressed by administration of tetracycline and repression is relieved by withdrawal of tetracycline.

Removal of Non Coding Sequence

Most likely removal of additional intron sequences is possible without affecting the expression levels or tissue and cell-type specificity of Minigene 2. This could be tested empirically by systematically removing each intron, keeping at least one intron intact to satisfy the general requirement that most transgenes appear to have in order to achieve efficient transcription. The resulting constructs could be assayed in tissue culture assuming that the CD59 promoter would function in most mouse fibroblast cell lines. If not, a generic promoter, such as the SV40 promoter/enhancer element, could be interchanged in order to test the necessity of each intron. Alternatively, each construct could be tested as a transgene in mice. A systematic promoter deletion analysis is also possible using the readout systems described above. Further deletion of the 3' region would probably impinge upon the polyadenylation site apparently in use which appears to be further 3' than the sites described in the literature, giving a mRNA of approximately 3.1 Kb as compared to the expected 1.9/2.1 Kb message. Reducing the size of the minigene and/or cassette to a minimum size while still retaining biological activity and appropriate expression is desirable in order to increase the likelihood of co-integration of minigene cassettes. On the other hand increasing the size of the minigene may be desirable in order to incorporate additional sequences which may improve expression. Preferably, the minigene is of a size of about 6 to 15 kb.

Addition of a Signal Sequence

Another potential modification to the CD59 Minigene 2 Cassette is addition of a signal sequence such that an inserted cDNA is secreted as opposed to expressed as a membrane protein. In addition, if desired, a GPI attachment signal may be added if the DNA encodes a non-GPI protein. See Byrne, PCT/US93/08889.

Basic procedures for constructing recombinant DNA and RNA molecules in accordance with the present invention are disclosed by Sambrook et al., *Molecular Cloning: A Laboratory Manual*, Second Edition, Cold Spring Harbor Press, Cold Spring Harbor, N.Y. (1999), and Ausubel et al., *Current Protocols in Molecular Biology*, Wiley Interscience (1995). See also Coligan, et al., *Current Protocols in Protein Science* (1995).

Complement Inhibitors

For xenotransplantation, the proteins of greatest interest are normally "complement inhibitors". In all species with a complement lysis system there are a variety of molecules which normally function to inhibit complement, and these complement inhibitors appear necessary to limit autologous cell lysis within the host. Some of the complement inhibitors are species specific, i.e., a human complement inhibitor such as DAF will inhibit human complement and complement of some closely related primate species, but is ineffective against complement of more distant species such as the mouse or pig. Indeed this form of species-specific complement inhibition is thought to be one of the major contributory factors in determining whether or not a xenograft is concordant or discordant.

Accordingly, any of the proteins which are determined to possess complement inhibitory activity are suitable for use in the mini-genes of the present invention. In particular, at least three of the human complement inhibitors, DAF, MCP and CD59, are of interest because they are all thought to function solely to protect host cells from complement-mediated cell lysis. See Kinoshita, *Immunol. Today* 12:291–295, (1991). These molecules inhibit complement by interfering with C3 and C5 convertase (MCP and DAF) or by preventing formation of the terminal membrane attack complex (CD59). However, as stated above, the present invention is not limited to DAF, MCP, and CD59, and extends to any of the complement inhibiting proteins, including but not limited to: Factor I, Factor H, C4 binding protein (or C4bp), CR1, CR2, C8 binding protein, HRF, MIP, P-18, HRF-20 and MIRL.

Most or all of these molecules are found on red blood cells and endothelial cells and are anchored to the cellular surface through a glycosylphosphatidylinositol (GPI) linkage. At the protein level all three complement-inhibitors are broadly distributed, and generally are found in any region which is in contact with complement activity.

Complementary DNAs corresponding to CR1, CR2, DAF, MCP, C4bp and Factor H have been cloned and sequenced, as a result of which it is known that these proteins are composed mainly of a tandemly repeated motif of about 60–70 amino acids in length, called "short consensus repeats" (SCRS). Several pathogens carry genes encoding structurally related proteins. The 35k vaccinia protein has a signal sequence followed by four SCRs, and is 38% homologous at the amino acid level to the amino terminal half of C4 bp. The glycoprotein C-1 of HSV lacks a typical SCR structure, but nonetheless contains short stretches substantially homologous to various C-inhibitors and exhibits DAF-like activity.

For DAF sequences, see Medof et al., *Proc. Nat. Acad. Sci. USA*, 84: 2007–11 (1987); Caras et al., *Nature*, 325: 545–9 (1987). For MCP sequences, see Purcell et al., *Immunogenetics*, 33: 335–344 (1991). The CD59 sequence was previously discussed.

The present invention may also be used to express any protein which it would be advantageous to express in the endothelial cells of a genetically engineered animal, and it thus may be desirable to express additional proteins, other than complement inhibitors and the genes coding for enzymes reducing or masking the gal epitope as described above, using the CD59 minigene cassette. In the preferred mode of the invention, as will be described further below, the additional protein expressed on the minigene as prepared above, which will already contain a gene coding for a complement inhibitor, is an enzyme which is capable of masking or reducing the level of the gal epitope in the cells of the transgenic animals expressing this minigene. In general, however, any suitable protein which would be advantageously expressed in the endothelial cells of a transgenic animal is contemplated in the present invention, and such proteins would be incorporated into the above minigene using techniques such as those discussed above.

One class of such proteins useful in the present invention, generically referred to as immunomodulators, may include transforming growth factor-β (TGF-β), Nuclear Factor Kappa b ($NF_K b$) inhibitors, Interleukin-4 (IL-4), IL-10, or IL-12. These molecules affect immune cell development. Another class of proteins, referred to as regulators of thrombosis or anti-coagulants, include antithrombin III, tissue plasminogen activator (TPA), urokinase plasminogen activator (UPA), thrombomodulin, or tissue factor inhibitor. A third class of proteins one may be interested in expressing belong to a group described an anti-inflammatory proteins. An example of such a protein one might want to induce in prostaglandin $E_2$ and the enzyme responsible for its synthesis, prostaglandin synthase, could be expressed locally via a CD59 minigene cassette. Many of these proteins are not membrane-bound but are secreted. One would not be limited to membrane-bound proteins using the CD59 minigene cassette since the signal for secretion can be incorporated as part of the inserted gene of interest.

Mutants

The proteins used in the present invention, for example in the mini-genes constructed in accordance with the invention, may be naturally occurring proteins, including any allelic form of such proteins, or may be mutant versions which possesses the desired biological activity, although not necessarily to the same extent as the native protein.

The amino acid sequence of a protein of interest may be modified, e.g., by site-specific or semi-random mutagenesis of the corresponding gene to obtain a mutant protein with a "substantially corresponding" amino acid sequence.

In determining whether sequences should be deemed to "substantially correspond", one should consider the following issues: the degree of sequence similarity when the sequences are aligned for best fit according to standard algorithms, the similarity in the connectivity patterns of any crosslinks (e.g., disulfide bonds), the degree to which the proteins have similar three-dimensional structures, as indicated by, e.g., X-ray diffraction analysis or NMR, and the degree to which the sequenced proteins have similar biological activity. In this context, it should be noted that among the serine protease inhibitors, there are families of proteins recognized to be homologous in which there are pairs of members with as little as 30% sequence homology.

Preferably, the sequence of the mature protein is at least 50% identical, more preferably at least 80% identical, with the sequence of its naturally occurring cognate.

The 3D-structure can be used to identify interior and surface residues; generally speaking, proteins mutated at surface residues (other than the receptor binding site) are more likely to remain functional. However, Creighton et al., Nature, 339:14 (1989) discuss the toleration of mutations at buried residues. The structure may also be used to determine flexible surface "loops" and interdomain boundaries; proteins are more tolerant of deletions and insertions in such regions. In general, segments of the protein which are more difficult to resolve by NMR are likely to be segments which are freer to move, and hence more tolerant of mutation.

Insertions and deletions are preferably at the amino or carboxy termini, at loops (sequences joining helices to helices, helices to sheets, and sheets to sheets, and at interdomain boundaries). At termini, internal insertions or deletions are preferably of no more than three consecutive amino acids, more preferably only of a single amino acid.

The mutations are preferably substitutions. In terms of the kinds of substitutions which may be made, one may look to analyses of the frequencies of amino acid changes between homologous proteins of different organisms. Based on such analyses, we define conservative substitutions as exchanges within the groups set forth below:

I small aliphatic, nonpolar or slightly polar residues—Ala, Ser, Thr (Pro, Gly)

II negatively charged residues and their amides—Asn Asp Glu Gln

III positively charged residues—His Arg Lys

IV large aliphatic nonpolar residues—Met Leu Ile Val (Cys)

V large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding; the four cysteines of bGH are highly conserved. Some authorities would merge I and II above. Note also that Tyr, because of its hydrogen bonding potential, has some kinship with Ser, Thr, etc.

Acceptable substitutions also include substitutions already known, as a result of their appearance in proteins similar in biological activity and sequence with a protein of interest, to be likely to be tolerated. For example, if the protein of interest were to have superoxide dismutase activity, instead of using a protein identical with a naturally occurring SOD, it could be a chimera of several naturally occurring SODs.

In the case of proteins which are naturally GPI linked, mutations which could prevent attachment of the GPI anchor, as well as mutations which reduce the desired activity, should be avoided. The active site residues may be determined, if not already known, by methodically testing fragments for activity, as was done for C4bp by Chung and Reid (1985), or by systematic testing of mutants.

The nucleotide sequence which encodes the protein of interest may be, but need not be, identical to the naturally occurring sequence. "Silent" mutations may be made to improve transcriptional or transitional efficiency, introduce or eliminate restriction sites, or reduce the probability of recombination. In addition, mutations which result in a change in the encoded amino acid sequence may be made as previously discussed.

The sites at which mutations, especially conservative ones, are most likely to be tolerated may be determined by a combination of theoretical and experimental methods.

In general, residues can be classified as being either surface or interior residues. The location of residues can be determined experimentally by techniques such as X-ray diffraction or affinity labeling. If a homologous protein has a known 3D structure, it is possible to construct a model of the protein of interest using the homologous protein as a guide. If all else fails, locations may also be predicted on the basis of the hydrophilicity of the residue, with charged residues being especially likely to lie on the surface.

Most residues of a protein can tolerate some degree of mutation. A protein may be modified at an interior residue, a surface residue distant from the binding site of interest, or at a surface residue which is part of, or close enough to affect, the binding site of interest.

Modification of an interior residue is unlikely to affect the binding activity unless it interferes with the proper folding of a protein, specific and thus, indirectly, with the proper presentation of the binding surface. Generally speaking, mutation of internal glycines is undesirable because they may be needed to impart local flexibility to the polypeptide chain. Mutation of cysteines is usually detrimental because they often participate in disulfide bonds needed to hold the protein in a particular conformation. In general, it is best to refrain from replacing an interior residue with one that is substantially larger or more hydrophilic than the original residue. None of these rules are ironclad, however.

Generally speaking, the stability of a protein is more likely to be affected by the mutation of an interior residue than by the mutation of a surface residue.

Some surface residues will belong to a binding site, and the mutation of these residues will be more likely to affect binding activity, favorably or unfavorably. Binding sites may be identified in a variety of ways, including the systematic testing of fragments, or of single substitution mutants, for binding activity, or by forming the complex and then affinity labeling residues not occluded by the complex.

When homologous proteins are known, positions likely to be tolerant of mutation may be identified by determining which residue positions show the greatest variation within the family of homologous proteins. (Homologous proteins may be identified by computerized comparisons of the reference sequence to other sequences in a sequence databank.) In the case of GPI-linked proteins, mutations should be chosen to avoid inactivating the GPI attachment signals. The attachment signal of one protein may be substituted for that of another. Chimeric signals may also be constructed.

With regard to the complement inhibiting proteins discussed above, in the case of DAF and MCP, for example, it is likely that the SCRs are important to activity, and it is safer to mutate the non-SCR regions. If the SCRs are to be mutated, it is safer to mutate those residues which show the greatest variation among the SCRs found in the protein of interest, and to prefer substitutions corresponding to the observed variations.

With regard to CD59, human CD59 may be compared to its homologues in other mammalian species. Mutation of the more highly variable codons is preferred. However, to the extent that CD59 is species-specific, such mutations could result in change in the species specificity of the mutated protein and should therefore be made with caution. This warning must be qualified in that the species specificity of CD59s is uncertain and perhaps variable. According to Van Den Berg et al., *J. Immunol.* 152:4095 (1994), CD59s from human, rat, sheep and pig have some cross-species activity.

CD59 has 24–30% similarity to a family of murine proteins called Ly-6, the similarity being strongest in the amino- and carboxy-terminal regions. The ten cysteines of mature CD59 and Ly-6 are readily aligned. Preferred mutations of CD59 are those which do not disturb these conserved cysteines, are directed to positions at which the creates variation is seen within the Ly-6 family, and which introduce residues found in the corresponding positions of one or members of the Ly-6 family. Reference to the sequences of other homologous proteins, such as the human urokinase plasminogen activator receptor, may also be advantageous.

B. PRODUCTION OF YACS CONTAINING A PLURALITY OF COMPLEMENT INHIBITORS

In one of the preferred processes of the present invention, a Yeast Artificial Chromosome (or YAC) is prepared which contains a plurality of complement inhibiting proteins in a single locus, as described in detail herein.

Production of Multi-gene YACs

Large DNA fragments, like those described for the P1 genomic CD46, CD55, and CD59 genes, frequently give rise to high levels of gene expression with the appropriate tissue specificity. In some applications, such as xenotransplantation, it may be important to utilize multiple transgenes. With large DNA fragments it may be difficult however to use a simple co-injection strategy for the production of transgenic animals with more than one gene. Unlike smaller DNA fragments (>50 kb) that co-integrate at high frequency into a single site in the genome of the transgenic embryo, co-injection of larger genomic genes frequently results in multiple independent integration sites and an increased frequency of gene rearrangements.

Transgenic animals produced through this process contain multiple transgene integration sites. On breeding, these transgenic animals independently segregate the transgenes to their offspring so that most offspring inherit only a fraction of the total number of co-injected transgenes. Furthermore, each integration site represents a disruption of the normal genomic structure, which increases the likelihood of creating deleterious mutations. Potential mutations are a particular concern in applications such as xenotransplantation where a transgenic organ is expected to survive for an extended period of time in a human recipient.

To circumvent these problems, and to create a framework on which additional genes relevant to xenotransplantation can be added, we have designed protocols to assemble a unique human complement regulatory locus, consisting of three large human genomic DNA fragments that encode for CD46, CD55 and CD59. The initial locus, consisting of genes for CD46, CD55 and CD59 will exceed 200 kb.

Recently it has become evident that large fragments of DNA, up to several hundred kilobases, can be successfully microinjected into fertilized eggs, and that these very large DNA-fragments remain intact and functional at a reasonable frequency. See Schedl et al., *Nuc. Acids Res.* 20:3073–3077 (1992); Gaensler et al., *Proc. Nat. Acad. Sci.* 90:11381–85 (1993); Schedl et al., *Nature* 362:258–261 (1993); and Gnirke et al., *Genomics* 15:659–667 (1993). This suggests then that a series of P1 sized genomic fragments could be combined into a single piece of DNA and then microinjected. This strategy would ensure that the transgene locus, composed of multiple P1 sized DNA fragments, consisted of a defined structure and that all of the P1 genes in the locus integrate into a single genomic site. Because the genes are physically linked, this strategy also insures that each of the multiple genes that make up the transgene locus will be faithfully transmitted as a unit to subsequent generations.

Assembly of a Human CRP Locus

Figure 4:
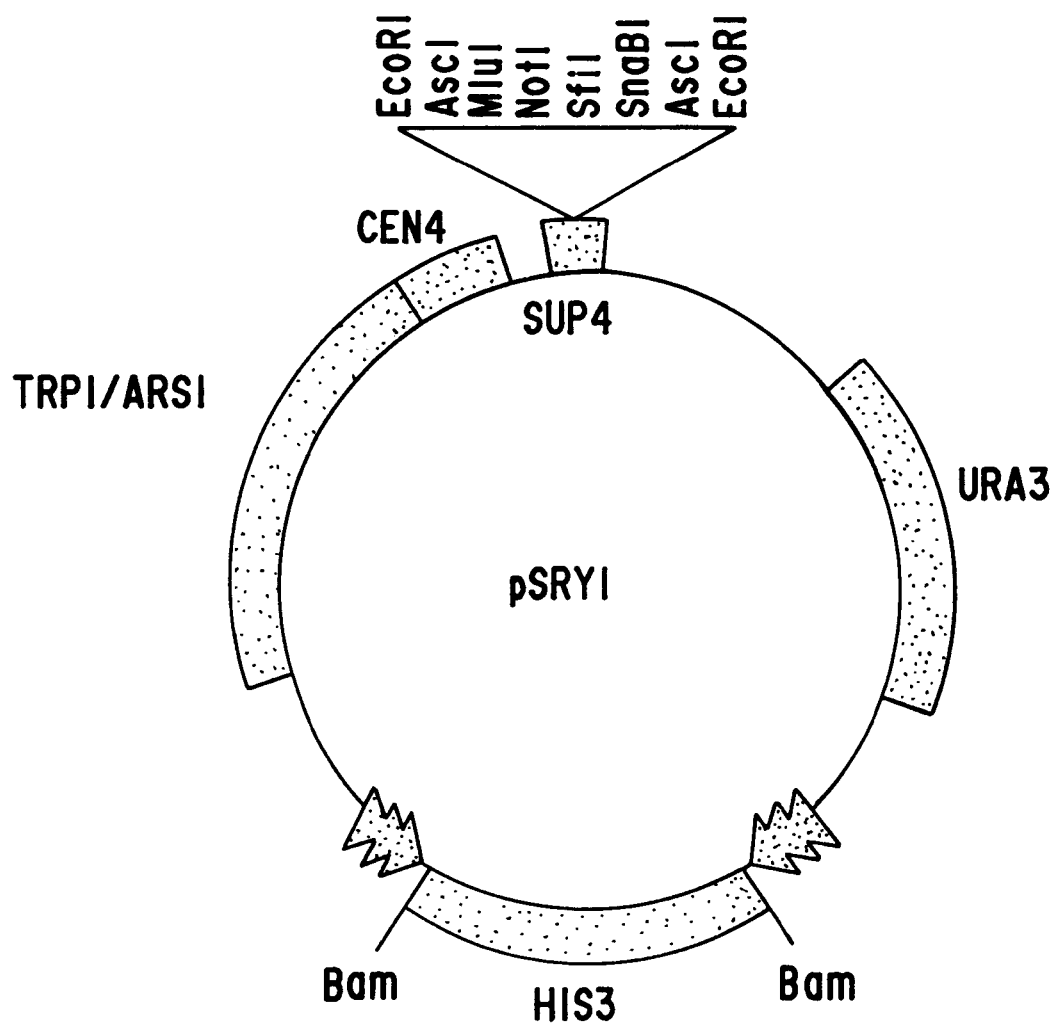
FIG. 4 relates to a New YAC Cloning Vector for the P1 Assembly, and represents the YAC, with all the relevant restriction sites which would be used to create a construct containing MCP, CD59 and DAF (in that order)

Since the P1 cloning system can only package DNA up to 100 Kb, it is necessary to use a yeast (YAC) cloning system (Burke et al., *Science* 236:806–812, 1987) to assemble a locus in excess of this size. Herein, we describe P1 genomic fragments that encode CD59, CD46 and CD55. Together, the three P1 genes sum to 200 Kb of DNA. This size can be easily accommodated by a YAC cloning system. The termini of each P1 genomic fragment is defined by a unique pair of restriction enzyme sites (Table 10). To facilitate assembly of these three genes we have modified the pYAC4 cloning vector to include a multiple cloning site that contains these restriction sites (FIG. 4). The order of the restriction enzyme sites within the multiple cloning site, allows for the sequential assembly of a locus consisting of the three P1 genes. The initial step is to clone the MluI flanked 60 Kb CD46 P1 gene into the Mlu1 site of pSRY-1. This produces a YAC containing the MCP gene. It is preferred that the P1 insert be oriented such that transcription of MCP occurs from the TRP arm side. Similarly, the 70 Kb SfiI CD59 P1 gene is cloned into the SnaB1 site to produce a second YAC containing the CD59 gene. Finally, a Not1 digested MCP-YAC and an SfiI digested CD59-YAC can be linked together with the Not1, SfiI CD55 P1 gene.

Production of YAC-MCP

High molecular weight plasmid DNA consisting of the P1 MCP clone is isolated by alkaline lysis and subsequently purified on a Qiagen-500 column (Chatsworth, Calif.). The DNA is digested to completion with the restriction enzyme Mlu1, extracted with phenol/chloroform (Riley et al., in *Techniques for the Analysis of Complex Genomes*, pages 59–79, 1992) and spot dialyzed against TE (10 mM Tris (pH 7.5), 1 mM EDTA). The plasmid pSRY-1 was digested with Mlu1 and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al., *Analytical Biochem.* 163:391–397 (1987). Transformants were initially selected on ura– plates, then on ura–, trp– plates. Genomic DNA plugs were subsequently made from the urea+, trp+ colonies and analyzed for the presence of a MCP containing YAC by PFGE and Southern blot hybridization. The integrity of the MCP DNA at the cloning site and orientation of the insert can be further determined using plasmid rescue.

Production of YAC-CD59

Because a SfiI restriction site contains 5 random bases the SfiI digest that defines the CD59 P1 gene produces an incompatible 3 base pair overhang that can not be directly cloned into the SfiI site of the SRY-I plasmid. For this reason we describe two methods for cloning the CD59 P1 gene into the pSRY-1 YAC. The first method is simply to clone the 70 Kb CD59 insert as a blunt ligation into the SnaB1 site of pSRY-1. High molecular weight plasmid DNA consisting of the P1 CD59 clone is isolated by alkaline lysis and subsequently purified on a Qiagen-500 column (Chatsworth, Calif.). The DNA is digested to completion with the restriction enzyme end, filled with T4 DNA polymerase, extracted with phenol/chloroform (Riley et al, 1992, see above) and spot dialyzed against TE (10 mM Tris (pH 7 5), 1 mM EDTA). The plasmid pSRY-1 was digested with SnaB1 and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al., (1987, see above). Transformants were initially selected on ura– plates, then on ura–, trp– plates. Genomic DNA plugs were subsequently made from the urea+, trp+ colonies and analyzed for the presence of a MCP containing YAC by PFGE and Southern blot hybridization. The integrity of the CD59 DNA at the cloning site and orientation of the insert can be further determined using plasmid rescue. This approach has proven to be difficult in this instance since it requires a blunt ligation. Additionally, the particular clone grows poorly making it difficult to isolate sufficient quantities of the CD59 P1 insert. Because of these problems we have developed the alternative strategy outlined below.

Production of YAC-DAF

High molecular weight plasmid DNA consisting of the P1 DAF clone is isolated by alkaline lysis and subsequently purified on a Qiagen-500 column (Chatsworth, Calif.). The DNA is digested to completion with the restriction enzyme Not1 and SfiI, extracted with phenol/chloroform (Riley et al, 1992, cited above) and spot dialyzed against TE (10 mM Tris (pH 7.5), 1 mM EDTA). The plasmid pSRY-1 was digested with Not1, SfiI and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al. (1987, above). Transformants were initially selected on ura– plates, then on ura–, trp– plates. Genomic DNA plugs were subsequently made from the urea+, trp+ colonies and analyzed for the presence of a DAF containing YAC by PFGE and Southern blot hybridization. The integrity of the DAF DNA at the cloning site and orientation of the insert can be further determined using plasmid rescue.

Assembly of the Three Gene Locus

To assemble the three gene locus the YAC-MCP chromosome is gel purified from yeast cells using PFGE, and the isolated band is digested with Not1. Similarly the YAC-CD59 chromosome is gel purified from yeast using PFGE, and the isolated band is digested with SfiI. These digested chromosome fragments are then ligated to equimolar amounts of the gel purified 70 kd Not1, SfiI DAF P1 insert and transformed into AB1380 spheroplasts. Transformants are initially selected on ura– plates, then on ura– and trp– plates. Genomic DNA plugs are subsequently made from the ura+, trp+ colonies and analyzed by PFGE and Southern blot hybridization for the presence of a 200 kd YAC containing all three genes.

Alternative Cloning Scheme

The formation of the CD59-YAC has been particularly difficult. This step involves a blunt ligation which is a far less efficient process. In addition the particular CD59 P1 clone grows poorly making it difficult to purify a sufficient quantity of CD59 insert for the blunt ligation. Due to these problems we have also used an alternative method of producing a CD59-containing YACs, such as those disclosed in Ketner et al., 1994, Proc. Nat. Acad. Sci. 91:6186–90. This approach relies on the high frequency of homologous recombination that occurs in yeast. In short, yeast spheroplasts are transfected with three pieces of DNA: the entire CD59 insert, a YAC-Trp arm containing a portion of the extreme 5' region of the CD59 insert and an YAC-Ura arm containing a portion of the extreme 3' region of the CD59 insert. The CD59-YAC results from two homologous recombination events, one between the 5' CD59 sequences in the Trp-YAC arm and the homologous 5' region of the CD59 P1 gene and a second event between the 3' CD59 sequences in the Ura-YAC arm and the homologous 3' region of the CD59 P1 gene (FIG. 5). To use this approach we have isolated the 5' and 3' terminal portions of the CD59 P1 insert by plasmid rescue and partially sequenced these subclones. From this analysis a series of oligonucleotide primers for PCR were produced (Table 12). Primer pairs CH-1 and CH-2 contain a Not 1, SfiI (CH-1) and BamHI restriction sites and amplify a 1.4 kb fragment from the 5' terminus of the CD59 P1 gene. This fragment is cloned into PSRY-I as a Not1, BamHI fragment. The resulting plasmid contains the 6 kb Trp-CEN-ARS YAC arm along with the 1.4 kb 5' CD59 insert. For the 3' end of the CD59 P1 insert, a 1.2 kb PCR product with SnaB1 and HincII was amplified using primers ED-1 and ED-2. This PCR product was blunt cut into the SnaB1 site of SRY-1. The orientation of the 1.2 kb 3' fragment was confirmed by sequencing the junctions of the insert. To assemble the final CD59 YAC, three pieces of DNA were transfected into AB 1380. The CD59 P1 DNA, linearized with Not1, was cotransfected with equimolar quantities of BamHI digested 5' CD59-Trp-YAC arms and SnaB1, BamHI digested 3' CD59-Ura-YAC arms. Transformants were initially selected on ura– plates, then on ura–, trp– plates. Genomic DNA plugs were subsequently made from the ura+, trp+ colonies and analyzed for the presence of a CD59 containing YAC by PFGE and Southern blot hybridization. The integrity and orientation of the CD59 DNA within the YAC can be further determined using Southern blot analysis, plasmid rescue or PCR amplification across the 5' and 3' junction domains. Transformants with the correct structure were isolated at high frequency (Table 11).

Assembly by Homologous Recombination

Figure 5A:
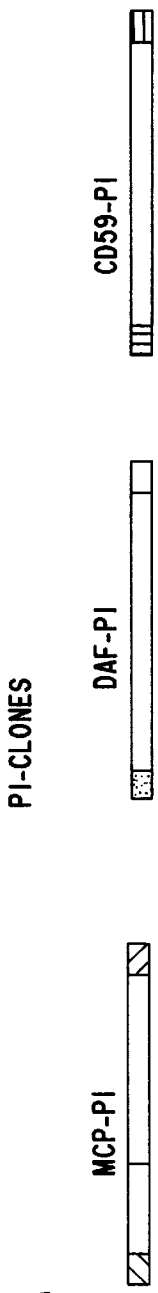
FIG. 5 A–C relates to P1-Clones, and is a diagram of the alternative strategy which is used to incorporate all three complement regulatory proteins into one YAC. Using this strategy the triple gene clone is sequentially assembled using homologous recombination and auxotrophic markers to select the appropriate recombinant (see Example V for more details)

The use of homologous recombination to subclone the P1 genes into YAC vectors is a general approach that can be used to produce MCP and DAF containing YACs, and to facilitate the sequential assembly of a triple gene YAC containing all three complement regulatory genes, or any other additional genes. FIG. 5 outlines how the triple gene YAC can be sequentially assembled. For this approach the extreme 5' and 3' fragments of the P1 genomic CRP genes must be isolated (FIG. 5A), such as by plasmid rescue, subcloning, PCR amplification or any number of standard techniques. To facilitate homologous recombination in yeast these fragments should be unique sequences, devoid of repetitive elements, and approximately 500–2000 base pairs in length. The characteristics of the terminal fragments of CD59, MCP and DAF are presented in Table 13. The sequential assembly of a three gene YAC also requires the use of three selectable auxotrophic yeast marker genes. For our purposes we have used the auxotrophic markers Ura3, Trp1 and Lys2, but other combinations of markers are possible depending on the genotype of the yeast strain being used. The Ura3 and Trp1 markers arms were derived from pSRY1. The Lys2 marker is a 4.5 kb Hind3 subclone of pDP6 (Fleig et al., Gene 46:237–245, 1986) which we added to the 700 bp Hind3, BamHI telomere seed sequences of pSRY-1 to produce a functional Lys2-YAC arm.

Figure 5B:
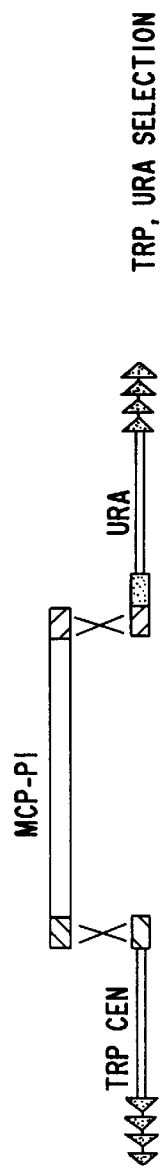

The sequential assembly of a YAC chromosome that contains all three human complement regulatory genomic genes begins with the addition of the 5' terminal fragment from the MCP gene, to the CD59-YAC described above. To make this addition the 3' terminal fragment of CD59 and the 5' terminal fragment of MCP are attached to each other and inserted into a Lys2 YAC arm. In this 3' CD59-5'MCP-Lys2 YAC arm the 3' CD59 sequences serve to target the site of homologous recombination so that when this DNA is transfected into the CD59-YAC containing yeast strain a homologous recombination event between the 3' CD59 sequences effectively deletes the Ura3 marker and replaces it with the Lys2-YAC arm (FIG. 5B). Transformants are initially selected for a functional Lys2 gene using lys– media. Clones are then placed under triple selection using lys–, trp– media which contains 5-fluoroorotic acid (FOA). This media simultaneously selects for the presence of functional Trp1 and Lys3 genes and the addition of FOA selects against a functional Ura3 marker. Yeast clones are further characterized by PFGE and differential Southern blot hybridization analysis using probes to Trp1, Lys2, CD59 and 5' MCP. Although only a few clones were analyzed, transformants with the correct structure and genetic behavior were isolated at high frequency (Table 11).

Figure 5C:
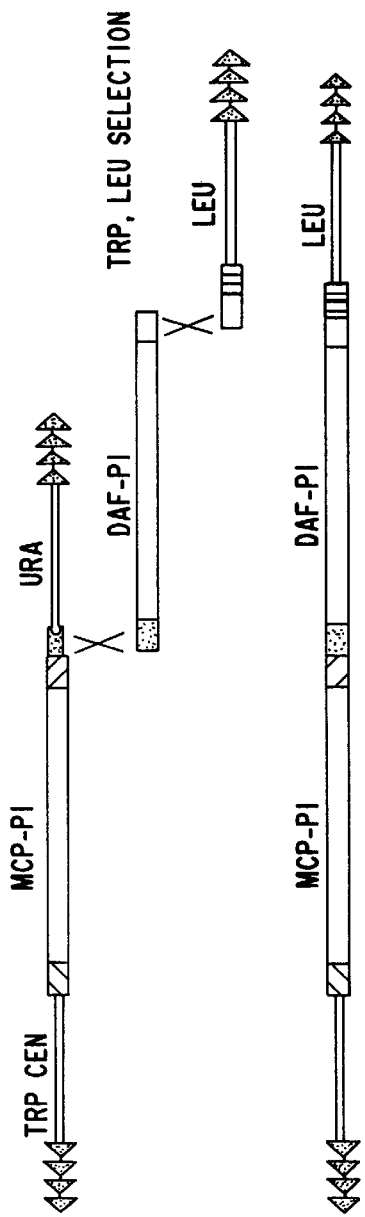

To add the rest of the MCP genomic DNA to the new CD59-5' MCP-Lys2-YAC the 1.3 kb Nco1, Mlul3' terminus of the MCP gene was blunt ligated to a Ura3-YAC arm. This construct was linearized by restriction digest, and cotransfected with Mlul1 digested MCP-P1 DNA into the CD59-5' MCP-Lys2-YAC containing yeast strain (FIG. 5C). Transformants are initially selected for a functional Ura3 gene using ura– media. Clones are then placed under triple selection using ura–, trp– media which also contains α-Aminoadipate (α-Ap). This media simultaneously selects for the presence of functional Trp1 and Ura3 genes and the addition of α-Ap selects against a functional Lys2 marker. Homologous recombination events within the 5' and 3' MCP sequences yield a new chromosome that contains both the CD59 and MCP complement regulatory genes flanked by Trp1 and Ura3 auxotrophic markers. Yeast clones are further characterized by PFGE and differential Southern blot hybridization analysis using probes to Trp1, Ura3, CD59 and MCP. Transformants with the correct structure were isolated at high frequency (Table 11).

The addition of the third gene, DAF, is accomplished in an analogous manner (FIG. 5D). The 1.3 kb 3' portion of the MCP genomic gene was added as an EcoR1 fragment to the plasmid that contained the 2.2 kb 5' portion of the genomic DAF gene. These two gene fragments were then added to the Lys2-YAC arm and transfected into the CD59-MCP-YAC double gene YAC. Through lys– selection and subsequent lys–, trp–, FOA triple selection we derived the CD59-MCP-5' DAF-Lys-YAC clone. The remainder of the DAF genomic gene was integrated to produce the triple gene YAC by cotransfecting the 70 Kb Not1-Sfil DAF genomic DNA with a 0.8 kb 3' DAF fragment attached to a Ura3 YAC arm. After the appropriate selection steps, yeast clones were analyzed by PFGE and differential Southern blot hybridization.

This three gene locus can be used to produce transgenic pigs expressing high levels of all three human complement regulatory genes. This new locus is advantageous over individually injected P1 genes, since all three genes are now physically linked prior to injection, and therefore are expected to integrate as a single locus. Moreover, since this unique locus is propagated as a YAC, the homologous recombination techniques described above can be used to make further additions to the locus. For example genes that reduce or mask the elaboration of the gal epitope, including but not limited to α(1,2)FT, α(2,6)ST, or β(1,3)NAGT can be added, resulting in a locus that could both reduce the level of the major xenogeneic antigen, and control human complement activation. Further additions to the locus could be made, as the development of porcine xenogeneic organ donors progresses. For example, additional human genes that affect vascular rejection (e.g., thrombomodulin, protein C, factor H, tissue factor, urokinase plasminogen activator, ectoATPase, inhibitor of NFkb) or human genes that may affect cellular rejection (e.g., IL-4, IL-10, TGF-β, agents that block co-stimulatory molecules CD28 and CD40, soluble receptors to block cytokine actions such as soluble IL-2 or IFNg receptors) or genes that might be used to destroy porcine antigen presenting cells (such as a CD2 or CD45 regulated gene encoding Herpes simplex thymidine kinase) could also be added to this locus using the methods described above. All of these genes need not be large genomic DNAs, but could be well characterized minigene or any other genetic constructs.

Generation of Transgenic Animals

YAC constructs are prepared for microinjection using well known methods. The yeast chromosomes including the YAC construct are separated using pulse field gel electrophoresis(PFGE), which is designed to resolve very large DNA molecules. To isolate a 160 kb YAC a 1% SeaPlaque GTG low melt agarose (FMC Corp.) pulse field gel, run at 14° C., 6 volts/cm$^2$ for 20 hours with a 120° switch angle and 2–10 second switch times is used. The isolated YAC chromosome is cut from the gel and the agarose gel slice is equilibrated in injection buffer (10 mM Tris(pH 7.5), 0.1 mM EDTA, 100 mM NaCl, 30 μM spermine and 70 μM spermidine). The agarose gel slice is melted at 65° C. and digested with gelase (Epicenter Technology) at 37° C. for 3 hours. The digested agarose is then transferred, using a wide bore pipette tip to a Micron 10 concentrator (Amicon), where the DNA is concentrated by repeatedly centrifuging at 5,000 g for 15 minutes, until the entire content of the original gel slice is reduced to a 20–50 μl volume. The integrity of the YAC DNA can be checked on pulse field gel prior to microinjection.

Microinjection of the DNA construct is then performed as previously described in this application. Analysis of the transgenic animals and their offspring are conducted according to methods previously described in this application.

C. PRODUCTION OF TRANSGENIC ANIMALS UTILIZING P1 CLONES

In another preferred process in accordance with the present invention, transgenic animals can be produced through the construction and transfection of bacteriophage P1 clones, as described in detail below.

In general, oligonucleotide pairs (Table 7), designed from previously published sequence data and corresponding to the 5' and 3' regions of CD59 and CD46 can be used to screen, by polymerase chain reaction, a human genomic library constructed in the bacteriophage P1 (Genome Systems. St. Louis, Mo.). Using both sets of primers, clones can be identified. High molecular weight plasmid DNA can be isolated from the NS3529 strain of *Escherichia coli* by alkaline lysis and subsequently purified on a Qiagen-500 column (Chatsworth, Calif.). Inserts are mapped by restriction enzyme digestion, pulsed-field gel electrophoresis (PFGE) and Southern blot analysis. Candidate fragments for microinjection are chosen based upon the amount of 5' and 3' flanking region existing in each clone.

To prepare fragments for microinjection, the clones were restricted with SfiI or MluI and the digestion mixture was size fractionated by PFGE. After being visualized by ethidium bromide staining, the fragments containing the clones were excised from the gel, purified, concentrated and analyzed for integrity.

Production of Transgenic Mice

Upon purification, the fragments obtained as above can be individually microinjected into fertilized murine oocytes. Founder animals (C57BL/6×SJL $F_2$) are identified by Southern blot analysis and lines were established by backcrossing. Animals possessing two transgenes can be generated by crossing offspring (e.g., CD59 and CD46 $F_1$ animals). In actual examples, from 27 potential founders, 5 (19%) were positive for CD59. MCP genomic clones (both the 60 kb and the 80 kb) produced 13 transgenic founders each, representing a transgenic rate of 29% and 15%, respectively. The 90 kb construct for DAF produced 6 positive transgenic from 19 $G_0$ mice. A 70 kb DAF construct produced 3 out of 18 transgenic founders (17%). Gene transmission to $G_1$ generation was 50% (2/4), 83% (10/12) and 69% (9/13) for CD59, 60 kb MCP and 80 kb MCP fragments, respectively (Table 8). Five out of 6 DAF founder also transmitted the gene to $G_1$ progeny. These data indicate that transgenic mice can be successfully made by microinjecting large genomic fragments and that these genes can be transmitted to subsequent generations.

Expression Analysis in Transgenic Mice

Heterozygote G1 animals were analyzed for expression by Northern analysis, immunochemistry and FACS analysis.

FACS Analysis and Quantitation

Protein expression on the surface of murine peripheral blood cells (erythrocytes and leukocytes) was assessed by indirect immunofluorescence. Cell surface expression was measured by flow cytometry using standard techniques.

Northern Analysis

Total cellular RNA was isolated from tissues, blood, or both and Northern blotting was performed. All probes were fragments radiolabeled with [-$^{32}$P] deoxy-CTP by random priming. Human total RNA samples served as positive controls and were purchased from Clontech (Palo Alto, Calif.).

Immunohistology Analysis

Tissues for immunofluorescence studies were embedded in O.C.T. (Lab Tak, Elkhart, Ind.), snap frozen in isopentane and stored at −80° C. until processing. Frozen tissue samples were prepared in a cryostat (Leica, Heidelberg, Germany). Sections were air dried, fixed with acetone and washed with phosphate buffered saline (PBS). Each section was incubated with monoclonal antibodies (mAbs) and the mAbs were detected with a double fluorochrome layer consisting of FITC-conjugated affinity isolated F(ab)'$_2$ secondary and tertiary antibodies. Tissue sections were washed with PBS after incubations and mounted with a p-phenylenediamine and glycerol solution. Background immunofluorescence was evaluated by preparing sections as previously described and omitting the primary antibody. The rat mAb, YTH 53.1, and the mouse mAb, MCA 695, (Serotec, Washington, D.C.) were used to detect CD59 and CD46, respectively. Additionally, a rhodamine conjugated antibody, provided by A. F. Michaels (University of Minnesota) was utilized to illustrate basement structures. Tissues were examined using a Leitz DMRB epifluoresence microscope (Wetzlar, Germany) and photographed (40×).

Five transgenic lines were identified that express CD59 mRNA as well as protein. A range of mRNA levels in hepatic, cardiac and renal tissue was observed in lines possessing the 70 kb genomic fragment that were basically similar to that seen in humans (detailed in Examples I and II). Transgenic mice expressed CD59 on the surface of endothelial cells in liver, heart and kidney as assessed by immunocytochemistry, and on RBCs as assessed by FACS analysis. These results demonstrate that by utilizing a large genomic CD59 clone tissue specific expression can be achieved.

Eight independent transgenic lines carrying the 60 kb MCP genomic fragment were positive for RNA and protein transgene expression. RNA expression was highest in the kidney and slightly lower in heart and liver. In three transgenic lines RNA levels were comparable to endogenous levels found in the respective human tissues. Protein was expressed on endothelial cells of the liver, heart, and kidney, with the highest expression seen in the liver. Additionally, FACS analysis demonstrated the presence of MCP on the surface of white blood cells. In contrast to CD59 and DAF, MCP protein expression in human circulating blood cells is absent on RBCs. The MCP transgene behaved similarly in that mouse RBCs were negative for human MCP expression. A similar scenario was observed for the 80 kb MCP genomic fragment in which the five lines analyzed were positive for human MCP RNA and protein expression. The tissue distribution for the two constructs was similar. These results imply that by utilizing these particular MCP genomic clones cell type and tissue specific expression can be achieved at levels comparable to those detected endogenously in humans (see Table 9 for details of protein expression on various tissues from two of the transgenic mouse lines).

Functional Analysis

Function of the transgenic human CD59 protein was assessed by measuring protection afforded to blood cells from complement mediated lysis upon exposure to human serum.

Transgenic Mice Possessing Multiple Human Complement Regulatory Genomic Clones

Transgenic mice were generated which possess multiple human complement regulatory genomic clones. This was achieved by cross breeding individual lines expressing different complement regulatory proteins as well as by coinjection of the following clones: a) 70 Kb CD59+60 Kb MCP, b) 70 Kb CD59+90 Kb DAF, c) 60 Kb MCP+90 Kb DAF, and d) 70 Kb CD59+60 Kb MCP+90 Kb DAF (triple injection). Analysis of animals from double and triple injections of P1 clones indicates that co-integration of P1 genes did not occur. Mice carrying both CD59 and MCP P1 genes were obtained by crossbreeding two separate P1 lines. Analysis of these mice is underway to address the additive or synergistic effect of expression of two complement regulatory proteins in a transgenic animal. Such transgenic mice will be useful in determining which sizes of the nucleic acid fragments coding for the complement inhibitors will be most useful in ultimate DNA constructs coding for a locus of genes, such as the YAC constructs discussed above.

Production of Transgenic Pig Lines Containing the P1 Clones

The transgenic pig lines were developed in much the same way as the transgenic mouse lines. Double and triple microinjections of CD59, DAF and MCP were performed. Seven hundred and ninety (790) potential founder pigs were born from March 1994 to March 1995. Of pigs positive for a single transgene, 9 were positive for MCP; 2 were positive for CD59; and 7 were positive for DAF. Three pigs were positive for CD59 and DAF, one pig was positive for MCP and CD59, and one pig was positive for MCP and DAF. A subset of founder pigs were analyzed utilizing blood samples, muscle biopsies or both.

Using the most sensitive method of detection of mRNA (i.e., RT-PCR) 3/3 MCP positive pigs analyzed were positive for MCP mRNA, 1/1 CD59 positive pig analyzed was positive for CD59 mRNA, and 5/5 DAF positive pigs analyzed were positive for DAF mRNA. Northern analysis (a less sensitive method of detection) of blood from the animals did not detect the respective messages. The MCP+

CD59 positive animal had MCP and CD59 messages detectable by RT-PCR, and only the message detectable by Northern analysis. Two CD59+DAF positive animals had both messages at levels detectable by RT-PCR with one animal having DAF mRNA and CD59 mRNA also detectable by Northern analysis. The third CD59+DAF animal had undetectable message by both methods. The MCP+DAF founder pig had MCP mRNA detectable by RT-PCR only.

The data obtained as set forth above needs to be qualified by the observation that founder animals are frequently mosaic. While often undetectable in a founder animal, RNA specific to the transgene is frequently detectable upon transmission of the transgene to offspring. It has been our experience with the P1 transgenic mice that this is particularly true of blood samples. Collection of blood for analysis represents the least invasive procedure available for potentially valuable founder animals and therefore this is the method of analysis currently in use. In addition to the pigs listed above, 31 more pigs have been born and are awaiting testing.

C. EXPRESSION OF NUCLEIC ACID CODING FOR AN ENZYME CAPABLE OF MASKING OR REDUCING THE LEVEL OF THE GAL EPITOPE

In another preferred aspect of the invention, nucleic acid coding for an enzyme capable of masking or reducing the level of the antigenic gal epitope, including but not limited to glycosyltransferases such as $\alpha(1,2)$fucosyltransferase ("$\alpha$(1,2)FT"), $\alpha(2,6)$sialyltransferase ("$\alpha(2,6)$ST"), or $\beta(1,3)$N-acetylglucosaminyltransferase ("$\beta(1,3)$NAGT"), is preferably incorporated into the transgenic animals of the invention so that at least one of these enzymes will be produced along with at least one complement inhibitor in the organs, tissues, cells and non-viable components of the transgenic animals and will thus be useful in making those animals further suitable for xenotransplantation. In one of the preferred embodiments, cDNA coding for an enzyme such as $\alpha(1,2)$FT, $\alpha(2,6)$ST or $\beta(1,3)$NAGT is prepared in the form of an expression vector and used in the preparation of transgenic animals of the invention which expresses one or more of these enzymes so as to be suitable for use in xenotransplantation with reduced or eliminated antibody-mediated hyperacute rejection. In the particularly preferred embodiment of the invention, the nucleic acid coding for the enzyme capable of masking or reducing the level of the gal epitope will be directly incorporated into the nucleic acid constructs prepared above in order to express complement inhibiting proteins, as will be discussed further below, or, alternatively, other modes may be employed to obtain transgenic animals that express both an enzyme capable of reducing the level of the gal epitope and a complement inhibiting protein.

In one of the preferred modes of the present invention, expression vectors are prepared which contain nucleic acid coding for one or more enzymes for reducing or masking the gal epitope, such as $\alpha(1,2)$FT, $\alpha(2,6)$ST or $\beta(1,3)$NAGT, and which can be utilized in preparing the transgenic animals or xenogeneic organs, tissues, cells and non-viable components in accordance with the invention. Preferably, a nucleic acid construct employing the human form of the desired enzymes is prepared using a suitable expression vector, such as a plasmid, and this vector will ultimately be used to prepare transgenic animals, such as by injection of the vector into pronuclei of oocytes from pigs or mice which will eventually express the desired enzyme, or to prepare transfected xenogeneic organs, tissues, cells or non-viable components in accordance with the invention. Although many suitable ways of cloning the desired nucleic acid into an expression vector are well known to those skilled in the art which would be useful in the present invention, in the preferred process, human $\alpha(1,2)$FT, $\alpha(2,6)$ST or $\beta(1,3)$NAGT cDNA is cloned by RT-PCR techniques using total RNA from an appropriate cell line, such as the A431 cell line as disclosed in Larsen et al., *P.N.A.S.* 87:6674–6678 (1990).

In the preferred construct, the human $\alpha(1,2)$FT, $\alpha(2,6)$ST or $\beta(1,3)$NAGT cDNA is cloned via RT-PCR techniques using total RNA from a suitable cell line such as A431. In the cloned cDNA, a sense primer is prepared which preferably has the sequence TTTGGATCC-TCGGCCATGTGGCTCCGGAGCCATCG (SEQ ID NO:1) flanked by the ATG initiation codon and included a BamHI site. The antisense primer is preferably prepared having the sequence AAAGTCGAC-TCAAGGCTTAGCCAATC (SEQ ID NO:2), which flanks the TGA stop codon and includes a Sal I site. This 1.1 kb cDNA was cloned into plasmid pRex 10 (pRex 10/FT) to express $\alpha(1,2)$FT in transfected tissue culture cells.

For expression in transgenic animals in accordance with the present invention, it is preferred that a suitable promoter, such as a chicken $\beta$-actin promoter or an H2k$^b$ promoter, be included in the expression vectors that will include the cDNA coding for the appropriate enzyme. Enhancers may also be added to the DNA construct. In the particularly preferred process, cDNA from enzymes such as $\alpha(1,2)$FT, $\alpha(2,6)$ST or $\beta(1,3)$NAGT is ultimately injected into and expressed by transgenic animals is cloned into vectors containing either a 500 bp chicken $\beta$-actin promoter (#876) (SEQ ID NO:3) or a 4.3 kb H2k$^b$ promoter (#881) (SEQ ID NO:4). In addition, the splice and polyadenylation sequences can be provided to the vector in a 900 bp HindIII/KpnI fragment of human a globin gene containing sequences downstream from the second exon.

In addition, for experimentation regarding expression of the $\alpha(1,3)$GT gene as will be detailed below, porcine constructs containing $\alpha(1,3)$GT cDNA were obtained by RT-PCR using total RNA from porcine aortic endothelial cells and a First strand cDNA synthesis kit.

In one of the preferred modes of the present invention, transgenic animals expressing DNA coding for one or more glycosyltransferases such as $\alpha(1,2)$FT, $\alpha(2,6)$ST and $\beta(1,3)$NAGT are prepared which will have masked or reduced levels of the Gal$\alpha(1,3)$Gal epitope and which can reduce or eliminate antibody-mediated rejection when tissues or organs from said transgenic animals are transplanted into human patients. Preferably, a cDNA construct such as prepared above is used in the preparation of the desired transgenic animal in any of a variety of suitable methods presently known to those of ordinary skill in the art. In the particularly preferred process of the present invention, the transgenic animals are obtained by injecting DNA coding for the desired gal epitope-reducing enzyme into a pronuclei of fertilized oocytes from the donor animal, as will be described further below. After the injection step, the fertilized eggs are then transplanted into pseudo pregnant females where they are carried to term. Following the birth of the animals from the pregnant females, conventional screening tests can be conducted in order to determine which of the offspring contain the gene coding for the desired enzyme, such as $\alpha(1,2)$FT, $\alpha(2,6)$ST or $\beta(1,3)$NAGT. In the preferred process, cells are obtained from the offspring animals and analyzed using PCR techniques to identify which animals contain the introduced gene, and these tests can be confirmed by other suitable methods, such as Southern DNA analysis.

In the method of the present invention, any xenogeneic animal that normally expresses the Galα(1,3)Gal epitope may be utilized to prepare the transgenic animals or xenogeneic cells of the invention. Particularly suitable for use in the invention are pigs which, when manipulated to express the desired gal epitope-reducing enzymes in accordance with the present invention, can be used to prepare organs and tissues which can be transplanted into human patients without generating an antibody-mediated reaction. In addition, transgenic mice, such as the C57BL/6 mouse, have been prepared in accordance with the present invention, and as set forth below contain organs, tissues, cells and non-viable components that express the α(1,2)FT gene and achieve a concomitant masking or reduction in the level of the gal epitope recognized by human xenoreactive antibodies.

It is also contemplated that other animals useful in the present invention to produce tissues or organs for use in xenotransplantation or further research in this field will include those animals from standard commercial sources such as laboratory rats or other suitable animals. In addition, other domesticated animals including cows, sheep and goats that can be genetically engineered using techniques known to those skilled in the art may also be useful in the present invention.

Transfected xenogeneic organs, tissues, cells and non-viable components produced in accordance with the present invention can also be useful in further experimentation regarding xenotrans-plantation in addition to their use in transplantation with reduced or eliminated antibody-mediated rejection such as hyperacute rejection. In these methods, it is contemplated that the transgenic animals produced in accordance with the present invention will be used to create a surface mask or envelope of acceptable xenogeneic cells or tissues which can be placed directly onto, or made to completely surround, natural or artificial donor tissue or organs which possess epitopes recognized by xenoreactive antibodies and which would otherwise be rejected in the human patient. In this manner, the present invention can be useful in that xenogeneic cells prepared in accordance with the invention which express one or more enzymes that can reduce or mask the level of the antigenic gal epitope can be utilized to further increase the supply of potentially useful donor tissue and organs by blocking or reducing the hyperacute response and other antibody-mediated rejection that would normally occur.

As set forth below, it is contemplated that the expression vectors containing nucleic acid coding for an enzyme capable of reducing the level of the gal epitope will be utilized to create transgenic animals that also contain nucleic acid coding for a complement inhibitor, and that expression of both these enzymes and complement inhibitors in the transgenic animal so produced will be extremely suitable for xenotransplantation, and which further reduces the likelihood that the organs, tissues, cells or non-viable components from these transgenic animals will generate a hyperacute rejection when transplanted into human patients.

D. OBTAINING ANIMALS EXPRESSING DNA CODING FOR BOTH AN ENZYME CAPABLE OF REDUCING THE LEVEL OF THE GAL EPITOPE AND A COMPLEMENT INHIBITOR

In the particularly preferred process of the present invention, a method of xenotransplanting tissues or organs into human patients is provided which reduces or eliminates antibody- and complement-mediated rejection, including hyperacute reaction, wherein a transgenic animal is produced that expresses one or more enzymes, such as α(2,6)ST, α(1,2)FT or β(1,3)NAGT, that reduces the level of the gal epitope in its cells along with one or more complement inhibiting proteins, including but not limited to CD59, DAF, MCP and/or other complement inhibitors as set forth above, and the desired tissues or organs from said transgenic animal are transplanted into a human patient with greatly reduced or eliminated antibody- or complement-mediated rejection. In the preferred mode, a nucleic acid construct, such as a YAC, can first be prepared in the manner described above to incorporate at least one complement inhibitor gene, and preferably nucleic acid such as cDNA coding for an enzyme which masks or reduces the level of the gal epitope is added to this YAC at the same locus so that both the enzyme and the complement inhibitor will be expressed at the same time when this construct is transfected into a transgenic animal. Alternatively, separate constructs, such as individual minigenes coding for one or more complement inhibitors and for one or more gal epitope-reducing enzymes, may also be prepared and ultimately used to prepare the transgenic animals of the invention via co-injection, breeding, or other suitable techniques as will be set forth below. Ideally, if separate constructs are employed, a suitable transgenic animal can be obtained by co-injecting a minigene coding for at least one enzyme capable of reducing the level of the gal epitope along with a minigene coding for at least one complement inhibitor.

Successful co-injection of multiple genes into fertilized pig oocytes is dependent upon several variables such as DNA concentration and DNA construct length. Consideration must be given to the length of each construct since a large construct may interfere with successful incorporation of a smaller construct if both are injected together. Manipulations of this kind are well known to those skilled in the art of microinjection. Once the offspring are born, their tissues and/or blood are subjected to both immunohistochemical and functional analyses in order to identify double transgene animals. These founder animals are then bred according to procedures well known in the art to establish a pig line which routinely expresses both transgenes.

In addition, in accordance with the invention, it is possible to produce the ultimate transgenic animals such as pigs (or mice) in accordance with the invention by first producing a generation of transgenic animals which express nucleic acid coding for at least one enzyme which can mask or reduce the level of the gal epitope, including but not limited to α(1,2) FT, α(2,6)ST or β(1,3)NAGT, and at the same time producing a generation of transgenic animals that can express nucleic acid coding for at least one complement inhibitor protein, including but not limited to CD59, MCP, DAF and/or other complement inhibitors. In this mode of the invention, the production of the desired transgenic animals in accordance with the invention can be obtained by the cross-breeding of these two types of transgenic animals as would be accomplished by those well known methods of breeding (e.g., putting males expressing one of the desired genes together with females expressing the other desired gene and letting nature run its course), and in this manner a second generation transgenic animal which contains nucleic acid coding for both the desired enzymes and complement inhibitors can be obtained. In the usual case, tissues and/or blood samples from the resulting second generation offspring can be subject to both immunohistochemical and functional analyses in order to identify those offspring expressing both of the desired genes. Once identified as expressing both characteristics, these transgenic animals can be utilized to establish a line of animals, such as pigs, which routinely express both an enzyme capable of reducing the gal epitope and a complement inhibitor.

In still another embodiment of the present invention, a transgenic animal in accordance with the present invention can be obtained through co-injection of genes or DNA coding for an enzyme reducing the level of the gal epitope and for a complement inhibiting protein. As discussed further below, in this aspect of the method of the invention, transgenic animals are obtained by injecting the desired DNA, which in this case will include DNA coding for an enzyme, such as α(1,2)FT, α(2,6)ST, and/or β(1,3)NAGT, which is capable of reducing the presence of the gal epitope in the endothelial cells of the animal, along with DNA coding for a complement inhibitor, including but not limited to CD59, MCP and/or DAF, into the pronuclei of fertilized oocytes from the donor animal. After the injection step, the fertilized eggs are then transplanted into pseudo pregnant females where they are carried to term. Following the birth of the animals from the pregnant females, conventional screening tests can be conducted in order to determine which of the offspring contain the gene coding for both the desired enzyme and the complement inhibiting protein. In the preferred process, cells are obtained from the offspring animals and analyzed using PCR techniques to identify which animals contain both of the introduced genes, and these tests can be confirmed by other suitable methods, such as Southern DNA analysis.

In the preferred embodiment in accordance of the present invention, any one of the above methods will be used in order to produce transgenic animals coding for at least one complement inhibitor and at least one enzyme capable of reducing or masking the level of thr gal epitope. However, it is generally preferred that expression vectors be constructed which contain nucleic acid coding for more than one complement inhibitor and for more than one enzyme capable of reducing the level of the antigenic gal epitope.

The techniques for obtaining transgenic animals in accordance with the invention will be further described below.

Target Animal

The target animal for the expression of the proteins of interest to the present invention is preferably a vertebrate animal, i.e., a mammal, bird, reptile, fish or amphibian. Among mammals, the preferred target animals for the present invention, the target animal preferably belongs to the order Artidactyla (e.g., cows, pigs, sheep, goats, horses), Rodentia or Lagomorphs (e.g., rabbits, mice, rats), or Carnivora (e.g., cats, dogs). Should other animals be considered for use in the method of the present invention, among birds, the target animals would preferably be of the orders Anseriformes (e.g., ducks, geese, swans) or Galliformes (e.g., quails, grouse, pheasants, turkeys and chickens), and among fish, the target animal would preferably be of the order Clupeiformes (e.g., sardines, shad, anchovies, whitefish, salmon and trout). The preparation of various transgenic vertebrates is discussed in the following articles:

Mammals

Hammer et al., *J. Anim. Sci.*, 63:269–78 (1986); Hammer et al., *Nature*, 315:680–683 (1985); Simons, *Bio/technology*, 6:179–183 (1988); Murray et al., *Reprod. Fertil. Dev.*, 1:147–55 (1989); Rexroad et al., *Molec. Reprod. Dev.*, 1:164–69 (1989); Vize et al., *J. Cell Sci.*, 90:295–300 (1988); Wieghart et al., *J. Reprod. Fertil.* (Suppl. 41) 89–96 (1990); Oren et al., *Proc. Nat. Acad. Sci. USA* 87:5061–65 (1990); Brinster et al., *Proc. Nat. Acad. Sci. USA* 92:4438–42 (1985).

Birds

Salter et al., *Virology*, 157:236–40 (1987); Bosselman et al., *Science*, 243:533–35 (1989); Bosselman et al., *J. Virol.*, 63:2680–89 (1989); Crittenden et al., *Theor. Appl. Genet.*, 77:505–15 (1989).

Amphibians

Rusconi et al., *Proc. Nat. Acad. Sci. USA* 78:5051–55 (1981).

Fish

Zuoyan et al., *Kexve Tongbau*, 31:988–90 (1986); Maclean et al., *Bio/Technology*, 5:257–61 (1987).

In one embodiment, the target animal is a nonhuman mammal, from which organs or tissues are to be transplanted to a human subject. The target animal is transgenic and preferably expresses the proteins and enzymes as set forth above on red blood cells and on endothelial cells located on the intended organ or tissue transplant (collectively, the "target tissue"), which is subsequently transplanted to the subject. As set forth above, in the preferred mode these proteins include at least an enzyme which masks or lowers the level of the gal epitope and a complement regulatory protein.

Raising non-human mammals specifically for use as donors of organ transplants has many advantages provided that the recipient will accept the organ or tissue. First, a carefully raised non-human animal is less likely to be damaged or to carry a pathogenic virus or neoplasm than a human donor. Note that human donors are frequently deceased, with the death resulting from a cause which might make the donated organ less than ideal. Secondly, the size and age may be carefully controlled with xenotransplants compared to the random choice of human organ donors. Thirdly, potential recipients frequently cannot wait for long periods of time until a donated organ becomes available. Organs from non-human mammals are likely to be available in greater quantities, and on a more consistent basis, than cognate human organs. If a graft fails, a backup organ should also be readily available. Finally, organs and recipients are presently matched primarily for MHC compatibility. If rejection is less of a concern, more attention may be given to other considerations, such as size matching.

In accordance with the present invention, a variety of discordant animals may be used as donors for organ and tissue transplantation in humans and other mammals. The choice of animal will depend on the particular organ or tissue desired, the size and sex of the recipient. For human recipients, a pig is generally preferred due to its size, similar physiology, ease of genetic manipulation, reproductive rate and convenience. Other animals, such as sheep, goats, cattle, etc., may also be used. Should the recipient not be human, the choice of animal may vary but by using the same selection criteria, one skilled in the art can choose an appropriate donor animal.

The laboratory mouse has been the most popular host animal for use in the development of transgenic animals, as there are numerous strains available. Mice are, of course, the most widely available laboratory animal, and many strains are available. See *Genetic Variants and Strains of the Laboratory Mouse* (Gustav Fischer Verlag, 1981). However, there are no substantial restrictions on the use of other laboratory or livestock species in such work. Among the higher mammals, pigs are preferred.

Techniques for the production of transgenic animals are well known, and include those techniques described in numerous journal articles, including Gordon et al., *Meth. Enzymol.*, 101:411 (1983); Brinster et al., *Proc. Nat. Acad. Sci. (USA)*, 82: 4438–42 (1985); Palmiter et al., *Ann. Rev. Genet.* 20:465 (1996); Brinster et al., *The Harvey Lectures*, Series 80, 1–38 (1986); Scangos et al., *Adv. Genet.*, 24:285 (1987); Cuthbertson et al., *Lab. Investig.*, 58:484 (1988);

and Camper, *BioTechniques,* 5: 638 (1987). In addition, such techniques are described in Hogan et al., *Manipulating the Mouse Embryo: A Laboratory Manual* (Cold Spring Harbor Lab. 1986); and Levine et al., "Gene Transfer into the Germline," in Kucherpati, ed., *Gene Transfer* (Plenum Press 1986); Palmiter et al., *Cell,* 41:343–45 (1985).

In the processes for preparing transgenic animals in accordance with the invention, procaryotic vector DNA (more particularly any prokaryotic replicon) should be removed before the transgene is introduced into the host cell(s) to be developed into a transgenic animal. For example, the inclusion of large flanking sequences of lambda DNA in early beta-glob#n transgene constructs apparently inhibited expression of the transgene in transgenic mice. See Wagner, et al., in *Molecular and Cellular Aspects of Reproduction,* 319–349 (1996).

Transgenic, Chimeric and Genetically Engineered Animals

In a transgenic animal, the transgene is contained in essentially all of the animal's cells, including germ cells, such that it can be transmitted to the animal's offspring. In a chimeric animal, at least some cells endogenous to the animal bear the transgene, but germ line transmission is not necessarily possible. The transgene may be limited to particular somatic tissues. The term "genetically engineered animals" includes both transgenic and chimeric animals. It is intended to extend, not only to the originally produced animals, but also to those of their offspring which retain and express the transgene.

However, since germ line transmission of transgenes is usually advantageous, production of transgenic animals is usually preferred. The discussion below therefore refers to "transgenic" animals, however, such references apply, *mutatis mutandis,* to chimeric animals.

A number of techniques may be used to introduce the transgene into an animal's genetic material, including, but not limited to, retroviral infection, electroporation, microinjection of the transgene into pronuclei of fertilized eggs, and manipulation of embryonic stem cells such as described in U.S. Pat. No. 4,873,191 by Wagner and Hoppe, incorporated herein by reference. In addition, other suitable techniques including those reported in Palmiter et al., *Ann. Rev. Genet.* 20:465–499 (1986) and French Patent Application 2593827, published Aug. 7, 1987.

The overwhelming majority of transgenic animals (and all transgenic livestock) produced to date have resulted from pronuclear microinjection of DNA. The technique involves the delivery of DNA in solution to one of the pronuclei of a fertilized ova. The pronuclei of the fertilized ova may be observed at 200X under differential interference contrast optics. In the case of ova from pigs, cattle and sheep, the ova should first be centrifuged to sediment cytoplasmic lipids which make visualization of the pronuclei difficult. See Hammer et al., *Nature* 315:680–683 (1985).

Holding and microinjection pipettes utilized in the microinjection process are manufactured from (1 mm O.D., 0.78 mm I.D.) borosilicate glass capillaries. The capillaries are preferably heated in a microforge and pulled to make the microinjection or holding ends. After microinjection, the surviving ova are transferred into a recipient female in the appropriate stage of estrus.

There are alternatives to microinjection, for instance, the infection of pre-implantation embryos (one cell to eight cell) with genetically engineered retroviruses, such as described in Jaenisch, *Proc. Nat. Acad. Sci. (USA)* 73:1260–1264 (1976). In this case, the zona pellucida is removed and the embryos are co-cultured with fibroblasts during the infection process. Infected embryos may then be placed back in a zona pellucida and transferred to an appropriate recipient.

Another approach to producing transgenic animals involves electroporation. In this technique, the one cell ova is placed in a electroporation chamber with a solution of DNA. A pulsating electric field is generated through the chamber to drive the DNA into the ova.

Embryonic stem (ES) cell lines are derived from the cells of the inner cell mass of mammalian (e.g., mouse and hamster) blastocytes. ES cells are maintained in the stem cell state by growth on a feeder layer, e.g., of primary embryonic fibroblasts or of the embryonic fibroblastic cell line STO. The ES cells may be genetically modified by any technique suitable to in vitro mammalian cell culture, and then injected into the blastocyst. They then differentiate and colonize most if not all tissues of the animal, including the germline. See Deutschman, "Gene Targeting in Embryonic Stem Cells", Chap. 4, pp. 89–100, of First and Haseltine, *Transgenic Animals* (Butterworth-Heinemann: 1988).

Although most studies have involved transgenic mice, other species of transgenic animals have also been produced, such as rabbits, sheep and pigs (Hammer et al., 1985, above), chickens (Salter et al., *Virol.* 157:236–240, 1987), rats (Mullins et al., *Nature* 344:541–544, 1990), goats (Denman et al., *Bio/Tech.* 9:839–843 (1991) and cows (Krimpenfort et al. *Bio/Tech.* 9:844–847, 1991).

E. TRANSPLANTATION OF TISSUES AND ORGANS OBTAINED FROM TRANSGENIC ANIMALS PRODUCED IN ACCORDANCE WITH THE INVENTION

As will be readily apparent to one skilled in the art, once the transgenic animals in accordance with the present invention are produced, the organs, tissues, cells and non-viable components of said animals may be transplanted into appropriate human recipients in any of the many ways presently utilized in this field which are well known in the art. The list of organs which may be transplanted is very long and is only limited to the extent that surgical techniques are available to transplant such organs. Certain tissues, cells or parts of organs may also be transplanted. For the purposes of the appended claims, the term "organ" includes whole organs, parts of organs and miscellaneous tissues. Examples include kidney, eye, heart, heart valve, skin, liver, bone marrow, intestine, blood vessels, joints or parts thereof, pancreas or portions containing the islets, lung, bronchi, brain tissue, muscle and any other vascularized tissue. However, the transfusion of blood or blood components thereof is not to be construed as being an organ transplant.

Transplantation may be performed to correct an organ which is improperly functioning as a result of injury, genetic defect, disease, toxic reaction, etc. The recipient may receive the transplanted organ to supplement existing tissue such as using skin tissue for treating burns, pancreatic islets for diabetes or brain tissue for treating Parkinson's disease. Alternatively, the recipient's defective organ may be completely removed and replaced with the xenograft such as in kidney, heart, liver, lung or joint transplants. For some organ transplants, it is possible for either technique to be used such as with diver transplants for treating cirrhosis and hepatitic neoplasms and infections.

The present invention is thus capable of providing suitable donor organs, tissues, cells and non-viable components which express both at least one enzyme, such as $\alpha(2,6)$ST, $\alpha(1,2)$FT or $\beta(1,3)$NAGT, which masks or lowers the level of the antigenic gal epitope in the cells of the transgenic animal, and at least one complement inhibitor protein, such as CD59, MCP, DAF and/or any of the numerous complement inhibiting proteins discussed above, and these tissues, organs and cells can be used in human transplantation with a greatly reduced likelihood of generating an antibody-mediated or complement-mediated immune response. In the preferred mode of the present invention, transgenic animals, such as pigs or mice, are prepared in accordance with the steps as described above, and preferably the desired organs and tissues from the transgenic animals can be isolated, removed and utilized for transplantation into the human patients using conventional transplantation methods currently known. Through the use of organs and tissues expressing the DNA coding for the proteins or enzymes discussed above, the risk of sever antibody-mediated or complement-mediated rejections such as hyperacute rejection will be greatly reduced, and it may be possible to achieve xenotransplantation without the need for extensive or rigorous immunosuppression which normally accompanies such methods. Of course, for each particular situation, it will be determined by the appropriate medical personnel at the time of transplantation and following post-transplant recovery whether immunosuppressive treatment is necessary, but in any event, immune rejection will be greatly lessened by the processes of the present invention as set forth in detail above.

The present invention is thus extremely advantageous in that it provides donor organs, tissues and cells that will be more suitable for use in xenotransplantation than xenogeneic tissues and organs currently available, and the invention will thus greatly assist in reducing the tremendous backlog of donor organs and tissues which severely restricts the scope and effectiveness of transplantation therapy.

The preferred embodiments and other features of the present invention will be set forth in or apparent from the following examples which are designed to be exemplary or illustratory of the present invention and not intended to be limiting thereof. The foregoing description of the specific embodiments reveal the general nature of the invention so that others can, by applying current knowledge, readily modify and/or adapt for various applications such specific embodiments without departing from the generic concept, and, therefore such adaptations and modifications should and are intended to be comprehended within the meaning and range of equivalents of the disclosed embodiments. It is to be understood that the phraseology or terminology employed herein is for the purpose of description and not of limitation.

EXAMPLES

Example I

CD59 Minigene No. 1

1.1 Construction of the CD59 Minigene No. 1

A part of the human CD59 CDNA containing exon 2, exon 3, exon 4 sequences and the 667 bp 3' untranslated (UT) sequence was amplified, utilizing the Polymerase Chain Reaction (PCR) under predetermined conditions, using 5' (5'-ACCGGGAATTC TTCCTTCCAGGTTCTGTGGACAATCACA<u>ATG</u>GG-3') (SEQ ID NO:5) and 3'(5'CACGGGAGCTCGCTATTACACTTTTCCAGTGG-3') (SEQ ID NO:6) primers. The 5' primer was flanked by an EcoRl Site (bold), including 10 bases corresponding to the 3' end of intron 1 (italics), and extending to 2 bases downstream of the initiating methionine (underlined). The 3' primer was flanked by a Sac1 site (bold). The resulting PCR product contained 1072 bp of CD59 cDNA including a splice acceptor site 5' of exon 2 with EcoRl and Sac1 sites introduced at the 5' and 3' ends, respectively.

A 1033 bp sequence of the 3' flanking region of the gene was amplified by PCR with Sac1 and Xho1 sites (bold) introduced at the 5' and 3' ends, respectively using primers (5'-CACGGGAGCTCATACATCAATGGTGTGTTAAAGC-3') (SEQ ID NO:25) and (5'-CACGCTCGAGGCTCCTGGCTTTCTGGAGTTGG-3') (SEQ ID NO:6). These PCR products were joined to give a 2105 bp EcoRl/Xho1 fragment. A 3.0 Kb Sal1/BamHl fragment encompassing the contiguous 3' UT region of CD59 was isolated from a lambda clone and joined to the Xho1 site of the above PCR product. The resulting fragment was introduced downstream of a 10.5 Kb Sal1 fragment which contained the 5' flanking region of the CD59 gene, exon 1 and 4 Kb 3' flanking sequence of exon 1. Sequence analysis indicated that the cDNA encodes a variant protein with a Thr-to-Ala substitution at amino acid 76. The resulting fragment was 15.5 Kb in length (see FIG. 1).

1.2 Production of Transgenic Mice

A 15.5 Kb DNA fragment containing 6.5 Kb of the 5' untranslated portion of the human CD59 gene, exon 1, 4.0 Kb of the 5' end of intron 1, exons 2, 3 and 4 as a cDNA, and 4.7 Kb of the 3' untranslated region containing all 5 characterized olyadenylation signals was constructed. The minigene was excised sing Not I sites in the vector polylinker and microinjected into fertilized mouse eggs to obtain transgenic mice. The founder mice were C57BL/6× SJL $F_2$ crosses. Nineteen out of 63 (30%) of the mice born were transgenic for the CD59 minigene construct. Lines were established from the positive mice by backcrossing with C57BL/6 mice. Five of the 13 (38%) transgenic mouse lines expressed CD59 mRNA in their liver, heart and kidneys. Line 5-2, which expresses the highest levels of CD59 mRNA, was chosen for detailed analysis.

1.3 Expression Analysis in Transgenic Mice 1.3.1 Northern Blot Analysis

RNA from the liver, heart, kidney, lung, brain, muscle, blood and spleen was extracted and analyzed using Northern blot analysis. Two transcripts, 1.9 and 2.1 Kb, were detected in all tissues, with the exception of blood and spleen, at levels which were estimated to be at least 10-fold lower than that observed in human tissues.

1.3.2 Immunohistology Analysis

Analysis of various tissues from line 5-2 by immunohistology using a monoclonal antibody specific for human CD59 was undertaken to determine the tissue and cell type specificity of the human CD59 minigene in transgenic animals. Antibodies specific for CD59, human C5b, human C3d and membrane attack complex were used for immunostaining. Detection of human IgM on tissues was accomplished by using a mu-chain specific FITC-conjugated goat anti-human IgM monoclonal antibody. Frozen sections were cut to a width of 4 $\mu$m and stained with the antibodies using optimized conditions. The results of this analysis showed that protein in the transgenic mice line was expressed on endothelial cells lining the arterioles and capillaries of the heart, which is consistent with the expression of CD59 in humans. Hearts from non-transgenic littermates were negative when stained for human CD59. CD59 was observed at high levels on transgenic mouse placenta, as well as on lung epithelial and endothelial cells, and skin epithelia. Low levels of CD59 protein was detected on endothelial cells lining the portal triad of the transgenic mouse liver, in skeletal muscle and pancreatic endothelia and epithelia. Kidney, spleen and brain tissues of transgenic mice were negative for human CD59 protein expression.

1.3.3 FACS Analysis

In contrast to the high level of expression of CD59 observed on human circulating blood cells, the transgenic mice did not express the protein on erythrocytes nor on leukocytes as analyzed by flow cytometry. This was confirmed by the absence of CD59 protein in transgenic mouse spleen and undetectable levels of CD59 mRNA in transgenic mouse blood and spleen. Thus the minigene was capable of directing expression of human CD59 in a subset of tissues that express CD59 in humans.

1.4 Functional Analysis in Transgenic Mice

To ascertain whether human CD59 expressed in transgenic mice can inhibit formation of the membrane attack complex, heart perfusion experiments were perfused on six mice. Hearts from three transgenic mice and three non-transgenic littermates were perfused ex vivo using human plasma (see Langendorff, *Pflugers Arch.* 61:291–332, 1995). It is known that under certain experimental conditions human IgM binds to mouse endothelial cells and complement is activated in part by the classical pathway as evidenced by codeposition of C4. Immunopathological detection of human IgM on heart biopsies, performed on the six mouse hearts after perfusion, showed a similar distribution and staining intensity on both control and transgenic heart tissues. This suggests that all the hearts were equally well perfused with the human blood and that human IgM antibody recognized and bound mouse endothelial cells.

A comparison of membrane attack complex deposition between mouse hearts expressing human CD59 and negative littermates shows a substantial decrease in MAC deposition on the transgenic hearts. Interestingly, deposition of human C3d and C5b was also substantially diminished after perfusion of transgenic mouse hearts as compared to controls. It is clear that in this model of xenograft rejection, human CD59 expressed in a transgenic mouse heart can inhibit the activation of human complement.

1.5 Production of Transgenic Pigs

The transgenic pig line was developed in much the same was as the transgenic mouse line. The CD59 minigene was microinjected into fertilized porcine ova to obtain the founder pigs. Analysis of the pigs was accomplished using a tail sample from each pig. The tail samples were subjected to Southern blot analysis to identify transgenic animals. Of the 49 piglets that were born, 2 (4%) were identified as transgenic for the human minigene. Both founder animals were bred to generate heterozygous $G_1$ transgenic lines for tissue analysis.

1.6 Expression Analysis in Transgenic Pigs

1.6.1 Northern Blot Analysis

RNA from the liver, heart, kidney, lung, muscle, skin and spleen was extracted and analyzed using Northern blot analysis. Two transcripts of 1.9 and 2.1 Kb were detected in all tissues at levels which are estimated to be at least 10-fold lower than that observed in human tissues.

1.6.2 Immunohistology Analysis

Immunohistology analysis using a monoclonal antibody specific for human CD59 was undertaken to determine the tissue and cell type specificity of the human CD59 minigene in transgenic animals. Frozen sections were cut to a width of 4 μm and stained with the antibody using optimized conditions. The results of this analysis showed that CD59 protein is expressed on endothelial cells lining the large blood vessels of the heart derived from a transgenic pig, but was undetectable on the microvasculature of this organ. This was in contrast to endogenous expression observed in human heart tissue, where the protein was present at high levels and detected uniformly on cells lining all blood vessels. Incubation of transgenic porcine RBCs with a monoclonal antibody specific for human CD59 and analysis by FACS demonstrated the expression of human CD59 on pig erythrocytes, but not to the level expressed in human RBCs. While protein expression levels were lower than endogenous levels in human tissues, the spectrum of tissues positive for transgenic protein expression mirrored that seen in humans. This was not the case with transgenic mice where kidney and blood cells were consistently negative for CD59 transgene expression.

1.7 Functional Analysis in Transgenic Pigs

1.7.1 Analysis Using PAECs

In order to characterize the expressed human CD59 transgenic protein and measure the functional activity, porcine aortic endothelial cells (PAECs) were isolated from both transgenic and nontransgenic pig hearts and analyzed on FACS. The PAECs of the transgenic pig hearts expressed human CD59. A total of 5670 molecules of human CD59/cell were detected on the PAECs from the transgenic pigs compared to 41,515 molecules of CD59/HUVEC cell (human umbilical vein endothelial cells), giving approximately a 5-fold difference in expression.

1.7.2 Analysis of GPI Linkage

In order to determine whether the CD59 minigene protein is appropriately processed with a GPI tail, PAECs and HUVECs were incubated with PIPLC (phosphatidyl inositol phospholipase C); specific cleavage of the GPI-linked tail can be demonstrated using PIPLC. Transgenic PAECs and HUVECs were analyzed by FACS utilizing double staining for Factor VIII (a transmembrane endothelial cell-specific marker) and human CD59 before and after incubation with PIPLC. As expected there was no change in the percentage of positive PAECs or HUVECs for Factor VIII detected before and after treatment with PIPLC. However, direct quantitation showed a substantial reduction (81%) in PAECs expressing CD59 protein after incubation with PIPLC, indicating that the human CD59 transgenic protein is correctly processed for addition of a GPI-linkage. When the HUVECs were treated with PIPLC, 79% of the cells became negative for CD59 protein expression, as determined by FACS analysis. Additionally, non-transgenic PAECs were positive for Factor VIII, negative for human CD59 and showed identical profiles before and after PIPLC treatment.

1.7.3 Analysis of Functional CD59

The function of human CD59 on porcine aortic endothelial cells was measured by testing the sensitivity of PAECs to complement mediated cytotoxicity upon exposure to human serum. PAECs from transgenic and non-transgenic littermates were incubated with increasing dilutions of human serum and cell toxicity was monitored by propidium iodide uptake. PAECs from the transgenic pigs (those expressing human CD59) were protected from complement-mediated cytotoxicity as compared to their non-transgenic littermates. A 4-fold higher concentration of human serum was required to lyse 40% of the transgenic PAECs as compared to the amount necessary to lyse the non-transgenic PAECs. It was demonstrated that the protection conferred to the transgenic PAECs was specific to the human CD59 protein as preincubation of PAECs with a F(ab')$_2$ fragments from a monoclonal antibody specific for human CD59 abolished protection of the transgenic PAECs but had no effect on the non-transgenic PAECs.

To assess the biological function of the human CD59 protein expressed on endothelial cells of a whole organ and to examine the contribution of low levels of the transgenic protein to the endogenous CRPs, heterotropic transplantations of transgenic pig hearts into baboons using one Gl pig from each transgenic line were performed. After reperfusion, the grafted hearts continued beating for 2.25 and 3 hours, respectively, which was slightly longer than for non-transgenic pig hearts (0.5 to 1.5 hours). Although the graft survival was prolonged only slightly, the transgenic xenografts exhibited evidence of resistance to complement-mediated injury. The non-transgenic pig hearts demonstrate clear endothelial cell damage, loss of myocardial architecture, edema, hemorrhage and the uniform presence of thrombi 1 hour post reperfusion. However, the transgenic pigs hearts appear relatively normal 2 hours post graft reperfusion. Endothelial cells appeared undamaged (with junctions still intact), there was little evidence of myocyte injury and there were only a few platelet thrombi. When the transgenic heart was rejected at 3 hours post-reperfusion, there were still regions of the tissue that appear undamaged, though the majority showed findings typical of hyperacute rejection. This was in contrast to uniform histologic changes typically observed in rejected normal porcine hearts.

Immunohistochemical staining of the transgenic and non-transgenic hearts for deposition of IgM and the complement component C3 showed a similar degree of perfusion with baboon serum and deposition of antibody in all pig hearts and indicate that activation of complement occurred. Tissues from the transgenic pig hearts reveal a marked decrease in deposition of membrane attack complex (MAC) in the 2 hour biopsy sample as compared to what was routinely seen in non-transgenic pig hearts transplanted into baboons at 1 hour post-reperfusion. Therefore, although human CD59 levels were many fold lower in porcine tissues than that seen in human tissues and detectable expression was focal in the transgenic heart, the protein present was sufficient to demonstrate functional activity as measured by the ability to inhibit MAC formation, and was able to confer protection against tissue damage in a xenogeneic setting. As the ability of low levels of human CD59 to inhibit MAC formation was measured on a background of presumably high levels of endogenous porcine CRP expression, the observed activity was consistent with the notion that these proteins are indeed species specific.

Analysis of transgenic mice and pigs which expressed a CD59 minigene (CD59 Minigene No. 1) indicated that the human CD59 protein was expressed on a subset of the cells where endogenous human CD59 expression is observed, and expression levels were substantially (at least 10-fold) lower than endogenous human levels. However, we showed that the protein was appropriately processed and, more importantly, retained its biological function as demonstrated by inhibition of membrane attack complex assembly. In an attempt to improve some of the deficiencies of CD59 Minigene 1, an altered version, Minigene 2, was constructed.

Example II

CD59 MiniGene No. 2

2.1 Construction of the CD59 MiniGene No. 2

Construction of CD59 minigene No. 2 was performed as follows. First, CD59 exon 2 was PCR-amplified using primers EX2-5 (5'-TACCCCGGGCATGTCCCCAAAGAGAGC-3') (SEQ ID NO:7) and EX2-3C (5'-CCGCTCGAGGCTGCTGTCACTATGACC-3') (SEQ ID NO:8) to generate a 1048 bp PCR product encompassing 0.52 Kb 5' of exon 2 and 0.43 Kb 3' of exon 2. Exon 2 and surrounding bases (125 bp 5' and 125 bp 3' of the 85 bp exon 2) were verified by sequence analysis. PCR amplification introduces a SmaI site at the 5' end of the PCR product and an XhoI site at the 3' end of the PCR product for cloning purposes. The next step was to PCR-amplify CD59 exon 3 using primers EX3-5 (5'-CACAGGAGCTCCAGTTGCAGGTTAGGAGG-3') (SEQ ID NO:9) and EX3-3C (5'-CGCAGGAATTCAGCTTGAGTCTCCTCAGG-3') (SEQ ID NO:15) to generate a 913 bp PCR product encompassing 0.27 Kb 5' of exon 3 and 0.53 Kb 3' of exon 3. Exon 3 and surrounding bases (50 bp 5' and 50 bp 3' of the 98 bp of coding sequence) were verified by sequencing. PCR amplification introduced an SstI site at the 5' end of PCR product and an EcoRI site at the 3' end of the PCR product for cloning purposes. The CD59 exon 4 was then isolated from a lambda clone designated 13.11bL (Tone et al., *J. Mol. Biol.* 227:971–976, 1992) as a 2.5 EcoRI fragment which included 0.61 Kb 5' of exon 4 and 1.7 Kb 3' of exon 4. Finally, CD59 exon 1 was isolated as an 8.5 Kb XbaI/SalI fragment from the CD59 Minigene No. 1 (originally isolated from a lambda clone 13.11bL) and included 4.5 Kb 5' of exon 1 and 4.0 Kb 3' of exon 1.

A vector was constructed with a specifically designed polylinker generated using oligonucleotides such that the following sites exist in this order: KpNI, NotI, XbaI, SmaI, XhoI, SstI, EcoRI, SalI, NotI. The polylinker was introduced into a pGem (Promega) backbone. The above genomic fragments were cloned as follows. First, the 913 bp SstI/EcoRI exon 3 PCR product was cloned into the SstI/EcoRI site of the vector. Then, the 1048 bp SmaI/XhoI exon 2 PCR product was cloned into the SmaI/XhoI site of the above. The next step was cloning the 2.5 Kb EcoRI fragment containing exon 4 into the EcoRI site of the above. Next, an 8.5 Kb XbaI/SalI fragment containing exon 1 was filled at the SalI site to create a blunt end and cloned into the XbaI/SmaI site of the above. Finally, all ligation products were verified by multiple restriction enzyme digests for orientation and single-copy insertions. The final 13 Kb product was isolated by NotI digestion (see FIG. 1).

2.2 Production of Transgenic Mice

The 13 Kb fragment was microinjected into fertilized mouse eggs to obtain transgenic mice. The founder mice were CS7BL/6 SJL $F_2$ crosses. Seven founder mice were born, and all expressed human CD59 on endothelial cells of various tissues. Extensive analysis was then performed on offspring from all lines.

2.3 Expression Analysis in Transgenic Mice 2.3.1 FACS Analysis

By FACS analysis, 85–99% of the RBCs from line 9-1 were positive for the human CD59 protein. This finding was consistent in all but one other mouse line analyzed. In contrast, no transgenic animals derived using the first CD59 minigene construct (CD59 Minigene No. 1) expressed human CD59 on RBCs. The peak mean value of expression of human CD59 on RBCs from the 9-1 CD59 transgenic mouse line was equal to or greater than that seen on human RBCs. FACS analysis demonstrated a level comparable to that seen on human RBCs.

2.3.2 Northern Blot Analysis

RNA analysis of tissues (liver, heart, kidney, muscle, skin, spleen and thymus) obtained from transgenic mouse line 9-1 offspring indicated that the CD59 RNA expression levels are at least 15- to 20-fold higher than that seen with the CD59 Minigene No. 1 and at levels approaching that seen in human tissues (see FIG. 1 and Table 4).

2.3.3 Immunohistology Analysis

Immunohistology for detection of human CD59 protein on liver, heart and kidney indicated that expression levels as well as cell and tissue type specificity mirrored that seen in human tissues. This was in contrast to what was observed using the CD59 Minigene No. 1 where expression was absent in kidney and on circulating blood cells, and very limited in liver.

2.4 Functional Analysis in Transgenic Animals

Function of the transgenic human CD59 protein was assessed by measuring protection afforded to RBCs from complement mediated lysis upon exposure to human serum. Significant protection was detected which could not be compared to the CD59 Minigene No. 1 since no expression was detectable on those RBCs. However, the protection detected using line 9-1 exceeds that seen using a CD59 P1 positive mouse available in the laboratory (see FIG. 2).

RNA and immunohistological analysis on offspring derived from 5 other founders give results comparable to that seen with the transgenic mouse line 9-1. One line has increased expression levels of both RNA and protein, and the others have slightly lower levels of human CD59 expression.

Analysis of mouse CD59 Minigene No. 2 transgenic lines indicated that the second minigene was vastly superior to CD59 Minigene No. 1 and preferable to the CD59 P1. Transgenic rates were higher for the minigene constructs as compared to the P1 clone, probably based upon the sizes of the respective constructs. Transmission of the respective genes to offspring was similar, but the CD59 Minigene No. 2 showed much better penetrance than either CD59 Minigene No. 1 or the CD59 P1. All lines (6/6) developed using CD59 Minigene No. 2 expressed the transgene in a consistent fashion.

Figure 3:
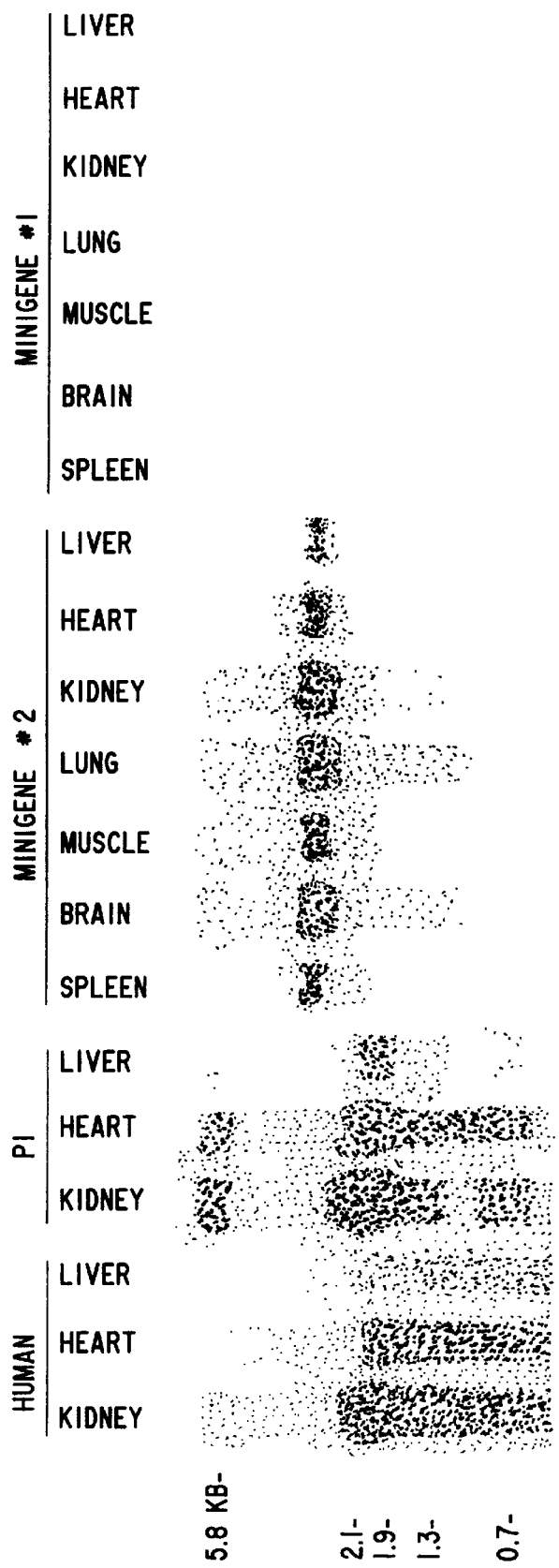
FIG. 3 represents a Northern Analysis of CD59 Transgenic Mice produced in accordance with the Invention. RNA from indicated human tissues, transgenic CD59 P1 mouse tissues, CD59 Minigene #2 mouse tissues, and CD59 Minigene #1 mouse tissues are analyzed by Northern Blot. All CD59 Minigene #2 mouse tissues analyzed thus far encode a 3.1 Kb CD59 message as compared to the 0.7, 1.3, 1.9, or 2.1 Kb messages possible based upon what is available for polyadenylation in the minigene construct. We have shown that the message contains an intact coding region and utilizes known polyadenylation sites. It appears that the alteration in the size of the transcript is due to aberrant spacing within intron 1. However, a functional human CD59 protein is produced from this transcript.

CD59 expression levels in CD59 Minigene No. 2 mice were consistently and significantly higher, and tissue and cell-type specificity reflected that seen endogenously, when compared to CD59 Minigene No. 1 transgenic mice. While 5 lines of transgenic mice developed using CD59 Minigene No. 1 expressed human CD59 at detectable levels, 4 of these lines had extremely low levels of RNA and protein. The mouse line expressing at the highest level was further characterized and this is the line represented in all comparisons to mouse lines developed using CD59 Minigene No. 2. As shown in the Northern analysis (FIG. 3) and densiometric scanning of this data (Table 4) mRNA levels in CD59 Minigene No. 2 mouse tissues are 15–20 fold higher than that seen in Minigene No. 1 mouse tissues. Comparison of CD59 Minigene No. 2 mouse tissue mRNA levels to that seen in CD59 P1 mice or in human tissues indicates that the expression levels are fairly similar. It should be kept in mind, however, that the highest expressing P1 mouse line, and the highest expressing CD59 Minigene No. 1 mouse line, are being compared to an intermediate expressing CD59 Minigene No. 2 mouse line.

Comparison of human CD59 protein levels on the different transgenic mouse lines (P1, CD59 Minigene No. 1 and CD59 Minigene No. 2) as well as that seen on human tissues (Table 5) shows that the levels of protein detected on tissues from CD59 Minigene No. 2 mice far exceeds that seen on the same tissues from CD59 Minigene No. 1 mice, and is comparable to what is seen in P1 mice and in humans.

Figure 2:
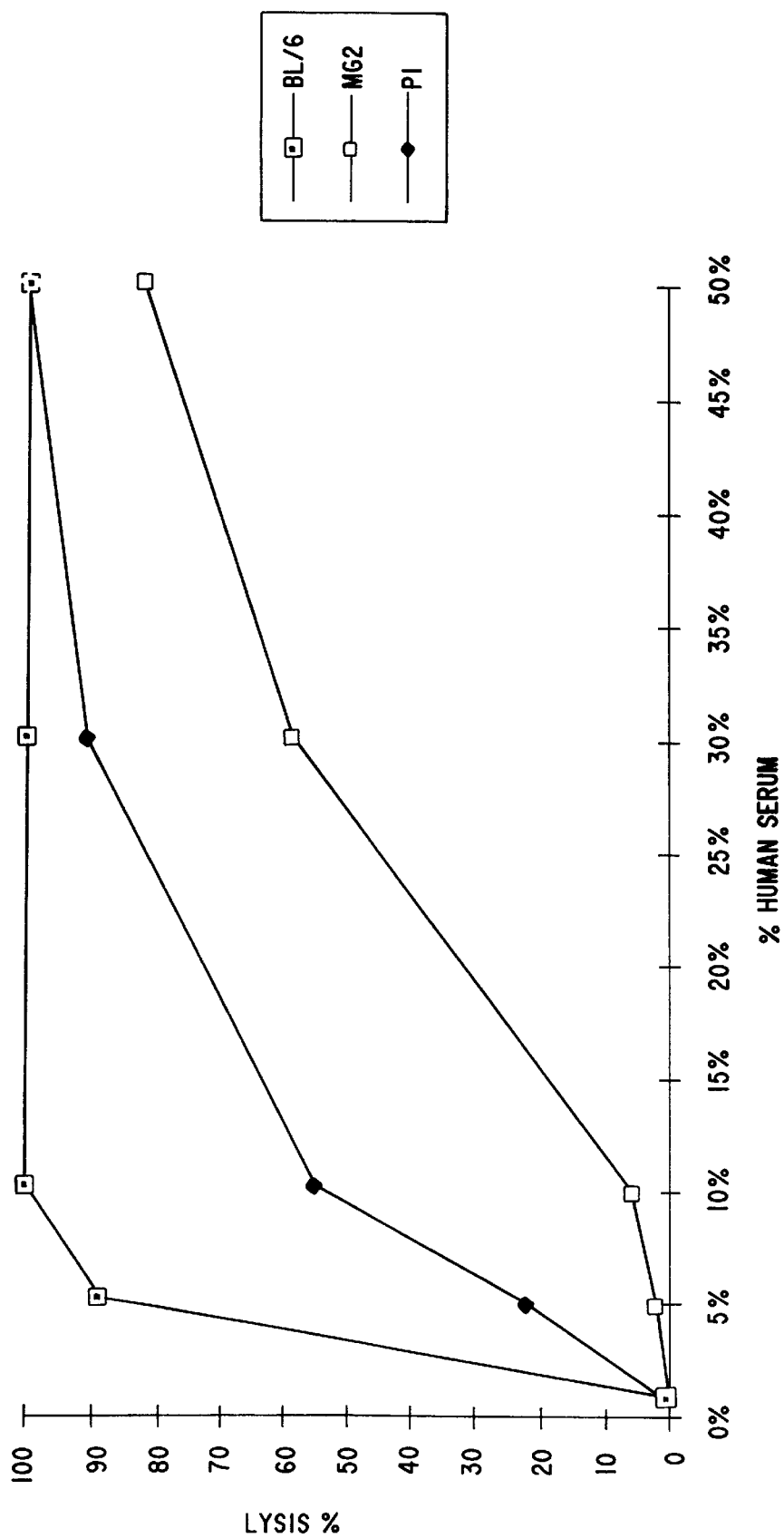
FIG. 2 relates to Transgenic Mouse RBC Complement Mediated Lysis. As observed in the drawing figure, the expression of human CD59 imparts protection to cells from complement mediated lysis upon exposure to human serum. One can detect this protective activity by measuring absorbance of hemoglobin upon lysis of RBCs after incubation with varying dilutions of human serum. While 50% of the non transgenic C57BL/6 mouse RBCs lyse at approximately 3% human serum, 50% lysis of RBCs from a CD59 Minigene 2 mouse is observed at approximately 27% human serum. This is in comparison to 50% lysis of CD59 P1 mouse RBCs lysing at about 9% human serum. Thus CD59 Minigene 2 mouse RBCs are approximately 10-fold more resistant to complement mediated lysis as compared to nontransgenic mouse RBCs and approximately 3-fold more resistant than CD59 P1 mouse RBCs.

The biological activity of human CD59 can be measured as a function of the protection conferred to cells such as RBCs upon exposure to human serum. Cell lysis is measured in this case as hemoglobin release. A functional analysis of human CD59 expressed on RBCs of CD59 Minigene No. 2 transgenic mice and on CD59 P1 transgenic mice is shown in FIG. 2. CD59 Minigene No. 2 RBCs are approximately 10-fold more resistant to complement mediated lysis than are non-transgenic RBCs from a C57BL/6 mouse, and are approximately 3-fold more resistant than RBCs from a CD59 P1 transgenic mouse. These figures are based upon the % human serum required to lyse 50% of the RBCs.

A summary of data compiled from co-injection of constructs into mice and pigs is shown in Table 6. An attempt was made to use the CD59 Minigene No. 1 construct as a cassette for expression of MCP as well as for DAF (inserted as a cDNA at the unique XhoI site in exon 1). However, no co-injections of CD59 Minigene No. 1/CD59 Minigene No. 1 (as a cassette) were done in mice. Co-injections into mice of complement regulatory protein (CRP) constructs utilizing cDNAs driven by heterologous promoters can be compared to CD59 P1 clones co-injected with MCP and DAF P1 clones. As can be seen, co-injection of various P1 clones into mice gave a frequency of 3.4% mice positive for 2 different transgenes. However, in all cases, upon breeding, the transgenes segregated, indicating that integration of the different transgenes had occurred on different chromosomes. Analysis of co-injection of smaller constructs into mice, however, indicates that while expected frequencies of double transgenics are obtained in comparison to CD59 P1 clones, in all cases double integrations of smaller transgenes were transmitted faithfully, indicating that co-integration had occurred.

Co-injection of various P1 clones into pigs gives a frequency of only 0.64% of the animals being transgenic for 2 different P1 genes. Thus far, one out of four founder animals has faithfully transmitted two P1 gene constructs as a unit to offspring. Co-injection of the CD59 minigene No. 1 and the CD59 Minigene No. 1 (as a cassette) into pigs gave rise to 2/49 (4.1%) transgenic animals. Both of these animals were transgenic for both genes, and both animals transmitted both genes to all offspring. Therefore, it can be concluded that the CD59 Minigene constructs co-integrated in both cases.

In conclusion, the CD59 Minigene No. 2 construct directs high level, tissue and cell-type specific expression of a functional human CD59 protein in transgenic animals which is far superior to that seen using CD59 Minigene No. 1. The overall data for the CD59 Minigene No. 2 constructs is comparable if not better than that seen using the CD59 P1 genomic clone. In addition, analysis of co-injection data indicates that a CD59 Minigene construct will be useful as a cassette in order to express other genes (i.e., other CRP) and subsequently co-inject these constructs in order to obtain an animal with 2 or 3 different transgenes, all of which will be transmitted to offspring. To date four pigs have been shown to express human CD59. Both FACS analysis on RBCs and immunohistochemical analysis of muscle biopsies have been positive for CD59 expression.

Example III

CD59 Minigene Cassette 3.1 Construction of the CD59 Minigene Cassette

A 1.3 Kb product was PCR-amplified using genomic DNA as a template to include approximately 1.34 Kb 5' of exon 2 and 16 bp 3' of the ATG in exon 2. The 3' primer was engineered to knockout the ATG in exon 2 by introducing an XbaI site. A SmaI site and a KpNI site were introduced at the 5' and 3' ends, respectively. Primers used were: 5'AGGTG-CACGGCCCA<u>CCGTGGCC</u>ACTAGTACTTACCCGGGGACCTCAGAC-CAC-3'(SEQ ID NO:11), with the SmaI site in bold (an SfiI site in italics was included for possible subsequent cloning steps) and 5'-CGGGGTACCCGTTA*GTCTAGA*AA<u>TGTGATTGTCCACAGAAC</u>-3' (SEQ ID NO:26) with the KpNI site indicated in bold, the XbaI site indicated in italics, and the underlined sequence corresponding to nucleotides complementary to CD59.

A second 0.512 Kb product was PCR-amplified using CD59 minigene No. 2 as a template. The product begins at the G which occurs just 3' to the ATG in exon 2 and extends 0.43 Kb 3' past the end of exon 2 into intron 2. A KpNI and an XhoI site were added as part of the primers to the 5' and 3' ends, respectively. The primers used were 5'-GGGGTACCAAGGAGGGTCTGTCCTGTTCG-3' (SEQ ID NO:13) with the KpNI site in bold, and 5'-CCGCTCGAGGCTGCTGTCACTATGACC-3' (SEQ ID NO:14) with the XhoI site in bold.

A third 3.5 Kb XhoI/NotI fragment was isolated from the CD59 minigene No. 2 which contains 0.27 Kb 5' of exon 3, exon 3, 0.53 Kb of the 5' of intron 3, 0.61 Kb of the 3' of intron 3, exon 4 and 1.7 Kb 3' untranslated sequence.

All three of the above fragments were ligated in this order: 1.35 Kb SmaI/KpNI - - - 0.512 Kb KpNI/XhoI - - - 3.5 Kb XhoI/NotI to create a 5.5 SmaI/NotI product containing a KPNI and an XbaI site inserted at the ATG of exon 2 resulting in destruction of the initiating methionine. This site serves as a cloning site to introduce cDNAs for expression on endothelial cells. Once a cDNA is inserted, the 5' containing CD59 exon 1 is added as an 8.5 Kb XbaI/SalI fragment with the SalI site filled to give a blunt end for ligation to the SmaI site.

3.2 Production of Transgenic Mice

The cDNA for DAF (or MCP) was inserted at the KPNI XbaI site of the CD59 minigene cassette, and the resulting construct is microinjected into fertilized mouse eggs to obtain transgenic mice. The founder mice identified as transgenic by Southern blot analysis are C57BL/6×SJL $F_2$ crosses. Extensive analysis is then performed on offspring from the founder mice.

3.3 Expression Analysis in Transgenic Mice 3.3.1 DAF Expression Using the Minigene Cassette All five of the founder transgenic mice generated using the DAF expression cassette expressed DAF on RBCs and two founders had expression levels comparable to human as measured by FACS. The DAF protein was functional as measured by the ability to protect transgenic mouse RBCs from complement mediated lysis. RNA and protein levels of human DAF were several fold lower in transgenic mouse tissue as compared to endogenous levels in humans.

3.3.2 MCP Expression Using the Minigene Cassette

Microinjection of the MCP expression cassette gave rise to 50 potential founders. Eight mice out of these 50 (16%) were identified as transgenic. Northern blot analysis of cardiac mRNA indicated that five of these eight founding lines expressed the appropriate sized transcripts; of those five, one line expressed MCP mRNA at levels comparable to that observed endogenously in human cardiac samples.

Example IV

Transgenic Animals Produced Utilizing P1 Clones 4.1 Identification and Purification of the P1 Clones Oligonucleotide pairs (Table 7), designed from previously published sequence data and corresponding to the 5' and 3' regions of CD59 and CD46 were used to screen, by polymerase chain reaction, a human genomic library constructed in the bacteriophage P1 (Genome Systems. St. Louis, Mo.). Using both sets of primers, clones were identified. High molecular weight plasmid DNA was isolated from the NS3529 strain of *Escherichia coli* by alkaline lysis and subsequently purified on a Qiagen-500 column (Chatsworth, Calif.). Inserts were mapped by restriction enzyme digestion, pulsed-field gel electrophoresis (PFGE) and Southern blot analysis.

Candidate fragments for microinjection were chosen based upon the amount of 5' and 3' flanking region existing in each clone.

To prepare fragments for microinjection, the clones were restricted with SfiI or MluI and the digestion mixture was size fractionated by PFGE. After being visualized by ethidium bromide staining, the fragments containing the clones were excised from the gel, purified, concentrated and analyzed for integrity.

4.2 Production of Transgenic Mice

Upon purification the fragments were individually microinjected into fertilized murine oocytes. Founder animals (C57BL/6×SJL $F_2$) were identified by Southern blot analysis and lines were established by backcrossing. Animals possessing two transgenes were generated by crossing offspring (e.g., CD59 and CD46 $F_1$ animals). From 27 potential founders, 5 (19%) were positive for CD59. MCP genomic clones (both the 60 kb and the 80 kb) produced 13 transgenic founders each, representing a transgenic rate of 29% and 15%, respectively. The 90 kb construct for DAF produced 6 positive transgenic from 19 $G_0$ mice. A 70 kb DAF construct produced 3 out of 18 transgenic founders (17%). Gene transmission to $G_1$ generation was 50% (2/4), 83% (10/12) and 69% (9/13) for CD59, 60 kb MCP and 80 kb MCP fragments, respectively (Table 8). Five out of 6 DAF founder also transmitted the gene to $G_1$ progeny. These data indicate that transgenic mice can be successfully made by microinjecting large genomic fragments and that these genes can be transmitted to subsequent generations.

4.3 Expression Analysis in Transgenic Mice

Heterozygote G1 animals were analyzed for expression by Northern analysis, immunochemistry and FACS analysis.

4.3.1 FACS Analysis and Quantitation

Protein expression on the surface of murine peripheral blood cells (erythrocytes and leukocytes) was assessed by indirect immunofluorescence. Cell surface expression was measured by flow cytometry using standard techniques.

4.3.2 Northern Analysis

Total cellular RNA was isolated from tissues, blood, or both and Northern blotting was performed. All probes were fragments radiolabeled with [-$^{32}$P] deoxy-CTP by random priming. Human total RNA samples served as positive controls and were purchased from Clontech (Palo Alto, Calif.).

4.3.3 Immunohistology Analysis

Tissues for immunofluorescence studies were embedded in O.C.T. (Lab Tak, Elkhart, Ind.), snap frozen in isopentane and stored at −80° C. until processing. Frozen tissue samples were prepared in a cryostat (Leica, Heidelberg, Germany). Sections were air dried, fixed with acetone and washed with phosphate buffered saline (PBS). Each section was incubated with monoclonal antibodies (mAbs) and the mAbs were detected with a double fluorochrome layer consisting of FITC-conjugated affinity isolated F(ab)'$_2$ secondary and tertiary antibodies. Tissue sections were washed with PBS after incubations and mounted with a p-phenylenediamine and glycerol solution. Background immunofluorescence was evaluated by preparing sections as previously described and omitting the primary antibody. The rat mAb, YTH 53.1, and the mouse mAb, MCA 695, (Serotec, Washington, D.C.) were used to detect CD59 and CD46, respectively. Additionally, a rhodamine conjugated antibody, provided by A. F. Michaels (University of Minnesota) was utilized to illustrate basement structures. Tissues were examined using a Leitz DMRB epifluoresence microscope (Wetzlar, Germany) and photographed (40×).

Five transgenic lines were identified that express CD59 mRNA as well as protein. A range of mRNA levels in hepatic, cardiac and renal tissue was observed in lines possessing the 70 kb genomic fragment that were basically similar to that seen in humans (detailed in Examples I and II). Transgenic mice expressed CD59 on the surface of endothelial cells in liver, heart and kidney as assessed by immunocytochemistry, and on RBCs as assessed by FACS analysis. These results demonstrate that by utilizing a large genomic CD59 clone tissue specific expression can be achieved.

Eight independent transgenic lines carrying the 60 kb MCP genomic fragment were positive for RNA and protein transgene expression. RNA expression was highest in the kidney and slightly lower in heart and liver. In three transgenic lines RNA levels were comparable to endogenous levels found in the respective human tissues. Protein was expressed on endothelial cells of the liver, heart, and kidney, with the highest expression seen in the liver. Additionally, FACS analysis demonstrated the presence of MCP on the surface of white blood cells. In contrast to CD59 and DAF, MCP protein expression in human circulating blood cells is absent on RBCs. The MCP transgene behaved similarly in that mouse RBCs were negative for human MCP expression. A similar scenario was observed for the 80 kb MCP genomic fragment in which the five lines analyzed were positive for human MCP RNA and protein expression. The tissue distribution for the two constructs was similar. These results imply that by utilizing these particular MCP genomic clones cell type and tissue specific expression can be achieved at levels comparable to those detected endogenously in humans (see Table 9 for details of protein expression on various tissues from two of the transgenic mouse lines).

4.4 Functional Analysis

Function of the transgenic human CD59 protein was assessed by measuring protection afforded to blood cells from complement mediated lysis upon exposure to human serum.

4.5 Transaenic Mice Possessing Multiple Human Complement Regulatory Genomic Clones Transgenic mice were generated which possess multiple human complement regulatory genomic clones. This was achieved by cross breeding individual lines expressing different complement regulatory proteins as well as by coinjection of the following clones: a) 70 Kb CD59+60 Kb MCP, b) 70 Kb CD59+90 Kb DAF, c) 60 Kb MCP+90 Kb DAF, and d) 70 Kb CD59+60 Kb MCP+90 Kb DAF (triple injection). Analysis of animals from double and triple injections of P1 clones indicates that co-integration of P1 genes did not occur. Mice carrying both CD59 and MCP P1 genes were obtained by crossbreeding two separate P1 lines. Analysis of these mice is underway to address the additive or synergistic effect of expression of two complement regulatory proteins in a transgenic animal.

4.6 Production of Transgenic Pig Lines Containing the P1 Clones

The transgenic pig lines were developed in much the same way as the transgenic mouse lines. Double and triple microinjections of CD59, DAF and MCP were performed. Seven hundred and ninety (790) potential founder pigs were born from March 1994 to March 1995. Of pigs positive for a single transgene, 9 were positive for MCP; 2 were positive for CD59; and 7 were positive for DAF. Three pigs were positive for CD59 and DAF, one pig was positive for MCP and CD59, and one pig was positive for MCP and DAF. A subset of founder pigs were analyzed utilizing blood samples, muscle biopsies or both.

Using the most sensitive method of detection of mRNA (i.e., RT-PCR) 3/3 MCP positive pigs analyzed were positive for MCP mRNA, 1/1 CD59 positive pig analyzed was positive for CD59 mRNA, and 5/5 DAF positive pigs analyzed were positive for DAF mRNA. Northern analysis (a less sensitive method of detection) of blood from the animals did not detect the respective messages. The MCP+ CD59 positive animal had MCP and CD59 messages detectable by RT-PCR, and only the message detectable by Northern analysis. Two CD59+DAF positive animals had both messages at levels detectable by RT-PCR with one animal having DAF mRNA and CD59 mRNA also detectable by Northern analysis. The third CD59+DAF animal had undetectable message by both methods. The MCP+DAF founder pig had MCP mRNA detectable by RT-PCR only. Refer to the summary below:

| DNA | PCR Positive | Northern Analysis Positve |
|---|---|---|
| MCP | +++ | |
| CD59 | + | |
| DAF | +++++ | |
| MCP + CD59 (1 pig) | +MCP; +CD59 | +MCP |
| CD59 + DAF (2 pigs) | +CD59; +DAF +CD59; +DAF | +CD59; +DAF |
| MCP + DAF (1 pig) | +MCP | |

The above data needs to be qualified by the observation that founder animals are frequently mosaic. While often undetectable in a founder animal, RNA specific to the transgene is frequently detectable upon transmission of the transgene to offspring. It has been our experience with the P1 transgenic mice that this is particularly true of blood samples. Collection of blood for analysis represents the least invasive procedure available for potentially valuable founder animals and therefore this is the method of analysis currently in use. In addition to the pigs listed above, 31 more pigs have been born and are awaiting testing. Extensive analysis must be performed on all offspring of the founder pigs to determine expression levels and tissue specificity.

Example V

Production of a Human CRP Locus Using YACs and Use Thereof 5.1 Production of Multi-gene YACs Large DNA fragments, like those described for the P1 genomic CD46, CD55, and CD59 genes, frequently give rise to high levels of gene expression with the appropriate tissue specificity. In some applications, such as xenotransplantation, it may be important to utilize multiple transgenes. With large DNA fragments it may be difficult however to use a simple co-injection strategy for the production of transgenic animals with more than one gene. Unlike smaller DNA fragments (>50 kb) that co-integrate at high frequency into a single site in the genome of the transgenic embryo, co-injection of larger genomic genes frequently results in multiple independent integration sites and an increased frequency of gene rearrangements. Transgenic animals produced through this process contain multiple transgene integration sites. On breeding, these transgenic animals independently segregate the transgenes to their offspring so that most offspring inherit only a fraction of the total number of co-injected transgenes. Furthermore, each integration site represents a disruption of the normal genomic structure, which increases the likelihood of creating deleterious mutations. Potential mutations are a particular concern in applications such as xenotransplantation where a transgenic organ is expected to survive for an extended period of time in a human recipient.

To circumvent these problems, and to create a framework on which additional genes relevant to xenotransplantation can be added, we have designed protocols to assemble a unique human complement regulatory locus, consisting of three large human genomic DNA fragments that encode for CD46, CD55 and CD59. The initial locus, consisting of genes for CD46, CD55 and CD59 will exceed 200 kb.

Recently it has become evident that large fragments of DNA, up to several hundred kilobases, can be successfully microinjected into fertilized eggs, and that these very large DNA-fragments remain intact and functional at a reasonable frequency. See Schedl et al., *Nuc. Acids Res.* 20:3073–3077 (1992); Gaensler et al., *Proc. Nat. Acad. Sci.* 90:11381–85 (1993); Schedl et al., *Nature* 362:258–261 (1993); and Gnirke et al., *Genomics* 15:659–667 (1993). This suggests then that a series of P1 sized genomic fragments could be combined into a single piece of DNA and then microinjected. This strategy would insure that the transgene locus, composed of multiple P1 sized DNA fragments, consisted of a defined structure and that all of the P1 genes in the locus integrate into a single genomic site. Because the genes are physically linked, this strategy also insures that each of the multiple genes that make up the transgene locus will be faithfully transmitted as a unit to subsequent generations.

5.1.1 Assembly of a Human CRP Locus

Since the P1 cloning system can only package DNA up to 100 Kb, it is necessary to use a yeast (YAC) cloning system (Burke et al., *Science* 236:806–812, 1987) to assemble a locus in excess of this size. We have described P1 genomic fragments that encode CD59, CD46 and CD55. Together, the three P1 genes sum to 200 Kb of DNA. This size can be easily accommodated by a YAC cloning system. The termini of each P1 genomic fragment is defined by a unique pair of restriction enzyme sites (Table 10). To facilitate assembly of these three genes we have modified the pYAC4 cloning vector to include a multiple cloning site that contains these restriction sites (FIG. 4). The order of the restriction enzyme sites within the multiple cloning site, allows for the sequential assembly of a locus consisting of the three P1 genes. The initial step is to clone the Mlu1 flanked 60 Kb CD46 P1 gene into the Mlu1 site of pSRY-1. This produces a YAC containing the MCP gene. It is preferred that the P1 insert be oriented such that transcription of MCP occurs from the TRP arm side. Similarly, the 70 Kb SfiI CD59 P1 gene is cloned into the SnaBI site to produce a second YAC containing the CD59 gene. Finally, a Not1 digested MCP-YAC and an SfiI digested CD59-YAC can be linked together with the Not1, SfiI CD55 P1 gene.

5.1.2 Production of YAC-MCP

High molecular weight plasmid DNA consisting of the P1 MCP clone is isolated by alkaline lysis and subsequently purified on a Qiagen-500 column (Chatsworth, Calif.). The DNA is digested to completion with the restriction enzyme Mlu1, extracted with phenol/chloroform (Riley et al., in *Techniques for the Analysis of Complex Genomes*, pages 59–79, 1992) and spot dialyzed against TE (10 mM Tris (pH 7.5), 1 mM EDTA). The plasmid pSRY-1 was digested with Mlu1 and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al., *Analytical Biochem.* 163:391–397 (1987). Transformants were initially selected on ura–plates, then on ura–, trp– plates. Genomic DNA plugs were subsequently made from the urea+, trp+ colonies and analyzed for the presence of a MCP containing YAC by PFGE and Southern blot hybridization. The integrity of the MCP DNA at the cloning site and orientation of the insert can be further determined using plasmid rescue.

5.1.3 Production of YAC-CD59

Because a SfiI restriction site contains 5 random bases the SfiI digest that defines the CD59 P1 gene produces an incompatible 3 base pair overhang that can not be directly cloned into the SfiI site of the SRY-I plasmid. For this reason we describe two methods for cloning the CD59 P1 gene into the pSRY-1 YAC. The first method is simply to clone the 70 Kb CD59 insert as a blunt ligation into the SnaB1 site of pSRY-1. High molecular weight plasmid DNA consisting of the P1 CD59 clone is isolated by alkaline lysis and subsequently purified on a Qiagen-500 column (Chatsworth, Calif.). The DNA is digested to completion with the restriction enzyme end, filled with T4 DNA polymerase, extracted with phenol/chloroform (Riley et al, 1992, see above) and spot dialyzed against TE (10 mM Tris (pH 7 5), 1 mM EDTA). The plasmid pSRY-1 was digested with SnaB1 and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al., (1987, see above). Transformants were initially selected on ura– plates, then on ura–, trp– plates. Genomic DNA plugs were subsequently made from the urea+, trp+ colonies and analyzed for the presence of a MCP containing YAC by PFGE and Southern blot hybridization. The integrity of the CD59 DNA at the cloning site and orientation of the insert can be further determined using plasmid rescue. This approach has proven to be difficult in this instance since it requires a blunt ligation. Additionally, the particular clone grows poorly making it difficult to isolate sufficient quantities of the CD59 P1 insert. Because of these problems we have developed the alternative strategy outlined below (Section 5.2).

5.1.4 Production of YAC-DAF

High molecular weight plasmid DNA consisting of the P1 DAF clone is isolated by alkaline lysis and subsequently purified on a Qiagen-500 column (Chatsworth, Calif.). The DNA is digested to completion with the restriction enzyme Not1 and SfiI, extracted with phenol/chloroform (Riley et al, 1992, cited above) and spot dialyzed against TE (10 mM Tris (pH 7.5), 1 mM EDTA). The plasmid pSRY-1 was digested with Not1, SfiI and BamH1, dephosphorylated with calf intestinal alkaline phosphatase and the 6.0 kb Trp arm and the 3.4 kb Ura arm were gel purified. The digested P1 DNA was then ligated overnight to a 10 molar excess of pSRY-1 arms and transformed into AB1380 spheroplasts as described by Burgers et al. (1987, above). Transformants were initially selected on ura– plates, then on ura–, trp– plates. Genomic DNA plugs were subsequently made from the urea+, trp+ colonies and analyzed for the presence of a DAF containing YAC by PFGE and Southern blot hybridization. The integrity of the DAF DNA at the cloning site and orientation of the insert can be further determined using plasmid rescue.

5.1.5 Assembly of the Three Gene Locus

To assemble the three gene locus the YAC-MCP chromosome is gel purified from yeast cells using PFGE, and the isolated band is digested with Not1. Similarly the YAC-CD59 chromosome is gel purified from yeast using PFGE, and the isolated band is digested with SfiI. These digested chromosome fragments are then ligated to equimolar amounts of the gel purified 70 kd Not1, SfiI DAF P1 insert and transformed into AB1380 spheroplasts. Transformants are initially selected on ura– plates, then on ura– and trp– plates. Genomic DNA plugs are subsequently made from the ura+, trp+ colonies and analyzed by PFGE and Southern blot hybridization for the presence of a 200 kd YAC containing all three genes.

5.2 Alternative Cloning Scheme

The formation of the CD59-YAC has been particularly difficult. This step involves a blunt ligation which is a far less efficient process. In addition the particular CD59 P1 clone grows poorly making it difficult to purify a sufficient quantity of CD59 insert for the blunt ligation. Due to these problems we have also used an alternative method of producing a CD59 containing YAC (Ketner et al.,1994, *Proc. Nat. Acad. Sci.* 91:6186–90). This approach relies on the high frequency of homologous recombination that occurs in yeast. In short, yeast spheroplasts are transfected with three pieces of DNA: the entire CD59 insert, a YAC-Trp arm containing a portion of the extreme 5' region of the CD59 insert and an YAC-Ura arm containing a portion of the extreme 3' region of the CD59 insert. The CD59-YAC results from two homologous recombination events, one between the 5' CD59 sequences in the Trp-YAC arm and the homologous 5' region of the CD59 P1 gene and a second event between the 3° CD59 sequences in the Ura-YAC arm and the homologous 3' region of the CD59 P1 gene (FIG. 5). To use this approach we have isolated the 5' and 3' terminal portions of the CD59 P1 insert by plasmid rescue and partially sequenced these subclones. From this analysis a series of oligonucleotide primers for PCR were produced (Table 12). Primer pairs CH-1 and CH-2 contain a Not 1, SfiI (CH-1) and BamHI restriction sites and amplify a 1.4 kb fragment from the 5' terminus of the CD59 P1 gene. This fragment is cloned into pSRY-I as a Not1, BamHl fragment. The resulting plasmid contains the 6 kb Trp-CEN-ARS YAC arm along with the 1.4 kb 5' CD59 insert. For the 3' end of the CD59 P1 insert, a 1.2 kb PCR product with SnaBl and HincII was amplified using primers ED-1 and ED-2. This PCR product was blunt cut into the SnaB1 site of SRY-1. The orientation of the 1.2 kb 3' fragment was confirmed by sequencing the junctions of the insert. To assemble the final CD59 YAC, three pieces of DNA were transfected into AB 1380. The CD59 P1 DNA, linearized with Not1, was cotransfected with equimolar quantities of BamHI digested 5' CD59-Trp-YAC arms and SnaB1, BamHI digested 3' CD59-Ura-YAC arms. Transformants were initially selected on ura– plates, then on ura–, trp– plates. Genomic DNA plugs were subsequently made from the ura+, trp+ colonies and analyzed for the presence of a CD59 containing YAC by PFGE and Southern blot hybridization. The integrity and orientation of the CD59 DNA within the YAC can be further determined using Southern blot analysis, plasmid rescue or PCR amplification across the 5' and 3' junction domains. Transformants with the correct structure were isolated at high frequency (Table 11).

5.2.1 Assembly by Homologous Recombination

The use of homologous recombination to subclone the P1 genes into YAC vectors is a general approach that can be used to produce MCP and DAF containing YACs, and to facilitate the sequential assembly of a triple gene YAC containing all three complement regulatory genes, or any other additional genes. FIG. 5 outlines how the triple gene YAC can be sequentially assembled. For this approach the extreme 5' and 3' fragments of the P1 genomic CRP genes must be isolated (FIG. 5A). These fragments can be isolated by plasmid rescue, subcloning, PCR amplification or any number of standard techniques. To facilitate homologous recombination in yeast these fragments should be unique sequences, devoid of repetitive elements, and approximately 500–2000 base pairs in length. The characteristics of the terminal fragments of CD59, MCP and DAF are presented in Table 13. The sequential assembly of a three gene YAC also requires the use of three selectable auxotrophic yeast marker genes. For our purposes we have used the auxotrophic markers Ura3, Trp1 and Lys2, but other combinations of markers are possible depending on the genotype of the yeast strain being used. The Ura3 and Trp1 markers arms were derived from pSRY1. The Lys2 marker is a 4.5 kb Hind3 subclone of pDP6 (Fleig, et al., 1986, *Gene* 46:237–245) which we added to the 700 bp Hind3, BamHI telomere seed sequences of pSRY-1 to produce a functional Lys2-YAC arm.

The sequential assembly of a YAC chromosome that contains all three human complement regulatory genomic genes begins with the addition of the 5' terminal fragment from the MCP gene, to the CD59-YAC described above. To make this addition the 3' terminal fragment of CD59 and the 5' terminal fragment of MCP are attached to each other and inserted into a Lys2 YAC arm. In this 3' CD59-5' MCP-Lys2 YAC arm the 3' CD59 sequences serve to target the site of homologous recombination so that when this DNA is transfected into the CD59-YAC containing yeast strain a homologous recombination event between the 3' CD59 sequences effectively deletes the Ura3 marker and replaces it with the Lys2-YAC arm (FIG. 5B). Transformants are initially selected for a functional Lys2 gene using lys– media. Clones are then placed under triple selection using lys–, trp– media which contains 5-fluoroorotic acid (FOA). This media simultaneously selects for the presence of functional Trp1 and Lys3 genes and the addition of FOA selects against a functional Ura3 marker. Yeast clones are further characterized by PFGE and differential Southern blot hybridization analysis using probes to Trp1, Lys2, CD59 and 5' MCP. Although only a few clones were analyzed, transformants with the correct structure and genetic behavior were isolated at high frequency (Table 11).

To add the rest of the MCP genomic DNA to the new CD59-5' MCP-Lys2-YAC the 1.3 kb Nco1, Mlul3' terminus of the MCP gene was blunt ligated to a Ura3-YAC arm. This construct was linearized by restriction digest, and cotransfected with Mlul1 digested MCP-P1 DNA into the CD59-5' MCP-Lys2-YAC containing yeast strain (FIG. 5C). Transformants are initially selected for a functional Ura3 gene using ura– media. Clones are then placed under triple selection using ura–, trp– media which also contains α-Aminoadipate (α-Ap). This media simultaneously selects for the presence of functional Trp1 and Ura3 genes and the addition of α-Ap selects against a functional Lys2 marker. Homologous recombination events within the 5' and 3' MCP sequences yield a new chromosome that contains both the CD59 and MCP complement regulatory genes flanked by Trp1 and Ura3 auxotrophic markers. Yeast clones are further characterized by PFGE and differential Southern blot hybridization analysis using probes to Trp1, Ura3, CD59 and MCP. Transformants with the correct structure were isolated at high frequency (Table 11).

The addition of the third gene, DAF, is accomplished in an analogous manner (FIG. 5D). The 1.3 kb 3' portion of the MCP genomic gene was added as an EcoR1 fragment to the plasmid that contained the 2.2 kb 5' portion of the genomic DAF gene. These two gene fragments were then added to the Lys2-YAC arm and transfected into the CD59-MCP-YAC double gene YAC. Through lys– selection and subsequent lys–, trp–, FOA triple selection we derived the CD59-MCP-5' DAF-Lys-YAC clone. The remainder of the DAF genomic gene was integrated to produce the triple gene YAC by cotransfecting the 70 Kb Not1-Sfi1 DAF genomic DNA with a 0.8 kb 3' DAF fragment attached to a Ura3 YAC arm. After the appropriate selection steps, yeast clones were analyzed by PFGE and differential Southern blot hybridization.

This three gene locus can be used to produce transgenic pigs expressing high levels of all three human complement regulatory genes. This new locus is advantageous over individually injected P1 genes, since all three genes are now physically linked prior to injection, and therefore are expected to integrate as a single locus. Moreover, since this unique locus is propagated as a YAC, the homologous recombination techniques described above can be used to make further additions to the locus. For example genes that mask or reduce the level of the gal epitope, including but not limited to nucleic acid coding for $\alpha(1,2)$FT, $\alpha(2,6)$ST, or $\beta(1,3)$NAGT, can be added, resulting in a locus that could both reduce the level of the major xenogeneic antigen, and control human complement activation. Further additions to the locus could be made, as the development of porcine xenogeneic organ donors progresses. For example, additional human genes that affect vascular rejection (e.g., thrombomodulin, protein C, factor H, tissue factor, urokinase plasminogen activator, ectoATPase, inhibitor of NFkb) or human genes that may affect cellular rejection (e.g., IL-4, IL-10, TGF-$\beta$, agents that block co-stimulatory molecules CD28 and CD40, soluble receptors to block cytokine actions such as soluble IL-2 or IFNg receptors) or genes that might be used to destroy porcine antigen presenting cells (such as a CD2 or CD45 regulated gene encoding Herpes simplex thymidine kinase) could also be added to this locus using the methods described above. All of these genes need not be large genomic DNAs, but could be well characterized minigene or any other genetic constructs.

5.3 Generation of Transgenic Animals

YAC constructs are prepared for microinjection using well known methods. The yeast chromosomes including the YAC construct are separated using pulse field gel electrophoresis(PFGE), which is designed to resolve very large DNA molecules. To isolate a 160 kb YAC a 1% SeaPlaque GTG low melt agarose (FMC Corp.) pulse field gel, run at 14° C., 6 volts/cm$^2$ for 20 hours with a 120° switch angle and 2–10 second switch times is used. The isolated YAC chromosome is cut from the gel and the agarose gel slice is equilibrated in injection buffer (10 mM Tris(pH 7.5), 0.1 mM EDTA, 100 mM NaCl, 30 $\mu$M spermine and 70 $\mu$M spermidine). The agarose gel slice is melted at 65° C. and digested with gelase (Epicenter Technology) at 37° C. for 3 hours. The digested agarose is then transferred, using a wide bore pipette tip to a Micron 10 concentrator (Amicon), where the DNA is concentrated by repeatedly centrifuging at 5,000 g for 15 minutes, until the entire content of the original gel slice is reduced to a 20–50 $\mu$l volume. The integrity of the YAC DNA can be checked on pulse field gel prior to microinjection.

Microinjection of the DNA construct is then performed as previously described in this application. Analysis of the transgenic animals and their offspring are conducted according to methods previously described in this application.

Example VI

Use of Glycosyltransferases to Reduce Gal Epitope Levels

Recent studies have indicated that antibody mediated rejection is initiated by the binding of xenoreactive natural antibodies (XNAs) to the Gal epitope. See, e.g., Sandrin et al., *P.N.A.S.* 90:11391–11395 (1993). The Gal epitope is produced by a glycosyltransferase, specifically $\alpha(1,3)$ galactosyltransferase or $\alpha(1,3)$GT. The Inventors have sought to modify the expression of the Gal epitope by manipulating the pathway which leads to production of this epitope. Specifically, the Inventors have cloned other glycosyltransferases and expressed them in animals and/or tissue culture cells in order to create competition for the substrate utilized by $\alpha(1,3)$GT and thus reduce expression of the Gal epitope.

6.1 Cloning and Expression of $\alpha(1,2)$FT in Tissue Culture Cells

Figure 6:
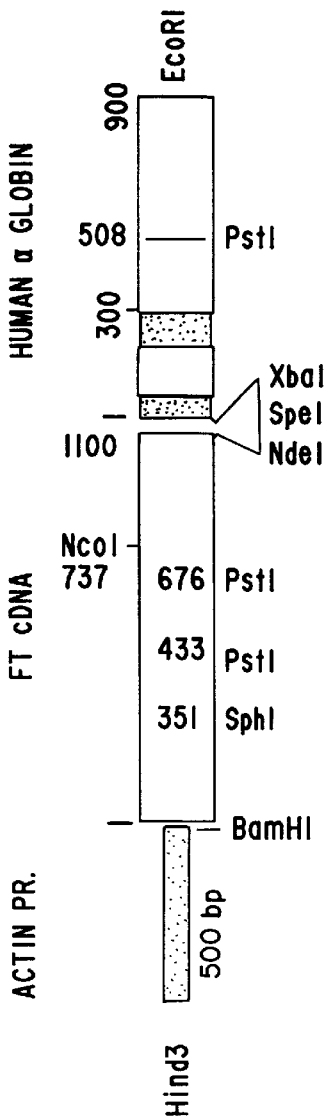
FIG. 6 is a schematic representation of the cDNA expression construct #876 used in accordance with the present invention.
Figure 7:
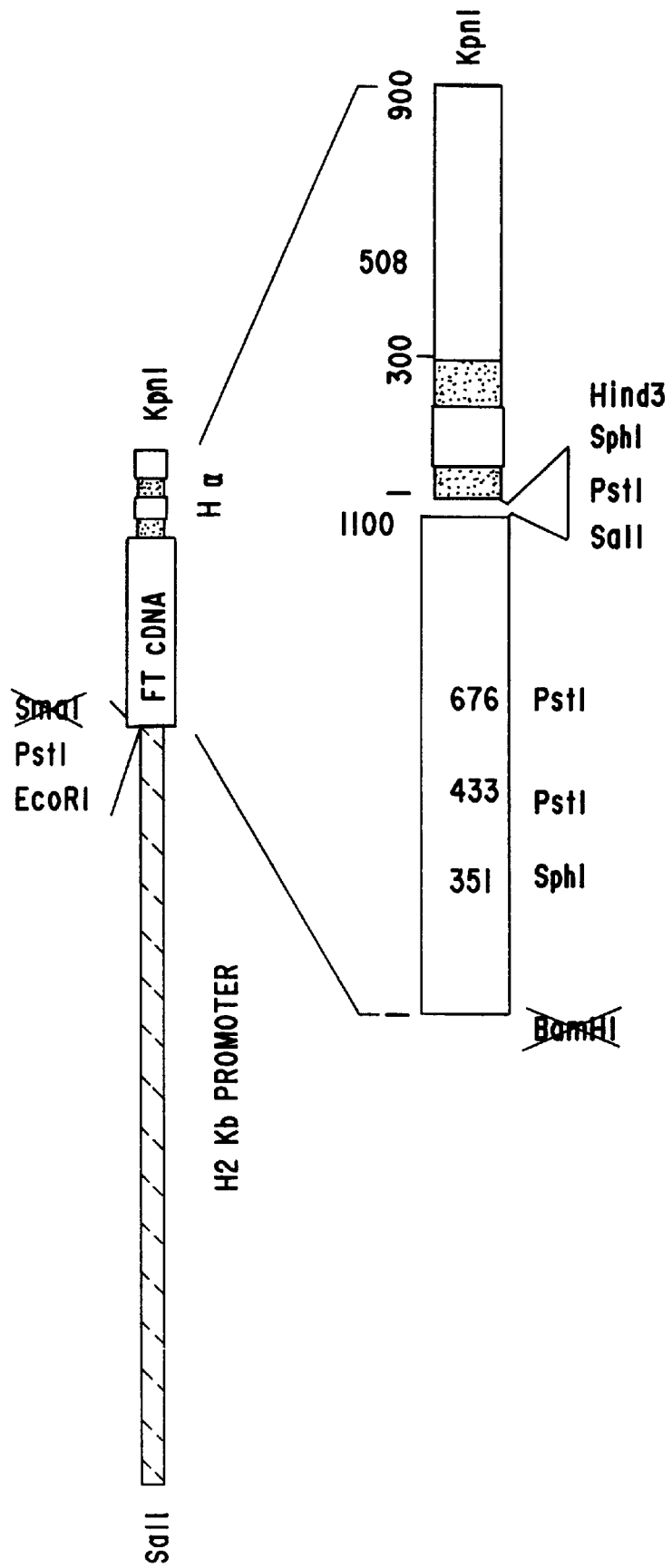
FIG. 7 is a schematic representation of the cDNA expression construct #881 used in accordance with the present invention.

Porcine $\alpha(1,3)$GT cDNA (1.1 kb) was obtained by RT-PCR using total RNA from porcine aortic endothelial cells and First strand cDNA synthesis kit (Pharmacia). The degenerate PCR primers were based on mouse and bovine GT sequences, as set forth, e.g., in Larsen et al., *J. Biol. Chem.* 265:7055–7061 (1990) and Joziasse et al., *J. Biol. Chem.* 264:14290–14297 (1989). The cDNA was cloned into a eukaryotic expression vector pRex10 (pRex10/GT) containing enhancer and promoter sequences from Rous sarcoma virus long terminal repeat (RSV-LTR) and the neomycin resistance gene. The human $\alpha(1,2)$FT cDNA was cloned by RT-PCR using total RNA from A431 cell line, as disclosed in Larsen et al., *P.N.A.S.* 87:6674–6678 (1990). The sense primer (TTTGGATCCTCGGCCATGTGGCTCCGGAGCCATCG) (SEQ ID NO:1) flanked the ATG initiation codon and included a BamH I site. The antisense primer (AAAGTCGACTCAAGGCTTAGCCAATC) (SEQ ID NO:2) flanked the TGA stop codon and included a Sal I site. The 1.1 kb CDNA was cloned into pRex 10 (pRex10/FT) to express $\alpha(1,2)$FT in tissue culture cells. For generation of transgenic animals expressing $\alpha(1,2)$FT, the $\alpha(1,2)$FT cDNA was cloned into vectors containing a 500 bp chicken actin promoter (#876), see FIG. 6, or a 4.3 kb H2k$^b$ promoter (#881), see FIG. 7. The splice and polyadenylation sequences were provided by a 900 bp HindIII/KpnI fragment of human globin gene containing sequences downstream from the second exon.

Prior to the generation of transgenic animals containing the $\alpha(1,2)$fucosyltransferase (or $\alpha(1,2)$FT) gene in accordance with the present invention, Chinese Hamster Ovary (CHO) cells were used as a model system to determine whether $\alpha(1,2)$FT would compete with $\alpha(1,3)$GT for modification of glycoproteins and glycolipids. These cells are deficient in both $\alpha(1,3)$GT and $\alpha(1,2)$FT but do express N-lac that can act as an acceptor for both of these enzymes. CHO cells were transfected with the porcine $\alpha(1,3)$GT cDNA (pRex10/GT). Porcine $\alpha(1,3)$GT cDNA (1.1 kb) was obtained by RT-PCR using total RNA from porcine aortic endothelial cells and First strand cDNA synthesis kit (Pharmacia).

For the cell culture and transfection steps, cell culture and transfection reagents were obtained from Gibco BRL. Chinese Hamster Ovary (CHO-K1) cells (ATCC, CCL-61) were maintained in F-12 (HAM) medium with glutamax-1 supplemented with 10% fetal bovine serum. The transfections were done with Lipofectamine using 1–2 $\mu$g of supercoiled plasmid DNAs (pRex10/GT or pRex10/FT) according to manufacturer's instructions.

Assays for cell surface antigen expression were performed as described in Collins et al., *Xenotrans.* 1:36–46 (1994). Briefly, the cells in 96 well plates were fixed with 1% glutaraldehyde and then incubated with different concentrations of lectin-biotin conjugates (E.Y. labs) for 1 hour at room temperature. The cells were washed with PBS and incubated with 1:1000 dilution of strepavidin-HRP (Pierce) for one hour. The plates were developed using 150 ul/well of HRP-substrate solution in the dark for 5–10 minutes. The reaction was stopped with 50 ul of 2M $H_2SO_4$. The plates were read at 505 nm on Molecular Devices Vmax microplate reader.

Total cellular protein extracts obtained in conjunction with these experiments were prepared as described in Hanasaki et al., *J. Biol. Chem.* 269:10637–10643 (1994). Briefly, $5 \times 10^6$ cells were incubated for 10 minutes at 4° C. in 0.8 ml of cell lysis buffer (0.16M NaCl, 1 mM EDTA, 1% NP40, 2.5 mM deoxycholate, 0.1% SDS, 10 μg/ml aprotonin, 10 μg/ml leupeptin and 20 mM Tris-HCl, pH 8.0). Cells were scraped into Eppendorf tubes and spun at 12000×g for 5 minutes, supernatants were removed, and the protein concentrations were determined.

Figure 8:
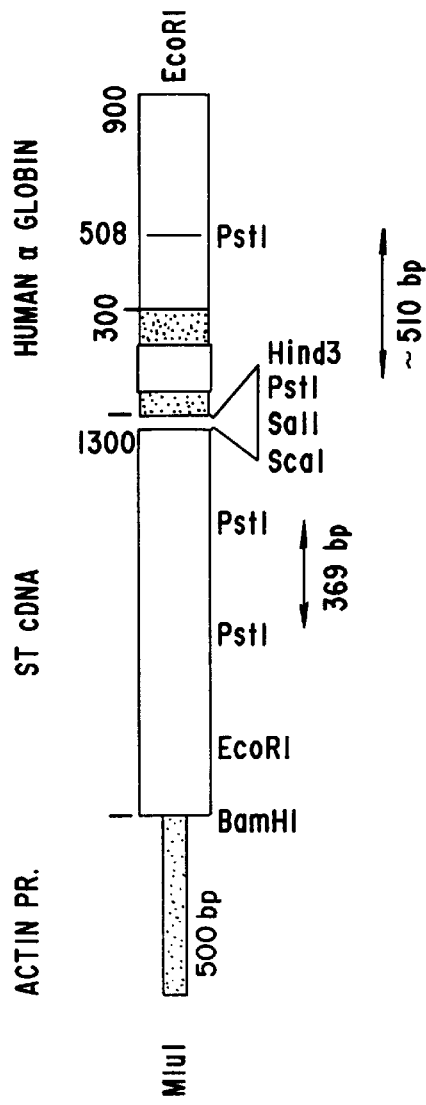
FIG. 8 is a schematic representation of the cDNA expression construct #882 used in accordance with the present invention.

The expression of $\alpha(1,3)$GT in transfected cells was assessed by a lectin binding assay using the lectin *Griffonia simplicifolia* 1 isolectin B4 (GS-1-$B_4$) which recognizes the same terminal structure Gal$\alpha$(1,3)Gal as recognized by the XNAs. Analysis of one representative clone (CHO/GT) is shown in FIG. 8. While untransfected CHO cells do not bind the lectin GS-1-$B_4$, CHO/GT cells clearly bind the lectin and therefore produce the gal epitope.

To determine the extent to which $\alpha(1,2)$FT would compete with $\alpha(1,3)$GT for N-lac, the CHO/GT cells were transfected with pRex10/FT. A pool of transfected cells (CHO/GTFT) was selected and analyzed for $\alpha(1,3)$GT and $\alpha(1,2)$FT expression by lectin binding assay. The expression of $\alpha(1,2)$FT was determined based on the binding of a lectin *Ulex europaeus* I (UEA-I) which detects the H-antigen. As shown in FIG. 8, CHO/GTFT cells which express high levels of H-antigen display up to a 70% reduction in GS-1-$B_4$ binding compared to CHO/GT. No difference in the level of $\alpha(1,3)$GT mRNA or gene copy number was observed between CHO/GT and CHO/GTFT cell lines suggesting that decreased binding of GS-1-$B_4$ (and thus low $\alpha(1,3)$GT activity) is due to competition at the enzyme level.

Next, the glycosylation of membrane proteins, which may be more important than glycolipids in xenotransplantation (see Platt et al., *Transplantation* 57:327–332 (1994)), was examined by lectin blotting. The lectin blotting was performed as described in Hanasaki et al., *J. Biol. Chem.* 269:10637–10643 (1994), with minor modifications. In the method used, protein samples (10 μg) were resuspended in sample buffer (50 mM Tris-HCl pH 6.8, 100 mM 2-mercaptoethanol, 2% SDS, 0.2% Bromophenyl, and 10% glycerol), heated for 3 minutes at 100° C. and loaded onto a 7.5% SDS gel. After electrophoresis, the proteins were transferred to Immobilon-P membranes (Millipore) at 100 volts for 2 hours. Following transfer, the membranes were rinsed twice with Tris-buffered saline (TBS: 150 mM NaCl, 1 mM CaCl(2), 1 mM MgCl(2), 1 mM MnCl(2) and 20 mM Tris-HCl, pH 7.5)/0.1% Tween. After blocking for 1 hour with 1% ovalbumin/TBS, the membranes were incubated for 1 hour at 4° C. with 3 μg/ml of lectin-biotin conjugates in 1% ovalbumin/TBS/0.1% Tween. Membranes were washed 3 times with TBS/Tween and incubated for 1 hour with 1 μg/ml of strepavidin-HRP in 1% ovalbumin/TBS. After washing, the membranes were developed using a chemiluminescent detection kit (ECL Western Blotting Detection Kit, Amersham Corp.) according to manufacturer's instructions.

Figure 9A:
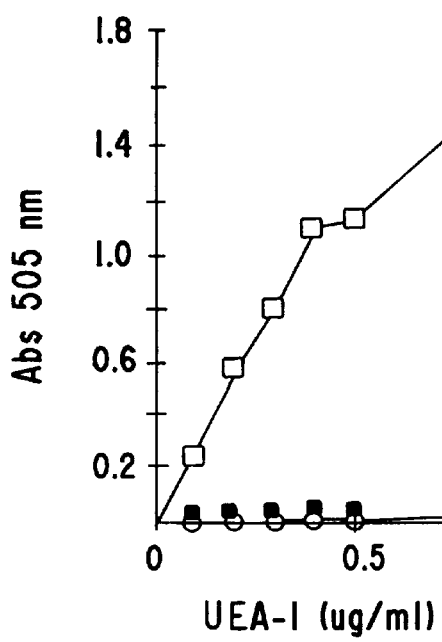
FIG. 9 is a graphic representation of the binding of UEA-I or GS-1-$B_4$ lectin to untransfected CHO cells (or CHO-N cells, represented as ■), CHO cells transfected with the $\alpha$(1,3)GT gene (or CHO/GT cells, represented as ○), and CHO/GT cells transfected with the $\alpha$(1,2)FT gene (CHO/GTFT cells, represented as □), as measured by a lectin binding assay.
Figure 9B:
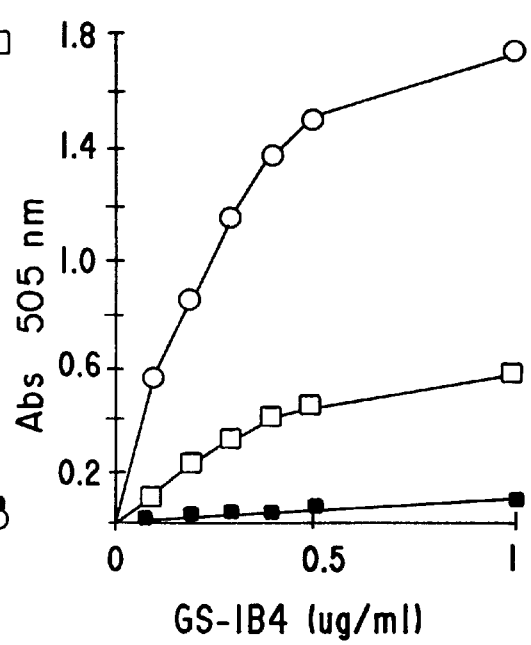
Figure 11:
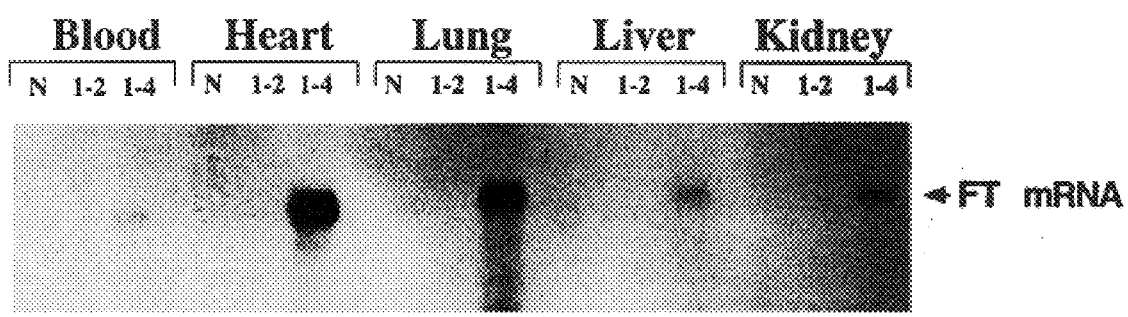
FIG. 11 is a representation of the Northern analysis of $\alpha$(1,2)FT mRNA produced in transgenic mice in accordance with the present invention.

Expression of porcine $\alpha(1,3)$GT in CHO cells (CHO/GT) resulted in galactosylation of proteins mostly in the >60 kDa range (see FIG. 9, GS-1-$B_4$ panel). Expression of $\alpha(1,2)$FT in CHO/GT cells (CHO/GTFT) abrogated GS-1-$B_4$ binding to these proteins resulting instead in the expression of the H antigen (fucosylated proteins).

These results clearly suggested that $\alpha(1,2)$FT can compete with porcine $\alpha(1,3)$GT and that $\alpha(1,2)$FT could be used to reduce the level of the gal epitope in transgenic animals.

6.2 Cloning of $\alpha(2,6)$ST

Alpha (2,6)sialyltransferase was cloned by RT-PCR using total RNA from rat liver, as disclosed in Weinstein et al., *J. Biol. Chem.* 262:17735–43 (1987). The human sequence is 80% identical to the rat sequence. The sense primer (AATATTAGCCAGAAGCAG) (SEQ ID NO:17) included a SspI site. The antisense primer (TCGAGTACTCAACAACGAATGTT) (SEQ ID NO:18) flanked the TGA stop codon and has a Sca1 site. The 1.3 kb cDNA was cloned into pRex10 (pRex10/RST) to express in tissue culture cells using methods similar to those described in section 6.1, above. Comparable analysis was performed.

6.3 Expression of $\alpha(1,2)$FT in Transgenic Animals

The concept of using $\alpha(1,2)$FT to compete with $\alpha(1,3)$GT in mice which normally express the gal epitope on endothelial cells and on secreted glycoproteins such as thyroglobulin, fibrinogen, etc. was tested using suitable promoters. The chickβ-actin (AcFT #876) and the murine H2 $k^b$ promoter (H2FT, #881) were used to drive the expression of the $\alpha(1,2)$FT cDNA on endothelial cells (as observed in FIGS. 6 and 7). These promoters have been used in previous experiments to express human CD59 and DAF in transgenic mice and pigs resulting in widespread tissue expression including but not limited to endothelial cells. See Byrne et al., *Transplantation* 60:1149–1156 (1995).

The transgenic mice were prepared by injecting the appropriate DNA into male pronuclei of fertilized mice oocytes (C57BL/6), as set forth in Logan et al., *Meth. Enzym.* 231:364–373 (1994). The eggs were then transferred into pseudo pregnant females in order to obtain the transgenic mice.

By PCR and Southern analysis, 3/29 and 7/30 of the mice produced by this process had incorporated the construct #876 (AcFT) and #881 (H2FT) respectively, into their genome. Transgenic mice carrying construct #881 were analyzed for the expression of the $\alpha(1,2)$FT gene. In addition, a Northern blot analysis was conducted in which total RNA was prepared animal tissues using RNA STAT-60 (TEL-TEST) according to manufacturer's instructions. RNA (10 μg) was fractionated on a 1% agarose gel containing formaldehyde and transferred to a nylon membrane (ICN Biomedical). The probes were prepared using the Ready To Go Kit (Pharmacia) and the hybridization was performed.

The Northern blot analysis showed that $\alpha(1,2)$FT mRNA was present in all the tissues examined including heart and kidney, as observed in FIG. 10. No $\alpha(1,2)$FT signal was detected in any of the tissues from normal mice. The RNA from mouse 1-2 which contained a truncated transgene was also negative for the $\alpha(1,2)$FT message.

The expression of the H antigen in transgenic mice was analyzed by lectin staining of tissue sections and fluorescence microscopy. In preparing the samples for immunohistochemical staining, after snap freezing in pre-cooled isopentane, the tissue samples were stored at −80° C. until use. Immunohistochemical staining with FITC lectins was then carried out as described in Platt et al., *J. Exp. Med.* 155:17–30 (1982). As shown in FIG. 11A–D, the transgenic mouse (1-4) exhibited a high level of expression of H antigen as indicated by the binding of UEA-I to myocytes and endothelial cells in heart (see panel C of FIG. 11), while no binding was observed in the tissues of normal mice (see panel A). Similar results were obtained with kidney, lung, liver and spleen from transgenic versus normal mice with expression being predominantly, though not exclusively, endothelial in nature.

To determine if the expression of α(1,2)FT in tissues from transgenic mice was associated with reduction of the gal epitope, tissue sections of α(1,2)FT transgenic and control mice were stained with the lectin GS-1-B$_4$. As indicated in FIG. 11C, there was a dramatic reduction in the level of GS-1-B$_4$ binding in the heart of the α(1,2)FT transgenic mouse as compared to the control mouse (see FIG. 11B). This result suggests that the expression of the α(1,2)FT gene causes a dramatic decrease in the level of Galα(1,3)Gal.

6.4 Expression of α(2,6)ST in Transgenic Animals

The concept of using α(2,6)ST to compete with α(1,3)GT in mice which normally express the gal epitope on endothelial cells and on secreted glycoproteins such as thyroglobulin, fibrinogen, etc. was tested using a suitable promoter, specifically the chick βactin promoter. Expression of α(2,6)ST in transgenic animals was obtained by using a construct containing 500 bp of chick βactin promoter (#882), as shown in FIG. 8.

The transgenic mice were prepared by injecting the appropriate DNA into male pronuclei of fertilized mice oocytes (C57BL/6), as set forth in Logan et al., Meth. Enzym. 231:364–373 (1994). Transgenic mice were identified by Southern analysis; 17 out of 103 mice were positive for the transgene. The transgenic mice were then mated to each other and the F1 progeny (or the founder animals) were analyzed for α(2,6)ST mRNA by Northern analysis of tissue RNA. In one line, (9-8X14-8) high level expression was observed in skeletal muscle and heart. To determine if expression of α(2,6)ST resulted in down regulation of the Gal epitope and reduced binding, the endothelial cells were prepared from a normal and α(2,6)ST transgenic heart and stained with GS-1-B$_4$ or XNA and analyzed by FACS. The ECs were labeled with anti-CD31 antibody. As was experimentally determined, there is reduced binding of both the GS-1-B$_4$ and XNA to ECs from transgenic heart EC. In addition, the transgenic EC also exhibited reduced complement mediated lysis as compared to normal mouse.

6.5 Expression Analysis of α(1,2)FT in Transgenic Mice

To determine whether expression of α(1,2)FT results in reduced binding of xenoreactive antibodies, the endothelial cells (ECs) from a normal and an FT transgenic mouse heart were isolated and incubated with XNAs and analyzed by flow cytometry. To obtain this analysis, freshly harvested organs (heart and liver) were minced and digested in dispase solution (Becton Dickinson Labware) for 90 minutes at 37° C. with gentle shaking. The resultant cell suspension was washed and counted using a Coulter Z1 Analyzer. Aliquots of 4×10$^6$ cells were used for immunofluorescent staining, utilizing a three step procedure. First, the cells were incubated for 30 minutes on ice, with 10 μg of xenoreactive natural antibodies, isolated as described in Parker et al., J. Immunol. 53:785–794 (1994), with or without the addition of 5 mM Galactobiose (V-Labs). Cells were washed twice and incubated for 30 minutes on ice with 5 μg of biotinylated mouse anti-human IgM (Pharminigen). Also, 10 μg of FITC labeled sheep anti-human Factor VIII (Serotec) was added to all tubes to label endothelial cells within the suspension. Cells were washed twice, and incubated 15 minutes on ice with CyChrome conjugated strepavidin (Pharminigen). Controls for all steps included matched species and isotype control antibodies (Pharminigen), as well as second step background staining were performed. Finally, cells were washed twice, fixed in 2% paraformaldehyde/PBS, and analyzed on a Coulter EPICS® Elite flow cytometer. Endothelial cells were identified and gated using a plot of FL1-FITC(Factor VIII)-vs-Side Scatter. This gate was used to generate plots of FL1-vs-FL3 (CyChrome) for the analysis of XNA binding.

Figure 12A:
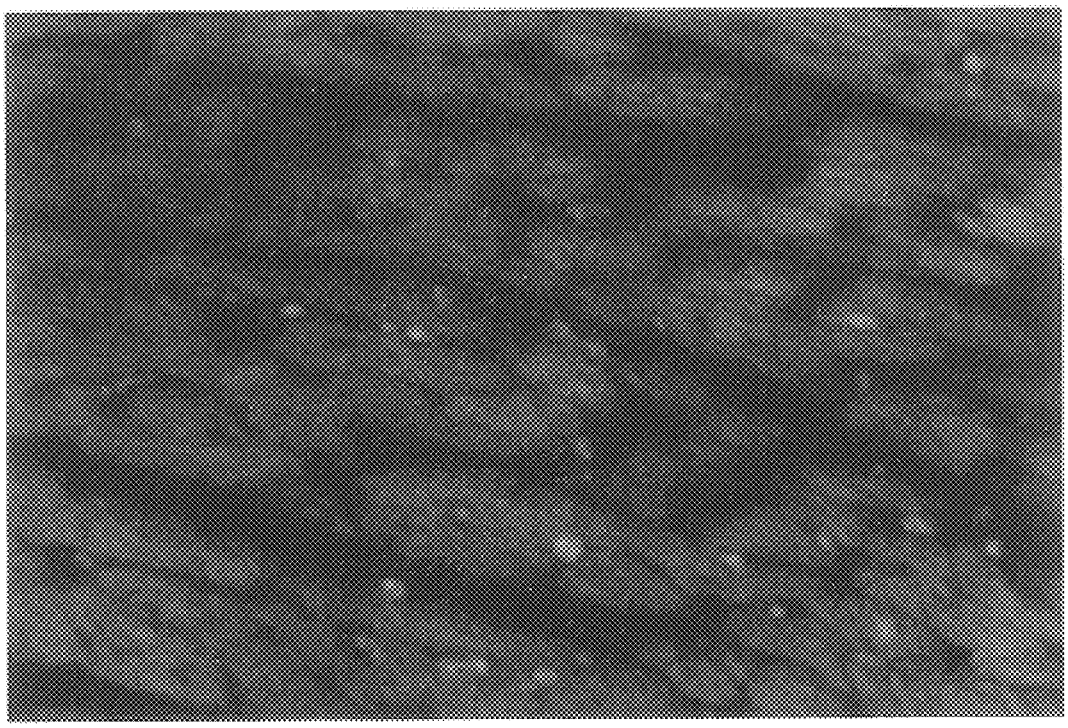
FIGS. 12A–D are photomicrographs of a microscopic fluorescence analysis of transgenic and non-transgenic murine heart sections stained with FITC conjugated lectins which evidence the reduction of the gal epitope by virtue of the expression of the $\alpha$(1,2)FT gene in accordance with the present invention, wherein A and C are non-transgenic heart and transgenic heart, respectively, stained with UEA-I, and wherein B and D are non-transgenic heart and transgenic heart, respectively, stained with GS-1-$B_4$.

As shown in FIG. 12A, the endothelial cells from the transgenic mouse exhibited a significant reduction in the level of XNA (IgM) binding as compared to ECs from the normal mouse. Incubation of XNAs with a disaccharide galactobiose, Galα(1,3)Gal, completely abolished the binding to ECs of normal as well as transgenic mice, indicating the specificity of XNAs for the gal epitope.

Next, the effect of reduced XNA binding on complement mediated lysis of ECs from transgenic mice was determined. To determine complement mediated lysis, aliquots of 4×10$^6$ cells from the digested suspension described above were pre-sensitized with 20 μg human XNA and simultaneously stained for Factor VIII, also as described above. The cells were washed and incubated for 45 minutes at 37° C. with increasing concentrations of rabbit serum (Sigma). All tubes contained a final concentration of 10 μg/ml propidium iodide to serve as a reporter for cell lysis. After incubation, the flow cytometric analysis as described above was performed to gate endothelial cells and to construct plots of FLI-FITC (Factor VIII)-vs-FL3-propidium iodide in order to assess the percentage of lysed cells staining positive in the FL3 channel. Controls consisted of aliquots containing no rabbit serum plus propidium iodide and those without PNA pre-sensitization in order to assess the ability of rabbit serum and Factor VIII antibody to lyse cells.

Figure 12B:
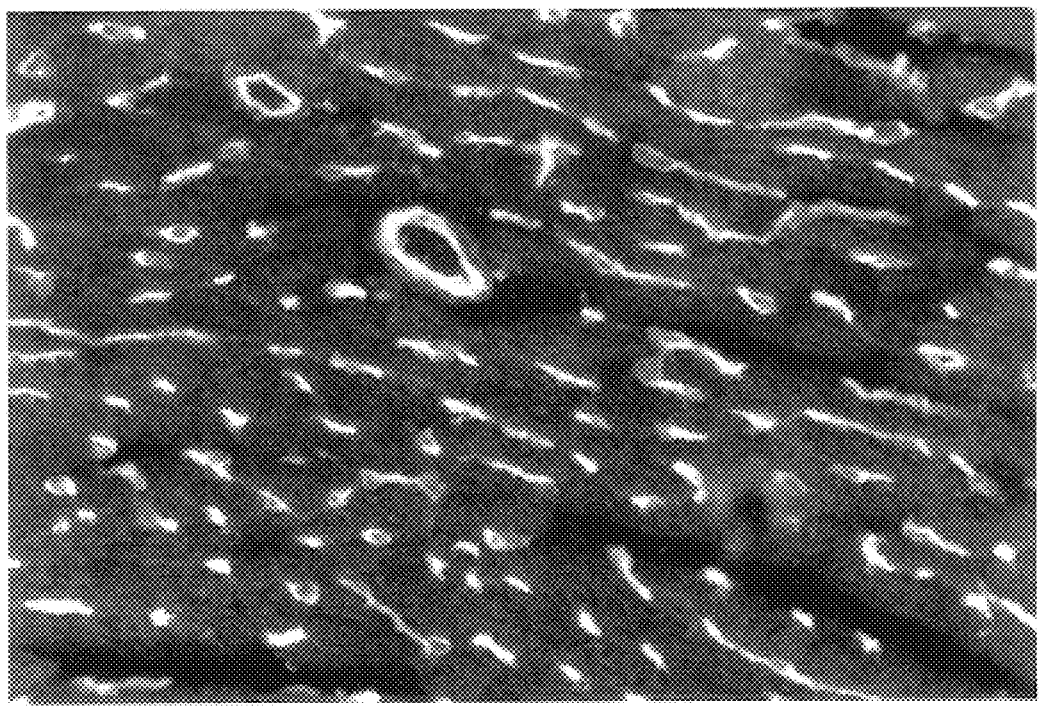
Figure 12C:
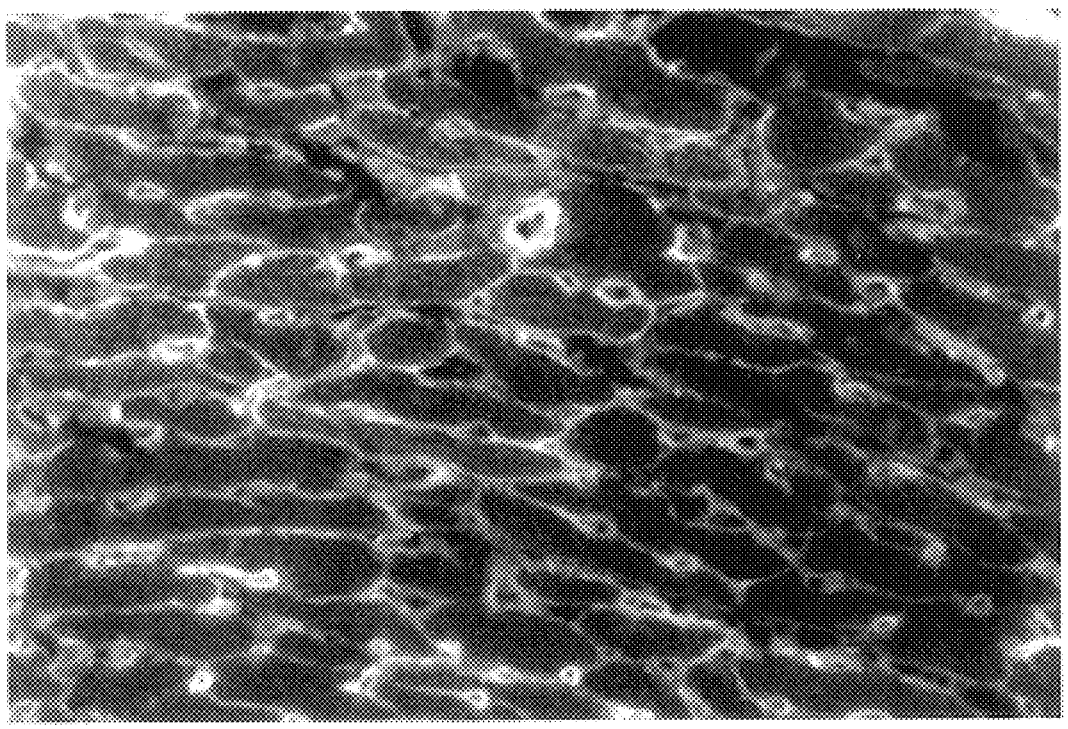
Figure 12D:
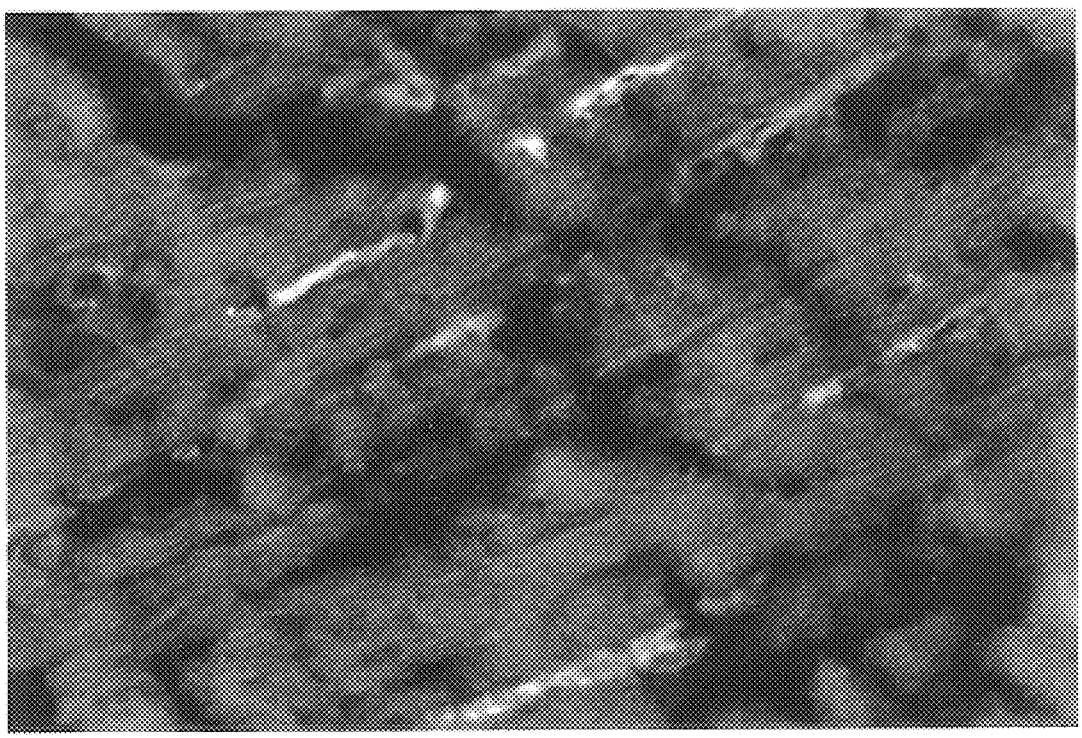

As shown in FIG. 12B, incubation of endothelial cells from control animals with XNAs which had rabbit serum added as a source of complement resulted in lysis of 14% of the cells. In contrast, less than 5% lysis of ECs of FT transgenic mice was observed, which is similar to the level of lysis of normal or transgenic ECs incubated with factor VIII antibody and rabbit serum without XNAs.

6.6 Generation of α(1,2)FT Transgenic Pigs

Based upon the results obtained with transgenic mice, transgenic pigs were generated by co-injecting the two α(1,2)FT constructs (#876 and #881) into the pronuclei of fertilized porcine eggs. A total of 656 injected eggs were transferred into pseudo pregnant females and 58 (33M, 25F) pigs were born. Five transgenic pigs (3M, 2F) were identified by PCR and confirmed by Southern analysis of tail DNA. One pig contained construct #876 (AcFT), one pig contained #881 (H2FT), and 3 pigs were positive for both.

6.7 Generation of α(2,6)ST Transgenic Pigs

Production of transgenic pigs was performed in much the manner previously described in this application. The expression of α(2,6)ST mRNA in transgenic pigs was determined by northern analysis of total RNA from muscle biopsies. Seven out of 18 pigs expressed the transgene at the transcriptional level.

6.8 Analysis of H Antigen Expression in α(1,2)FT Transgenic Pigs

Figure 13A:
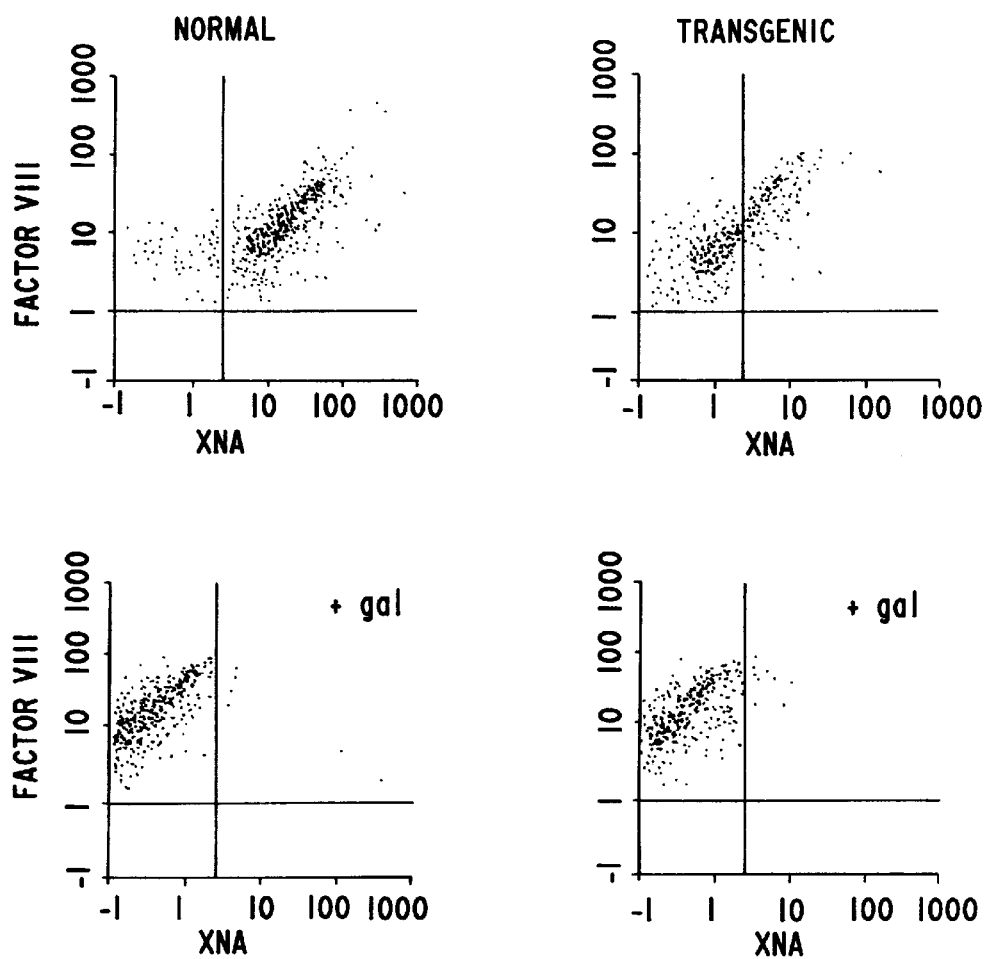
FIG. 13A is a flow cytometric analysis of the reduction in the binding of xenoreactive natural antibodies to endothelial cells of the $\alpha$(1,2)FT transgenic mice produced in accordance with the present invention when compared to non-transgenic mice.
Figure 13B:
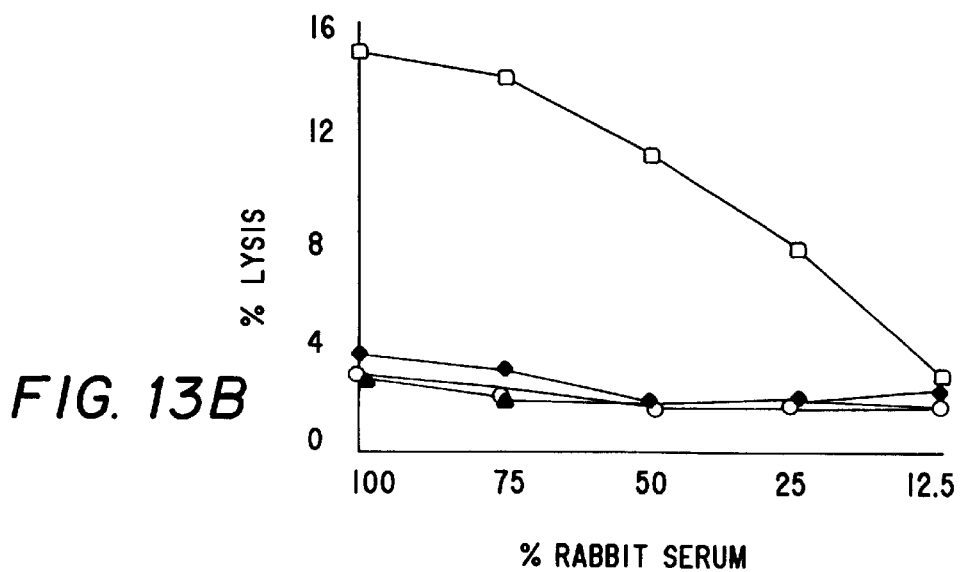
FIG. 13B is a graphic representation of the reduction in the level of complement-mediated lysis following incubation of rabbit serum with endothelial cells of the $\alpha$(1,2)FT transgenic mice produced in accordance with the present invention when compared to non-transgenic mice.
Figure 14A:
FIGS. 14A–D are photomicrographs of a microscopic fluorescence analysis of a tail section of $\alpha$(1,2)FT transgenic and non-transgenic pigs which evidence the reduction of the gal epitope by the expression of the $\alpha$(1,2)FT gene in accordance with the present invention, wherein A and C are non-transgenic porcine tail and transgenic porcine tail, respectively, stained with UEA-I, and wherein B and D are non-transgenic porcine tail and transgenic porcine tail, respectively, stained with GS-1-$B_4$.
Figure 14B:
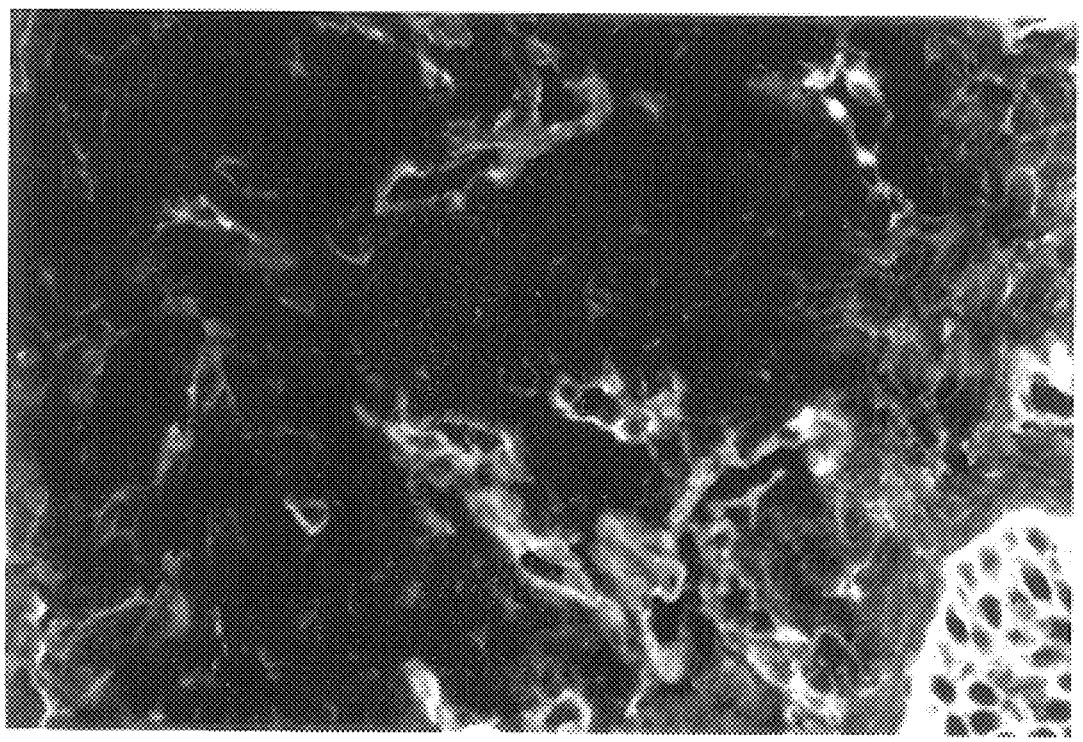
Figure 14C:
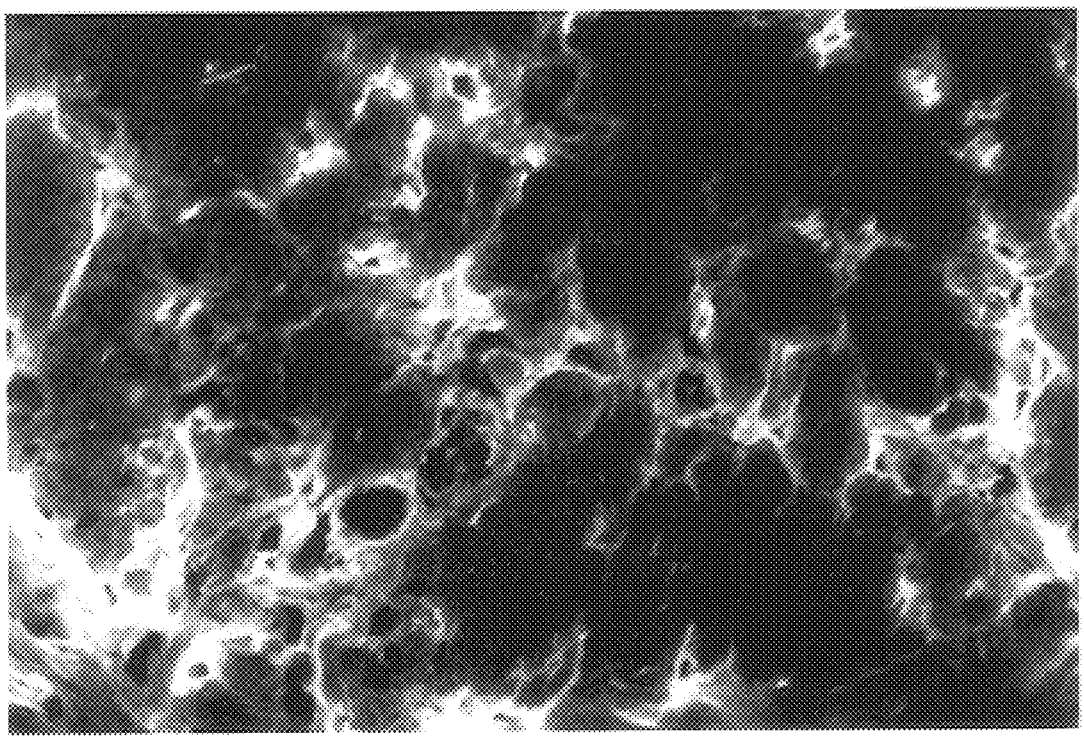
Figure 14D:
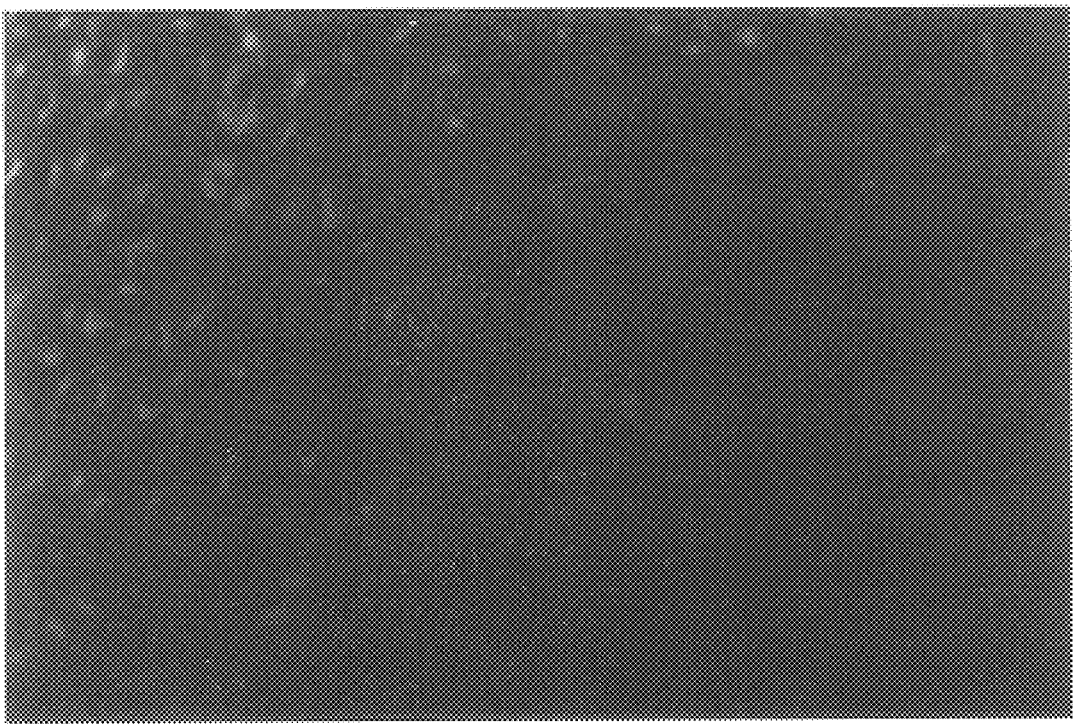

As a preliminary analysis of the effectiveness of the approach of the present invention in suppressing Galα(1,3) Gal synthesis in pigs, the tissues obtained from transgenic pigs containing construct #876 (AcFT) were analyzed. The β-actin promoter has been shown to give high levels of widespread expression in endothelial cells and muscle, as indicated in Hanasaki et al., J. Biol. Chem. 269:10637–10643 (1994). As in mice, high level expression of H antigen was detected by binding of the lectin UEA-I to tail sections of transgenic pigs compared to a non-transgenic littermate (see FIG. 13, C versus A). At the same time, expression of Galα(1,3)Gal, as indicated by staining with GS-1-B$_4$, was markedly decreased (see FIG. 12, B versus D). These data strongly suggest that the level of the xenogeneic gal epitope can be reduced by the expression of a competing glycosyltransferase.

While the present invention has been described with regard to the embodiments as set forth above, it will be immediately obvious to one of ordinary skill in the art that certain modifications and variations to the present invention as described above may be made without departing from the spirit and scope of the present invention. Accordingly, all such modifications will fall within the scope of the present invention, which is defined by the claims appended hereto.

Listing of Tables

| Table 1 | Distribution of CD59 in Human Tissues |
| --- | --- |
| Table 2 | Listing of Some Endothelial Genes/Promoters |
| Table 3 | Listing of Genes/Promoters Used to Produce Transgenic Mice |
| Table 4 | Densiometric Scan of CD59 Northern |
| Table 5 | Comparison of CD59 P1 Genomic Clones, CD59 Minigene #1 and CD59 |
| Table 6 | Microinjection of 2 or 3 Transgenes |
| Table 7 | Oligonucleotides Utilized to Screen a Human Genomic DNA Library |
| Table 8 | Transgenic Rate and Penetrance of CD59, CD46 (MCP) and DAF P1 Fragments in Mice |
| Table 9 | CD59 and CD46 Protein Expression in Transgenic Mouse Tissues |
| Table 10 | End Structure of P1 Genes |
| Table 11 | Assembly by Homologous Recombination |
| Table 12 | Sequence of Oligonucleotides Used to Produce a Polylinker for YAC4 |
| Table 13 | Sequence of PCR Primers for Amplification of CD59 Termini |

TABLE 1

Distribution of CD59 in human tissues

| TISSUE | CELLS | EXPRESSION |
| --- | --- | --- |
| Pancreas | Small duct epithelium | +++ |
|  | Myelinated nerve | ++ |
|  | Capillary endothelium | ++ |
|  | Islets of Langerhans | −/+ |
|  | Acinar cells | − |
| Kidney | Distal tubules | +++ |
|  | Thin loops of Henle | ++ |
|  | Small artery/vein endothelium | ++ |
|  | Glomerular endothelium | − |
|  | Pertibular capillary endothelium | − |
| Lung | Brinchial epithelium | −/+ |
|  | Alveolar cells | − |
|  | Small artery endothelium | −/+ |
|  | Alveolar capillary endothelium | − |
| Liver | Bile duct epithelium | +++ |
|  | Portal vein endothelium | ++ |
|  | Small artery endothelium | ++ |
|  | Kupfer cells | − |
|  | Hepatocytes | − |
|  | Myelinated nerve | +++ |
| Brain | Vascular endothelium | ++ |
|  | Astrocytes | − |
|  | Oligodendrocytes | − |
|  | Neurons | − |
| Breast | Duct epithelium | ++ |
|  | Acinar cells | − |
|  | Endotheliuin | ++ |
| Skin | Basal epidermins | ++ |
|  | Sweat duct epithelium | + |
|  | Endothelium | ++ |
| Adenoid | Basal epithelium | ++ |
|  | Endothelium | + |

Frozen tissue sections were incubated for 30 min. at room temperature with CD59 mAb YTH53.1. Bound antibodies were detected with rabbit anti-rat peroxidase conjugated antibodies.

Note: This Table reproduced from:

Walsh, L. A., Tone, M., Thiru, S. and Waidman, H. (1992) "The CD59 antigen—A multifunctional molecule". Tissue Antigens. 40:213–220.

TABLE 2

Listing of some endothelial genes/promoters

| GENE | TRANSGENIC MICE | SITE OF EXPRESSION |
| --- | --- | --- |
| 1 ELAM-1 ligand fucosyltransferase (ELFT) | no | platelets, mesenchymal and epithelial cells |
| 2 tyrosine kinase Flk-1 | no | endothelial cells and their embryonic precursors |
| 3 tyrosine kinase Flt-1 | no | endothelial cells and their embryonic precursors |
| 4 murine major histocompatability complex (H2K$^b$ class 1) | yes | vascular endothelium, fibroblasts, epithelial cells, and smooth muscle cells |
| 5 hemonectin (human serum constituent protein MSE55) | no | bone marrow stromal cells and endothelial cells |
| 6 human germ cell alkaline phosphatase (GCAP) | yes | intestine, endothelial cells and embryonic cells |
| 7 human thrombospondin | no | fibroblasts, endothelial cells, smooth muscle cells, pulmonary alveolar cells, glial cells and macrophages |
| 8 mouse thrombospondin (THBS1) | no | fibroblasts, endothelial cells, smooth muscle cells, pulmonary alveolar cells, glial cells and macrophages |
| 9 murine preproendothelin-1 | yes | vascular endothelium |
| 10 endothelial leukocyte adhesion molecule 1 (ELAM1) | no | endothelial cells |
| 11 rat insulin | yes | pancreatic islet endothelia |
| 12 tek | yes | embryonic endothelial cells |
| 13 tyrosine kinase Tie-1 and Tie-2 | no | developing vascular endothelial cells |
| 14 vascular cell adhesion molecule (VCAM-1) | no | endothelial cells |
| 15 vascular endothelial cell lineage-specific promoter | yes | vascular endothelial cells |
| 16 von willebrand factor | yes | subpopulation of endothelial cells in the yolk sac and adult brain |

References for Table 2:
1. Goelz, et al. (1990) "ELFT: A gene that directs the expression of an ELAM-1 ligand". Cell. 63: 1349–1356.
2. Shalaby, et al. (1995) "Failure of blood-island formation and vasculogenesis in Flk-1-deficient mice". Nature. 376: 62–66.
3. Fong, G. H., Rossant, J., Gertsenstein, M. and Breitman, M. L. (1995) "Role of the Flt-1 receptor tyrosine kinase in regulating the assembly of vascular endothelium". Nature. 376: 66–70.
4. Foder, et al. (1994) "Expression of a functional human complement inhibitor in a transgenic pig as a model for the prevention of xenogeneic hyperacute organ rejection". Proc Natl Acad Sci. 91: 11153–11157.
5. Bahou, W. F., Campbell, A. D. and Wicha, M. S. (1992) "cDNA cloning and molecular characterization of MSE55, a novel human serum constituent protein that displays bone marrow stromal/endothelial cell-specific expression". J. Biol Chem. 267: 13986–13992.
6. Narisawa, S., Smans, K. A., Avis, J., Hoylaerts, M. F. and Millan, J. L. (1993) "Transgenic mice expressing the tumor marker germ cell alkaline phosphatase: An in vivo tumor model for human cancer antigens". Proc Natl Acad Sci. 90: 5081–5085.

TABLE 2-continued

Listing of some endothelial genes/promoters

| GENE | TRANSGENIC MICE | SITE OF EXPRESSION |
|---|---|---|

7. Donoviel, et al. (1988) "Structural analysis and expression of the human thrombospondin gene promoter". J Biol Chem. 263 (35): 18590–18593.
Laherty, C. D., Gierman, T. M. and Dixit, V. M. (1989) "Characterization of the promoter region of the human thrombospondin gene". J Biol Chem. 264 (19): 11222–11227.
8. Bornstein, P., Dalia, A., Sreelekha, D., Framson, P. and Li, P. (1990) "Characterization of the mouse thrombospondin gene and evaluation of the role of the first intron in human gene expression". J Bio Chem. 265 (27): 16691–16698.
9. Harats, et al. (1995) "Targeting gene expression to the vascular wall in transgenic mice using the murine preproendothelin-1 promoter". J Clin Invest. 95: 1335–1344.
10. Goelz, et al. (1990) "ELFT: A gene that directs the expression of an ELAM-1 ligand". Cell. 63: 1349–1356.
11. Picarella, et al. (1993) "Transgenic tumor necrosis factor (TNF)-alpha production in pancreatic islets leads to insulitis, not diabetes. Distinct patterns of inflammation in TNF-alpha and TNF-beta transgenic mice". J Immunol. 150 (9): 4136–4150.
12. Dumont, et al. (1994) "Dominant-negative and targeted null mutations in the endothelial receptor tyrosine kinase, tek, reveal a critical role in vasculogenesis of the embryo". Genes Dev. 8: 1897–1909.
13. Sato, et al. (1995) "Distinct roles of the receptor tyrosine kinases Tie-1 and Tie-2 in blood vessel formation". Nature. 376: 70–74.
14. Osborn, et al. (1989) "Direct expression cloning of vascular cell adhesion molecule 1, a cytokine-induced endothelial protein that binds to lymphocytes". Cell. 59: 1203–1211.
15. Schlaeger, T. M., Quin, Y., Fujiwara, Y., Magram, J. and Sato, T. N. (1995) "Vascular endothelial cell lineage-specific promoter in transgenic mice". Development. 121: 1089–1098.
16. Aird, et al. (1995) "Human von willebrand factor gene sequences target expression to a subpopulation of endothelial cells in transgenic mice". Proc Natl Acad Sci. 92: 4567–4571. Collins, et al. (1987) "Molecular cloning of the human gene for von willebrand factor and identification of the transcription initiation site". Proc Natl Acad Sci. 84: 4393–4397.

TABLE 3

Listing of genes/promoters used to produce transgenic mice

| GENE/PROMOTER | TRANSGENIC MICE |
|---|---|
| 1 human CD 59/ murine major histocompatability complex (H2K$^b$ class 1) | yes |
| 2 human germ cell alkaline phosphatase (GCAP)/human germ cell alkaline phosphatase (GCAP) | yes |
| 3 luciferase gene/ murine preproendothelin-1 | yes |
| 4 murine TNF-alpha/ rat insulin promoter | yes |
| 5 LacZ reporter gene/ tek promoter | yes |
| 6 LacZ reporter gene/ vascular endothelial cell lineage-specific promoter | yes |
| 7 von willebrand factor/ von willebrand factor | yes |

References for Table 3:
1. Foder, et al. (1995) "Expression of a functional human complement inhibitor in a transgenic pig as a model for the prevention of xenogeneic hyperacute organ rejection". Proc Natl Acad Sci. 91: 11153–11157.
2. Narisawa, S., Smans, K. A., Avis, J., Hoylaerts, M. F. and Millan, J. L. (1993) Transgenic mice expressing the tumor marker germ cell alkaline phosphatase: An in vivo tumor model for human cancer antigens". Proc Natl Acad Sci. 90: 5081–5085.
3. Harats, et al. (1995) "Targeting gene expression to the vascular wall in transgenic mice using the murine preproendothelin-promoter". J Clin Invest. 95: 1335–1344.

TABLE 3-continued

Listing of genes/promoters used to produce transgenic mice

| GENE/PROMOTER | TRANSGENIC MICE |
|---|---|

4. Picarella, et al. (1993) "Transgenic tumor necrosis factor (TNF)-alpha production in pancreatic islets leads to insulitis, not diabetes. Distinct patterns of inflammation in TNF-alpha and TNF-beta transgenic mice". J Immunol. 150 (9): 4136–4150.
5. Dumont, et al. (1994) "Dominant-negative and targeted null mutations in the endothelial receptor tyrosine kinase, tek, reveal a critical role in vasculogenesis of the embryo". Genes Dev. 8: 1897–1909.
6. Schlaeger, T. M., Quin, Y., Fujiwara, Y., Magram, J. and Sato, T. N. (1995) "Vascular endothelial cell lineage-specific promoter in transgenic mice". Development. 121: 1089–1098.
7. Aird, et al. (1995) "Human von willebrand factor gene sequences target expression to a population of endothelial cells in transgenic mice". Proc Natl Acad Sci. 92: 4567–4571.

TABLE 4

Densiometric scan of CD59 Northern[1]

|  | KIDNEY | HEART | LIVER |
|---|---|---|---|
| CD59 MINIGENE 1 | 0.96 | 0.41 | 0.01 |
| CD59 MINIGENE 2 | 13.23 | 8.16 | 4.31 |
| CD59 P1 | 10.55 | 10.88 | 4.91 |
| HUMAN | 16.05 | 3.28 | 1.84 |

[1]Arbitrary values assigned to density of the predominant mRNA band of each sample as a means of comparison
[2]The CD59 Minigene 2 line depicted in the Northern expresses CD59 mRNA at an intermediate level as compared to all CD59 Minigene 2 mouse lines
[3]The CD59 P1 line depicted in the Northern expresses CD59 mRNA at the highest level as compared to all CD59 P1 mouse lines

TABLE 5

Comparison of CD59 P1 genomic clones, CD59 minigene #1 and CD59 minigene #2

|  | CD59 P1 | CD59 MINIGENE | CD59 MINIGENE | HUMAN |
|---|---|---|---|---|
| Transgenic Rate[1] | 8% | 23% | 30% | NA |
| Transmission[2] Rate | 89% | 86% | 68% | NA |
| Expression Rate[3] | 63% | 100% | 38% | NA |
| #CD59 molecules/ RBC[4] | 13,980/RBC | 20,435/RBC | 0 | 21,581/RBC |
| Protein on liver[5] | + | + | + (focal) | + |
| Protein on heart | + | +/++ | trace/+ | ++ |
| Protein on kidney | +/++ | +/++ | − | ++ |

[1]Percent of live births resulting in transgenic founders
[2]Percent of founders transmitting transgene to offspring
[3]Percent of founders giving rise to offspring which express the transgene at the RNA and at the protein level
[4]Direct quantitation of number of CD59 molecules per RBC on highest expressing line for each construct

TABLE 6

MICROINJECTION OF 2 OR 3 TRANSGENES SUMMARY OF CO-INTEGRATION AND SEGREGATION OF GENES

| | # Animals Born | Animals Transgenic For 1 or 2 Genes | Animals Transgenic For 2 Genes | Animals Transgenic For 3 Genes | Animals with Co-Integrated Genes |
|---|---|---|---|---|---|
| P1 Mice | 145 | 19 (13.1%) | 5 (3.4%) | 0 | 0 |
| MGT Mice[2] | ND | ND | ND | ND | ND |
| CRP cNDA Mice[3] | 81 | 11 (13.6%) | 4 (4.9%) | ND | 4/4 (100%) |
| P1 Pigs | 780 | 21 (2.7%) | 5 (0.64%) | 0 | ND |
| MG 1 Pigs[4] | 49 | 2 (4.1%) | 2 (4.1%) | ND | 2/2 (100%) |

[1]Co-integration is determined upon analysis of offspring
[2]CD59 Minigene 1 (MG 1) was not co-injected into mice.
[3]H-2K-DAF and β actin-CD59 constructs of 6.8 Kb and 2.2 Kb, respectively, were co-injected into mice.
[4]The CD59 Minigene 1 (MG 1) was used as an expression vector for insertion of MCP CDNA. Co-injection of the CD59 Minigene 1 and the CD59/MCPcDNA Minigene 1 was done in pigs.

TABLE 7

Oligonucleotides utilized to screen a human genomic DNA library constructed in the bacteriaphage P1

| Gene (bp*) | Oligonucleotide | Length of PCR Location of Amplified Region | Product | SEQ ID NO |
|---|---|---|---|---|
| CD59.212: | 5'-dAAT ACC AGG ATT TGA GCA CCA CC-'3 | 1602 bp 5' of transcriptional start | 288 | 27 |
| CD59.439c: | 5'-dACA CAC TTT GAG GGT CAG GGT G-'3 | | | 28 |
| CD59.202: | 5'-dGAG CAT TGC AAT TTC AAC GAC GTC-'3 | 183 bp of exon 4 plus 11 bp of | 196 | 29 |
| CD59.437c: | 5'-dTGG TGT TGA CTT AGG GAT GAA GGC-'3 | 3' untranslated region | | 30 |
| CD46*.99: | 5'-dATT GTT GTT GCG TCC CA-'3 | at transcriptional start site | 201 | 31 |
| CD46*.140c: | 5'-dCGG AGA AGG AGT ACA GC-'3 | | | 32 |
| CD46*.1205: | 5'-dTCC ACA ACC TGG TTT GCC AG-'3 | 6 bp 3' of translational stop | 135 | 33 |
| CD46*.1340c: | 5'-dAGG ATG CTA CCT ACA TTC AAG CCA C-'3 | | | 34 |
| CD55**.335: | 5'-dCAA ACA GCC TTA TAT CAC TC-'3 | short consensus repeat 2 in exon 3 | 112 | 35 |
| CD55**.446c: | 5'-AAG GCA AGT TAG TTT TGG TG-'3 | | | 36 |

*CD46 = MCP
**CD55 = DAF

TABLE 8

Transgenic rate and penetrance of CD59, CD46 (MCP) and DAF P1 fragments in mice[1]

| CONSTRUCT[2] | TRANSGENIC RATE (%) | TRANSMISSION percent (%) | EXPRESSING percent (%) | RNA LEVELS COMPARABLE TO HUMAN |
|---|---|---|---|---|
| CD59 (70Kb) | 9/115 (8%) | 8/9 (89%) | 5/8 (63%) | 2/5 (40%) |
| CD59 (50Kb) | 3/40 (7.5%) | 3/3 (100%) | 2/3 (67%) | 0/3 (0%) |
| CD46* (60Kb) | 13/44 (29%) | 9/13 (70%) | 7/9 (78%) | 4/7 (57%) |

TABLE 8-continued

Transgenic rate and penetrance of CD59, CD46
(MCP) and DAF P1 fragments in mice[1]

| CONSTRUCT[2] | TRANSGENIC RATE (%) | TRANSMISSION percent (%) | EXPRESSING percent (%) | RNA LEVELS COMPARABLE TO HUMAN |
|---|---|---|---|---|
| CD48* (80Kb) | 13/85 (15%) | 8/13 (61%) | 7/8 (86%) | N/D[3] |
| DAF (90Kb) | 6/19 (31%) | 5/6 (83%) | 4/5 (80%) | N/D[3] |
| DAF (70Kb) | 3/18 (17%)[4] | N/D[3] | 3/3 (100%) | N/D[3] |

CD46 is the same as MCP.
[1]Penetrance: proportion of individuals possessing a specific genotype (i.e. P1 transgene) who manifest the genotype at the phenotypic level (i.e., expression of C'regulatory proteins).
[2]All gene copy numbers ranged between 1 and 5 copies.
[3]N/D: not done
[4]Data compiled by analyzing founders not G₁s.

TABLE 9

CD59 and CD46 protein expression in transgenic mouse tissues[1]

| TISSUE | CD59 (line 5-2) | CD46 (line 27-3) |
|---|---|---|
| liver | +1 endothelial cells | +2 endothelial cells |
| heart | +1 endothelial cells and myocytes | +1 endothelial cells |
| kidney | +1 to +2 endothelial cells; + tubules | +1 endothelial cells; tubules |
| lung | +1 all positive cells | +1 endothelial cells |
| spleen | trace + splenocytes +1 blood vessels; | +1 endothelial cells |
| muscle | +1 muscle cells | +1 endothelial cells |
| pancreas | +1 islets | +2 islets |
| brain | trace to + endothelial cells; + capillaries | +1 endothelial cells |

[1]. Tissues from nontransgenic littermates were used as controls.
[2]. Readings were assessed on a semiquantitative scale of trace to +4.

TABLE 10

End structure of P1 genes and fragments

| P1 Transgene | Size (kb) | 5' terminus | 3' terminus | *5' fragment | *3' fragment |
|---|---|---|---|---|---|
| CD46 | 60 | Mlu1 | Mlu1 | 1.5kb (sc) Mlu-Sal Sac1-Sal | 1.3kb (sc) Nco1-Mlu EcoR1-EcoR1 |
| CD55 | 70 | Not1 | Sfi1 | 2.2kb (pr; sc) Not1-Sac1 | 0.8kb (pr; sc) Xba1-Sal1 |
| CD59 | 70 | Sfi1 | Sfi1 | 1.4kb (pr; pcr) Not1-BamH1 | 1.2kb (pr; pcr) SnaB1-Hinc2 Kpn1-Sal1 |

*These columns list the size and flanking restriction sites associated with the terminal subclones derived from the extreme ends of each P1 gene. For CD55 and CD59 these fragments were initially identified by plasmid rescue (pr) from the P1 vector. Subsequently, smaller fragments were either subcloned (sc) or amplified (pcr) using PCR. The termini of the CD46 gene were directly subloned from the 60kb Mlu1 insert. Gene orientations are standardized to the 5' to 3' direction of transcription. Restriction enzymes that define the subclone fragments are similarly listed in 5' to 3' sequence. For some fragments more then one pair of restriction enzymes are listed. The additional enzyme sites were derived from polylinker restriction sites present in the cloning vectors.

TABLE 11

Assembly by Homologous recombination

| YAC Chromosome Structure | Clone Frequency | Clone Size |
|---|---|---|
| TRP-CD59-URA | 18/24 | 100 kb |
| TRP-CDS9-5'MCP-LYS | 6/6 | 102 kb |
| TRP-CD59-MCP-URA | 12/24 | 160 kb |

TABLE 12

Sequence of Oligonucleotides used to produce a polylinker for YAC4

```
Oligonucleotide  Sequence 4.1A             5' ATG CGA ATT CGG CGC GCC ACG CGT GCG GCC (SEQ ID NO:37)

GCA AGG CCA ATT AGG CCT ACG TAG GCG CGC

CGA ATT CTC G 3'
```

TABLE 12-continued

Sequence of Oligonucleotides used to produce a polylinker for YAC4

Oligonucleotide Sequence 4.1B   5' CGA GAA TTC GGC GCG CCT ACG TAG GCC TAA (SEQ ID NO:38)

TTG GCC TTG CGG CCG CAC GCG TGG CGC

GCC GAA TTC GCA T 3'

TABLE 13

Sequence of PCR Primers for Amplification of CD59 Termini

Primer Sequence

5CH-1  5' TAT AGC GGC CGC AAG GCC ATT TAG GCC ATG TGA (SEQ ID NO.39)

AAA AGG AAT GAA ATT GAG ATA TTG

5CH-2  5' AGC ATG GAT CCG GCC CTG TAA GTA CAG TGG      (SEQ ID NO:40)

ED-1   5' ATC ATA CGT ATT GGG CTT TTC TTC CAC CTG      (SEQ ID NO:41)

ED-2   5' ATT TGT CGA CCC ACT TGC TTC ATC TTA ATC     (SEQ ID NO:42)

What is claimed is:

1. A method of preparing organs, tissues, or cells for xenotransplantation into human patients with reduced rejection comprising the steps of:
   (a) providing a transgenci pig which is a source of transplant material which is anatomically and physiologically compatible with a human patient, said material selected from the group consisting of organs, tissues, or cells, said pig expressing
      (i) at least one transgenically encoded enzyme, functional in said pig, and in particular in said organs, tissues, or cells, that masks or reduces the level of a zenoreactive antigen of said transplant material, said at least one enzyme being a fucosyltransferase, and
      (ii) at least one transgenically encoded complement inhibitor functional in humans; and
   (b) isolating said transplant material from said transgenic pig, said material having been modified by said enzyme, wherein said modification results in a masking or a reduction in the level of a zenoreactive antigen thereof, said material further being associated with said complement inhibitor.

2. The method of claim 1 in which the enzyme is $\alpha(1,2)$fucosyltransferase.

3. The method according to claim 1 wherein the transgenic pig expresses one or more complement inhibitors selected from the group consisting of CD59, DAF, MCP, and combinations thereof.

4. The method according to claim 3 wherein the transgenic pig expresses CD59, DAF and MCP.

5. The method according to claim 3 wherein the transgenic pig expresses CD59 and DAF.

6. The method according to claim 1 wherein the transgenic pig expresses CD59 and MCP.

7. A method according to claim 3 wherein the transgenic pig expresses DAF and MCP.

8. The method according to claim 1 wherein the transgenic pig is produced by introducing into said animal, a nucleic acid coding for a fucosyltransferase and a nucleic acid coding for said at least one complement inhibiting protein.

9. The method according to claim 8 wherein the nucleic acid is introduced in the form of a minigene.

10. The method according to claim 8 wherein the nucleic acid is introduced in the form of a minigene cassette.

11. The method according to claim 8 wherein the nucleic acid is introduced in the form of a yeast artificial chromosome (YAC).

12. The method according to claim 8 wherein the nucleic acid is introduced in the form of bacteriophage P1 clones.

13. The method according to claim 1 wherein the transgenic pig is produced by co-injecting into said pig a nucleic acid coding for a fucosyltransferase along with a nucleic acid coding for at least one complement inhibitor.

14. The method according to claim 13 wherein the co-injection is carried out by co-injecting said nucleic acid coding for said fucosyltransferase along with said nucleic acid coding for said at least one complement inhibitor into a pronucleus of a fertilized oozyte of said pig, said transferring the oocyte to a pseudo pregnant female to be carried to term so as to produce said transgenic pig expressing said enzyme that masks or reduces the level of the xenoreactive antigens and said complement inhibitor.

15. The method according to claim 1 wherein the transgenic pig is produced using a nucleic acid cloned into an expression vector.

16. The method according to claim 15 wherein the expression vector is a plasmid.

17. The method according to claim 15 wherein the expression vector comprises eukaryotic expression vector pRex 10.

18. The method according to claim 15 wherein the expression vector further comprises a promoter.

19. The method according to claim 18 wherein the promoter comprises chicken $\beta$-actin promoter.

20. The method according to claim 18 wherein the promoter comprises an $H2k^b$ promoter.

21. The method according to claim 15 wherein the expression vector further comprises an enhancer.

22. The method according to claim 1 wherein said nucleic acid coding for said enzyme has been cloned by RT-PCR.

23. The method according to claim 1 wherein said nucleic acid coding for said enzyme has been cloned using total RNA from the A431 cell line.

24. A nonhuman transgenic animal useful for providing organs, tissues, or cells for use in xenotransplantation, which is able to stably express (a) at least one transgenically encoded enzyme functional in said animal which masks or reduces the level of a zenoreactive antigen, said enzyme being a fucosyltransferase, and (b) at least one transgenically encoded complement inhibitor functional in humans, said animal being a source of transplant material, in the form of an organ, tissue, or cell, which is anatomically and physiologically compatible with a human recipient, wherein the likelihood or severity of hyperacute rejection of said material, as a result of transplantation of said material into a human patient, is reduced relative to the likelihood or severity of such rejection of said material in the absence of said expresssion, and wherein said animal is a pig.

25. The transgenic animal according to claim 24 wherein the expressed enzyme competes the $\alpha(1,3)$ galactosyltransferase enzyme, thereby reducing the level of the zenoreactive antigens.

26. The transgenic animal according to claim 24 wherein the enzyme able to mask or reduce the level of xenoreactive antigens and the complement inhibitor are expressed in endothelial cells.

27. The transgenic animal according to claim 24 wherein the transgenic animal expresses one or more complement inhibitors selected from the group consisting of CD59, DAF, MCP, and combinations thereof.

28. the transgenic animal according to claim 26 wherein the transgenic animal expresses CD59, DAF and MCP.

29. The animal of claim 24 in which the enzyme is α(1,2)fucosyltransferase.

30. A method of xenotransplanting organs, tissues, or cells into human subjects which comprises providing compatible transplant material prepared for xenotransplantation by the method of claim 1, and then
transplanting said transplant material from said transgenic animal into a human patient.

31. The method of claim 30 in which the enzyme competes with the α(1,3)galactoxyltransferase enzyme, thereby reducing the level of the zenoreactive antigens.

32. The method of claim 30 wherein said enzyme is expressed by and functional in said transplant material, continuing to mask or reduce the level of zenoreactive antigen, even after transplantation of said transplant material into a human recipient.

33. The method of claim 30 in which the enzyme is α(1,2)fucosyltransferase.

34. A method of producing nonhuman transgenic animals useful in xenotransplantation with reduced rejection comprising introducing into said animal a nucleic acid that expresses at least one enzyme functional in said animal which masks or reduces the level of a zenoreactive antigen, said enzyme being a fucosyltransferase, and nucleic acid that expresses at least one complement inhibitor functional in humans, said animal being a source of an organ, tissue, or cell for xenotransplantation into humans, and anatomically and physiologically compatible with a human patient said animal being a pig.

35. The method according to claim 34 wherein the transgenic animals are produced by co-injecting a nucleic acid coding for said at least one enzyme which masks or reduces the level of the xenoreactive antigens and said at least one complement inhibitor into the pronuclei of a fertilized oocyte of the animal, and transferring the oocyte to a pseudo pregnant female to be carried to term so as to produce said transgenic animal expressing both said enzyme that masks or reduces the level of the xenoreactive antigens and said complement inhibiting protein.

36. The method according to claim 34 wherein the transgenic animals are produced by separately producing transgenic animals expressing a nucleic acid coding for said at least one enzyme which masks or reduces the level of the xenoreactive antigens and transgenic animals expressing a nucleic acid coding for said complement inhibitor, and breeding the two transgenic animals so that transgenic offspring of the bred animals will be produced which express said at least one enzyme which masks or reduces the level of the xenoreactive antigens and said at least one complement inhibitor.

37. The method according to claim 34 wherein the transgenic animals are produced by preparing a single YAC construct containing a nucleic acid coding for said at least one enzyme which masks or reduces the level of the xenoreactive antigens and said at least one complement inhibitor protein, and introducing the YAC construct into said animal so that the animal and its offspring will express said least one enzyme which masks or reduces the level of the xenoreactive antigens and said at least one complement inhibitor protein.

38. The method according to claim 34 wherein the transgenic animals are produced by preparing a single minigene containing a nucleic acid coding for said at least one enzyme which masks or reduces the level of the xenoreactive antigens and at least one complement inhibitor protein, and introducing the minigene into said animal so that the animal and its offspring will express said at least one enzyme which masks or reduces the level of the xenoreactive antigens and said at least one complement inhibitor protein.

39. The method according to claim 34 wherein the transgenic animals are produced by preparing one or more minigenes containing a nucleic acid coding for said at least one enzyme which masks or reduces the level of the xenoreactive antigens and one or more minigenes containing a nucleic acid coding for said at least one complement inhibitor protein, and introducing both types of minigenes into said animal so that the animal and its offspring will express said at least one enzyme which masks or reduces the level of the xenoreactive antigens and said at least one complement inhibitor protein.

40. A method according to claim 34 wherein the transgenic animals are produced by preparing a P1 clone containing a nucleic acid coding for said at least one enzyme which masks or reduces the level of the xenoreactive antigens and said at least one complement inhibitor protein, and introducing the P1 clone into said animal so that the animal and its offspring will express at least one enzyme which masks or reduces the level of the xenoreactive antigens and said at least one complement inhibitor protein.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

TTTGGATCCT CGGCCATGTG GCTCCGGAGC CATCG                                   35

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AAAGTCGACT CAAGGCTTAG CCAATC                                             26

(2) INFORMATION FOR SEQ ID NO:3:

(i) SEQUENCE CHARACTERISTICS:
        (A) LENGTH: 3791 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:3:

```
AAGCTTGGCC CACAAGGAGT GGCAATGTTA GGAGTGTGAC TGTGTTAGAG GAAGTGTGTC      60
ACTTTGAGGT TGGCCTTTGA GGTCTCCTAT GCTCATGAGC TGCCCAGTGT GGAATGAAAG     120
CCTCTTCCTG GCTGCATTTG GATCAAGATG TAGAAGTCTC CCCTTCTCCA GCACCATGCC     180
TACCTGCACA CTGGTACGCC TGCCTTCCGT CATGATGGAC TAAATTCCTG AAACTGTAAG     240
CCAGACCCTA TTAAATGTCT CCCTTTAGAA GGAATGCCTT GGTCATGGTG TTTCTTCACA     300
GCAACAAAAC CAAAACTAAC ACACCCAGCA CTTAGGATGC AAAGGCAGAT GTATCTCTGT     360
GAGTTCAAGG GCAGCCTGAT CTACATAATG AATTACAGAA TAGCCAGGGC TGTGCAGATA     420
GACCTTGTCT AAACAAGCAA ACAAACAAAA CCCATAGTAA AATAAGAAGA AAAGTAATGG     480
AGACAGATCC TTTGTGTAGC TGCCTAACCC CAACAGCATC CCTAGGTTGA TCAGGAAGAA     540
ACCTAAGAGC ATCAAGTCCC CATGGAAAAT GCTCACAACA TCTAATAAGA GGGGTTCAGG     600
GAGACAGGGT CTGCTGAATC CTGGTGAGGC TGGGGGGCTG CTGTGGGGAT CTGCATGGGG     660
AGGTGACTGG AGTTCACACC TGTGGTCGCA CGCATTCATT GCTCTGTGTG ATGAGTGACT     720
CTCTTCAGGA GTCCCCACCC ATCTATGCTC TTCTTTCCAC TTCACTTCTG TGACTGATTT     780
GAAAAGATCC ACAGAATCAT GAAATGGGTA AATTTAATCT TTCCCCACAC TACTGATCAG     840
GGATGAAACC TCACATCACA GTGTGTGCTC TCTGGCATGA GAATCATCTT TCTCCCAGTG     900
TCCACACTGC ACAGGCCTGA GGAACTCTGG GGCCAACTCA ATTATCAGAA CCCGTGTCCC     960
ACACAGCTGT GACGTTCGTG TCCCTCATCA GCTCAAAAGT GTGAGTGAAG GTCAGGGAGG    1020
GAGGGAGAGG GTCAGAGATT ACATAACTTC TACCACACTA GCATCCTTAT TCTGTGTTAT    1080
AGTTGGTGAC AGCTCCTCTC CTACTGTGAT TGAGTCACTA AAGCAACTGC ACCATGGAAG    1140
TGCAGACACA GAGAAGTCCA GTGGAGACAG GGATCAGTGC CCTGCTGTCT GTGGTCTGCA    1200
CGGGGTCTCT CTTCAGTGGA CAAGGGGTC TCCTGTGCTG AGACAATGTC CCAGATCCAC    1260
AGAGACAAAC TCAGGACTCA GAATGAAGAT CCTTGTTTCA AATACACACA CACACACATA    1320
CACACACACA CACACACACA CACACACACA CACACACACC TGCAGCCACA GACTTTTCAT    1380
CTAGGAATTA ACACAAGGAA TCTGTGTCTC AGCACAGGGC TGAGGAGACA GATCCTGAGG    1440
GGAGAGGCAA AGTCTACACT TAACAGATGA GAGTCCTGCA CTCAGGCTTG GCAGTGTGAG    1500
CCGCCCATTG CAGGTGAACA GAGCCTGGTC TCTGTGGGGT CCCTGTGGGG CTTGCAGCCC    1560
AGCGCCTTGA CTTTAAGGAA AAGCCTCTCT CTCCACTGCA TCCCTAAGCG CTTGTGTCGC    1620
CATTGTATTC CCGGAAGAGG CTTTTCTTCT AGAAGACTCC AGGGTCTGAC TTCTGAAGAG    1680
AAGAAGAAAG AGGAAGAGTG GAAGAGAGGA CACAGAGAGT CTGGCCTGCG GGTCTCTCCT    1740
GGTGTTTTGA GAGTTTCTGG ATCAGAACTC GGAGACGACA GCACAGGGTT CAGGCAAAGT    1800
CTTAGTCGCC AGGCAGTGAG GTCAGGGGTG GGGAAGCCCA GGGCTGGGGA TTCCCCATCT    1860
CCACAGTTTC ACTTCTGCAC CTAACCTGGG TCAGGTCCTT CTGTCCGGAC ACTGTTGACG    1920
CGCAGTCAGC TCTTACCCCC ATTGGGTGGC GCGATCACCA AGAACCAATC AGTGTCGCCG    1980
CGGACGCTGG ATATAAAGTC CACGCAGCCC GCAGAACTCA GAAGTCTCGC CGGAATTCCT    2040
GCAGCCCGAT CCTCGGCCAT GTGGCTCCGG AGCCATCGTC AGCTCTGCCT GGCCTTCCTG    2100
CTAGTCTGTG TCCTCTCTGT AATCTTCTTC CTCCATATCC ATCAAGACAG CTTTCCACAT    2160
GGCCTAGGCC TGTCGATCCT GTGTCCAGAC CGCCGCCTGG TGACACCCCC AGTGGCCATC    2220
TTCTGCCTGC CGGGTACTGC GATGGGCCCC AACGCCTCCT CTTCCTGTCC CCAGCACCCT    2280
```

```
GCTTCCCTCT CCGGCACCTG GACTGTCTAC CCCAATGGCC GGTTTGGTAA TCAGATGGGA    2340

CAGTATGCCA CGCTGCTGGC TCTGGCCCAG CTCAACGGCC GCCGGGCCTT TATCCTGCCT    2400

GCCATGCATG CCGCCCTGGC CCCGGTATTC CGCATCACCC TGCCCGTGCT GGCCCCAGAA    2460

GTGGACAGCC GCACGCCGTG GCGGGAGCTG CAGCTTCACG ACTGGATGTC GGAGGAGTAC    2520

GCGGACTTGA GAGATCCTTT CCTGAAGCTC TCTGGCTTCC CCTGCTCTTG GACTTTCTTC    2580

CACCATCTCC GGGAACAGAT CCGCAGAGAG TTCACCCTGC ACGACCACCT TCGGGAAGAG    2640

GCGCAGAGTG TGCTGGGTCA GCTCCGCCTG GGCCGCACAG GGGACCGCCC GCGCACCTTT    2700

GTCGGCGTCC ACGTGCGCCG TGGGGACTAT CTGCAGGTTA TGCCTCAGCG CTGGAAGGGT    2760

GTGGTGGGCG ACAGCGCCTA CCTCCGGCAG GCCATGGACT GGTTCCGGGC ACGGCACGAA    2820

GCCCCCGTTT TCGTGGTCAC CAGCAACGGC ATGGAGTGGT GTAAAGAAAA CATCGACACC    2880

TCCCAGGGCG ATGTGACGTT TGCTGGCGAT GGACAGGAGG CTACACCGTG GAAAGACTTT    2940

GCCCTGCTCA CACAGTGCAA CCACACCATT ATGACCATTG GCACCTTCGG CTTCTGGGCT    3000

GCCTACCTGG CTGGCGGAGA CACTGTCTAC CTGGCCAACT TCACCCTGCC AGACTCTGAG    3060

TTCCTGAAGA TCTTTAAGCC GGAGGCGGCC TTCCTGCCCG AGTGGGTGGG CATTAATGCA    3120

GACTTGTCTC CACTCTGGAC ATTGGCTAAG CCTTGAGTCG ACGTGCAGGC ATGCAAGCTT    3180

CGGGTGGACC CGGTCAACTT CAAGGTGAGC GGCGGGCCGG GAGCGATCTG GGTCGAGGGG    3240

CGAGATGGCG CCTTCCTCTC AGGGCAGAGG ATCACGCGGG TTGCGGGAGG TGTAGCGCAG    3300

GCGGCGGCGC GGCTTGGGCC GCACTGACCC TCTTCTCTGC ACAGCTCCTA AGCCACTGCC    3360

TGCTGGTGAC CCTGGCCGCC CACCTCCCCG CCGAGTTCAC CCCTGCGGTG CACGCTTCCC    3420

TGGACAAGTT CCTGGCTTCT GTGAGCACCG TGCTGACCTC CAAATACCGT TAAGCTGGAG    3480

CCTCGGTAGC CGTTCCTCCT GCCCGCTGGG CCTCCCAACG GGCCCTCCTC CCCTCCTTGC    3540

ACCGGCCCTT CCTGGTCTTT GAATAAAGTC TGAGTGGGCG GCAGCCTGTG TGTGCCTGGG    3600

TTCTCTCTGT CCCGGAATGT GCCAACAATG GAGGTGTTTA CCTGTCTCAG ACCAAGGACC    3660

TCTCTGCAGC TGCATGGGGC TGGGGAGGGA GAACTGCAGG GAGTATGGGA GGGGAAGCTG    3720

AGGTGGGCCT GCTCAAGAGA AGGTGCTGAA CCATCCCCTG TCCTGAGAGG TGCCAGCCTG    3780

CAGGCAGTGG C                                                        3791
```

(2) INFORMATION FOR SEQ ID NO:4:

(i) SEQUENCE CHARACTERISTICS:
        (A) LENGTH: 2268 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CCGGGAGGTG ACTTCAAGGG GACCGCAGGA CCACCTCGGG GGTGGGGGA GGGCTGCACA      60

CGCGGACCCC GCTCCCCCTC CCCAACAAAG CACTGTGGAA TCAAAAAGGG GGGAGGGGGG    120

ATGGAGGGGC GCGTCACACC CCCGCCCCAC ACCCTCACCT CGAGGTGAGC CCCACGTTCT    180

GCTTCACTCT CCCCATCTCC CCCCCCTCCC CACCCCCAAT TTTGTATTTA TTTATTTTTT    240

AATTATTTTG TGCAGCGATG GGGGCGGGGG GGGGGGGGC GCGCGCCAGG CGGGGCGGGG    300

CGGGGCGAGG GGCGGGGCGG GGCGAGGCGG AGAGGTGCGG CGGCAGCCAA TCAGAGCGGC    360

GCGCTCCGAA AGTTTCCTTT TATGGCGAGG CGGCGGCGGC GGCGGCCCTA TAAAAAGCGA    420
```

```
AGCGCGCGGC GGGCGGGAGT CGCTGCGTTG CCTTCGCCCC GTGCCCCGCT CCGCGCCGCC        480

TCGCGCCGCC CGCGCCCGGA CGGATCCCTC GGCCATGTGG CTCCGGAGCC ATCGTCAGCT        540

CTGCCTGGCC TTCCTGCTAG TCTGTGTCCT CTCTGTAATC TTCTTCCTCC ATATCCATCA        600

AGACAGCTTT CCACATGGCC TAGGCCTGTC GATCCTGTGT CCAGACCGCC GCCTGGTGAC        660

ACCCCCAGTG GCCATCTTCT GCCTGCCGGG TACTGCGATG GGCCCCAACG CCTCCTCTTC        720

CTGTCCCCAG CACCCTGCTT CCCTCTCCGG CACCTGGACT GTCTACCCCA ATGGCCGGTT        780

TGGTAATCAG ATGGGACAGT ATGCCACGCT GCTGGCTCTG GCCCAGCTCA ACGGCCGCCG        840

GGCCTTTATC CTGCCTGCCA TGCATGCCGC CCTGGCCCCG GTATTCCGCA TCACCCTGCC        900

CGTGCTGGCC CCAGAAGTGG ACAGCCGCAC GCCGTGGCGG GAGCTGCAGC TTCACGACTG        960

GATGTCGGAG GAGTACGCGG ACTTGAGAGA TCCTTTCCTG AAGCTCTCTG GCTTCCCCTG       1020

CTCTTGGACT TTCTTCCACC ATCTCCGGGA ACAGATCCGC AGAGAGTTCA CCCTGCACGA       1080

CCACCTTCGG GAAGAGGCGC AGAGTGTGCT GGGTCAGCTC CGCCTGGGCC GCACAGGGGA       1140

CCGCCCGCGC ACCTTTGTCG GCGTCCACGT GCGCCGTGGG GACTATCTGC AGGTTATGCC       1200

TCAGCGCTGG AAGGGTGTGG TGGGCGACAG CGCCTACCTC CGGCAGGCCA TGGACTGGTT       1260

CCGGGCACGG CACGAAGCCC CCGTTTTCGT GGTCACCAGC AACGGCATGG AGTGGTGTAA       1320

AGAAAACATC GACACCTCCC AGGGCGATGT GACGTTTGCT GGCGATGGAC AGGAGGCTAC       1380

ACCGTGGAAA GACTTTGCCC TGCTCACACA GTGCAACCAC ACCATTATGA CCATTGGCAC       1440

CTTCGGCTTC TGGGCTGCCT ACCTGGCTGG CGGAGACACT GTCTACCTGG CCAACTTCAC       1500

CCTGCCAGAC TCTGAGTTCC TGAAGATCTT TAAGCCGGAG GCGGCCTTCC TGCCCGAGTG       1560

GGTGGGCATT AATGCAGACT TGTCTCCACT CTGGACATTG GCTAAGCCTT GAGTCGACTT       1620

TAATCCATAT GACTAGTAGA TCCTCTAGAG TCAGCTTCGG GTGGACCCGG TCAACTTCAA       1680

GGTGAGCGGC GGGCCGGGAG CGATCTGGGT CGAGGGGCGA GATGGCGCCT TCCTCTCAGG       1740

GCAGAGGATC ACGCGGGTTG CGGGAGGTGT AGCGCAGGCG GCGGCGCGGC TTGGGCCGCA       1800

CTGACCCTCT TCTCTGCACA GCTCCTAAGC CACTGCCTGC TGGTGACCCT GGCCGCCCAC       1860

CTCCCCGCCG AGTTCACCCC TGCGGTGCAC GCTTCCCTGG ACAAGTTCCT GGCTTCTGTG       1920

AGCACCGTGC TGACCTCCAA ATACCGTTAA GCTGGAGCCT CGGTAGCCGT TCCTCCTGCC       1980

CGCTGGGCCT CCCAACGGGC CCTCCTCCCC TCCTTGCACC GGCCCTTCCT GGTCTTTGAA       2040

TAAAGTCTGA GTGGGCGGCA GCCTGTGTGT GCCTGGGTTC TCTCTGTCCC GGAATGTGCC       2100

AACAATGGAG GTGTTTACCT GTCTCAGACC AAGGACCTCT CTGCAGCTGC ATGGGGCTGG       2160

GGAGGGAGAA CTGCAGGGAG TATGGGAGGG GAAGCTGAGG TGGGCCTGCT CAAGAGAAGG       2220

TGCTGAACCA TCCCCTGTCC TGAGAGGTGC CAGCCTGCAG GCAGTGGC                   2268

(2) INFORMATION FOR SEQ ID NO:5:

(i) SEQUENCE CHARACTERISTICS:
          (A) LENGTH: 44 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:5:

ACCGGGAATT CTTCCTTCCA GGTTCTGTGG ACAATCACAA TGGG                         44
```

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CACGGGAGCT CGCTATTACA CTTTTCCAGT GG                       32

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TACCCCGGGC ATGTCCCCAA AGAGAGC                            27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCGCTCGAGG CTGCTGTCAC TATGACC                            27

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CACAGGAGCT CCAGTTGCAG GTTAGGAGG                          29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCAGGAATT CAGCTTGAGT CTCCTCAGG                          29

(2) INFORMATION FOR SEQ ID NO:11:

(i) SEQUENCE CHARACTERISTICS:
        (A) LENGTH: 52 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

AGGTGCACGG CCCACCGTGG CCACTAGTAC TTACCCGGGG ACCTCAGACC AC         52

(2) INFORMATION FOR SEQ ID NO:12:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GGGGTACCCG TTAGTCTAGA AATGTGATTG TCCACAGAAC                       40

(2) INFORMATION FOR SEQ ID NO:13:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GGGGTACCAA GGAGGGTCTG TCCTGTTCG                                   29

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

CCGCTCGAGG CTGCTGTCAC TATGACC                                     27

(2) INFORMATION FOR SEQ ID NO:15:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

TTTGGATCCT CGGCCATGTG GCTCCGGAGC CATCG                            35

(2) INFORMATION FOR SEQ ID NO:16:

(i) SEQUENCE CHARACTERISTICS:
            (A) LENGTH: 26 base pairs
            (B) TYPE: nucleic acid
            (C) STRANDEDNESS: single
            (D) TOPOLOGY: linear -continued (ii) MOLECULE TYPE: DNA (genomic)

(xi) SEQUENCE DESCRIPTION: SEQ ID NO:16:

AAAGTCGACT CAAGGCTTAG CCAATC                                        26

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

AATATTAGCC AGAAGCAG                                                 18

(2) INFORMATION FOR SEQ ID NO:18:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

TCGAGTACTC AACAACGAAT GTT                                           23

(2) INFORMATION FOR SEQ ID NO:19:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

ATGCGAATTC GGCGCGCCAC GCGTGCGGCC GCAAGGCCAA TTAGGCCTAC GTAGGCGCGC   60

CGAATTCTCG                                                          70

(2) INFORMATION FOR SEQ ID NO:20:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CGAGAATTCG GCGCGCCTAC GTAGGCCTAA TTGGCCTTGC GGCCGCACGC GTGGGGCGCC   60

GAATTCGCAT                                                          70

(2) INFORMATION FOR SEQ ID NO:21:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:21:

TATAGCGGCC GCAAGGCCAA TTAGGCCATG TGAAAAAGGA ATGAAATTGA GATATTG                57

(2) INFORMATION FOR SEQ ID NO:22:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

AGCATGGATC CGGCCCTGTA AGTACAGTGG                                              30

(2) INFORMATION FOR SEQ ID NO:23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

ATCATACGTA TTGGGCTTTT CTTCCACCTG                                              30

(2) INFORMATION FOR SEQ ID NO:24:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

ATTTGTCGAC CCACTTGCTT CATCTTAATC                                              30

(2) INFORMATION FOR SEQ ID NO:25:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

CACGGGAGCT CATACATCAA TGGTGTGTTA AAGC                                         34

(2) INFORMATION FOR SEQ ID NO:26:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

```
CGGGGTACCC GTTAGTCTAG AAATGTGATT GTCCACAGAA C                41
```

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
AATACCAGGA TTTGAGCACC ACC                                    23
```

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
ACACACTTTG AGGGTCAGGG TG                                     22
```

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
GAGCATTGCA ATTTCAACGA CGTC                                   24
```

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
TGGTGTTGAC TTAGGGATGA AGGC                                   24
```

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
ATTGTTGTTG CGTCCCA                                           17
```

(2) INFORMATION FOR SEQ ID NO:32:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

CGGAGAAGGA GTACAGC                                                      17

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

TCCACAACCT GGTTTGCCAG                                                   20

(2) INFORMATION FOR SEQ ID NO:34:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

AGGATGCTAC CTACATTCAA GCCAC                                             25

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

CAAACAGCCT TATATCACTC                                                   20

(2) INFORMATION FOR SEQ ID NO:36:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

AAGGCAAGTT AGTTTTGGTG                                                   20

(2) INFORMATION FOR SEQ ID NO:37:

(i) SEQUENCE CHARACTERISTICS:
            (A) LENGTH: 70 base pairs
            (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:37:

ATGCGAATTC GGCGCGCCAC GCGTGCGGCC GCAAGGCCAA TTAGGCCTAC GTAGGCGCGC        60

CGAATTCTCG                                                              70

(2) INFORMATION FOR SEQ ID NO:38:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

CGAGAATTCG GCGCGCCTAC GTAGGCCTAA TTGGCCTTGC GGCCGCACGC GTGGCGCGCC        60

GAATTCGCAT                                                              70

(2) INFORMATION FOR SEQ ID NO:39:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

TATAGCGGCC GCAAGGCCAA TTAGGCCATG TGAAAAAGGA ATGAAATTGA GATATTG           57

(2) INFORMATION FOR SEQ ID NO:40:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:40:

AGCATGGATC CGGCCCTGTA AGTACAGTGG                                         30

(2) INFORMATION FOR SEQ ID NO:41:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:41:

ATCATACGTA TTGGGCTTTT CTTCCACCTG                                         30

(2) INFORMATION FOR SEQ ID NO:42:

(i) SEQUENCE CHARACTERISTICS:
            (A) LENGTH: 30 base pairs
            (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:42:

ATTTGTCGAC CCACTTGCTT CATCTTAATC                                        30
```